(12) United States Patent
Nagiec et al.

(10) Patent No.: US 9,526,720 B2
(45) Date of Patent: Dec. 27, 2016

(54) MODULATORS OF HEPATIC LIPOPROTEIN METABOLISM

(71) Applicant: The Broad Institute, Inc., Cambridge, MA (US)

(72) Inventors: Marek Maria Nagiec, Medford, MA (US); Jose R. Perez, Salem, CT (US); Michelle Palmer, Harvard, MA (US); Adam Skepner, Woburn, MA (US); Eamon Comer, Watertown, MA (US)

(73) Assignee: The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 14/421,778

(22) PCT Filed: Aug. 19, 2013

(86) PCT No.: PCT/US2013/055630
§ 371 (c)(1),
(2) Date: Feb. 13, 2015

(87) PCT Pub. No.: WO2014/028946
PCT Pub. Date: Feb. 20, 2014

(65) Prior Publication Data
US 2015/0216855 A1    Aug. 6, 2015

Related U.S. Application Data

(60) Provisional application No. 61/782,872, filed on Mar. 14, 2013, provisional application No. 61/684,281, filed on Aug. 17, 2012.

(51) Int. Cl.
*A61K 31/4725*  (2006.01)
*C07D 401/06*   (2006.01)
*C07D 493/04*   (2006.01)
*C07D 498/04*   (2006.01)
*C07D 305/08*   (2006.01)
*A61K 31/35*    (2006.01)
*A61K 31/381*   (2006.01)
*A61K 31/4025*  (2006.01)
*A61K 31/422*   (2006.01)
*A61K 45/06*    (2006.01)
*C12Q 1/68*     (2006.01)

(52) U.S. Cl.
CPC .......... *A61K 31/4725* (2013.01); *A61K 31/35* (2013.01); *A61K 31/381* (2013.01); *A61K 31/4025* (2013.01); *A61K 31/422* (2013.01); *A61K 45/06* (2013.01); *C07D 305/08* (2013.01); *C07D 401/06* (2013.01); *C07D 493/04* (2013.01); *C07D 498/04* (2013.01); *C12Q 1/6883* (2013.01); *C12Q 2600/136* (2013.01); *C12Q 2600/158* (2013.01)

(58) Field of Classification Search
CPC ............................. A61K 31/35; A61K 31/4752
USPC ............................................... 514/455
See application file for complete search history.

(56) References Cited

U.S. PATENT DOCUMENTS

| | | | |
|---|---|---|---|
| 3,505,320 | A | 4/1970 | Dabritz et al. |
| 3,857,859 | A | 12/1974 | Tumolo |
| 3,933,861 | A | 1/1976 | Kurkov |
| 4,034,051 | A | 7/1977 | Dempf et al. |
| 5,017,602 | A | 5/1991 | Cannon |
| 7,314,960 | B1 | 1/2008 | Lin et al. |
| 2004/0102327 | A1 | 5/2004 | Hagemann et al. |

FOREIGN PATENT DOCUMENTS

| | | | |
|---|---|---|---|
| CH | 494243 | A | 7/1970 |
| DE | 1010530 | B | 6/1957 |
| DE | 2449667 | A1 | 4/1976 |
| DE | 19749720 | A1 | 5/1999 |
| FR | 2865732 | A1 | 8/2005 |
| WO | 2010114179 | A1 | 10/2010 |

OTHER PUBLICATIONS

C. Plessis, "The Search for Innovative Fragrant Molecules," Chemistry & Biodiversity, vol. 5, pp. 1083-1097, (2008).
D. T. Witiak et al., "Synthesis and Pharmacological Evaluation of cis-3,4,4a,9a-Tetrahydro-1H-pyrano [3,4-b] benzofuran=1-ons. Tricyclic Analogues Related to the Antilipidemic Drug Clofibrate," Journal of Medicinal Chemistry, vol. 22, No. 6, pp. 699-705, (1979).
L. A. Erreda et al., "Polymer Swelling 20. Sorption of Cyclic Mono- and Polyethers by Poly(styrene-co-divinylbenzene)," Journal of Physical Chemistry, vol. 101, No. 39, pp. 7794-7808, (1997).
A. Entrena et al., "A New Systematization of the Conformational Behavior of Seven-Membered Rings. Isoclinal Anomeric and related Orientations," Journal of Organic Chemistry, vol. 62, No. 2, pp. 337-349, (1997).
Montaudon E. et al., "Synthese De Nouveaux Alkyl-2 ET-3 Tetrahydrofurannes ET-Pyrannes//Synthesis of New 2- and 3-Alkyltetrahydrofurans and -Pyrnas," Journal of Heterocyclic Chemistry, Wiley-Blackwell Publishing, Inc., vol. 16, No. 1, pp. 113-121, (1979).
Suginome M. et al., "beta-Borylallylsilanes as a New Tool for Convenient Synthesis of Alkenylboranes," Journal of the American Chemical Society, ACS Publications, vol. 123, No. 19, pp. 4601-4602, (2001).
Yadav et al., "Enantioselective Reduction of 2-Substituted Tetrahydropyran-4-Ones using Daucus Carota Plant Cells," Tetrahedron Letters, Pergamon, GB, vol. 49, No. 17, pp. 2768-2771, (2008).

*Primary Examiner* — Taofiq A Solola
(74) *Attorney, Agent, or Firm* — Melissa Hunter-Ensor; Elbert Chiang; Greenberg Traurig, LLP

(57) ABSTRACT

The present invention relates to compounds that are useful for modulating hepatic cholesterol metabolism in an animal. The invention includes methods of making and using the compounds of the invention. The invention further provides methods of treating, preventing and/or alleviating a cholesterol related disorder, a cardiovascular disease and/or liver disease in an animal, such as a human, comprising administering compounds of the invention, or pharmaceutically acceptable salts or solvates thereof, to the animal.

13 Claims, 12 Drawing Sheets

FIG. 2A
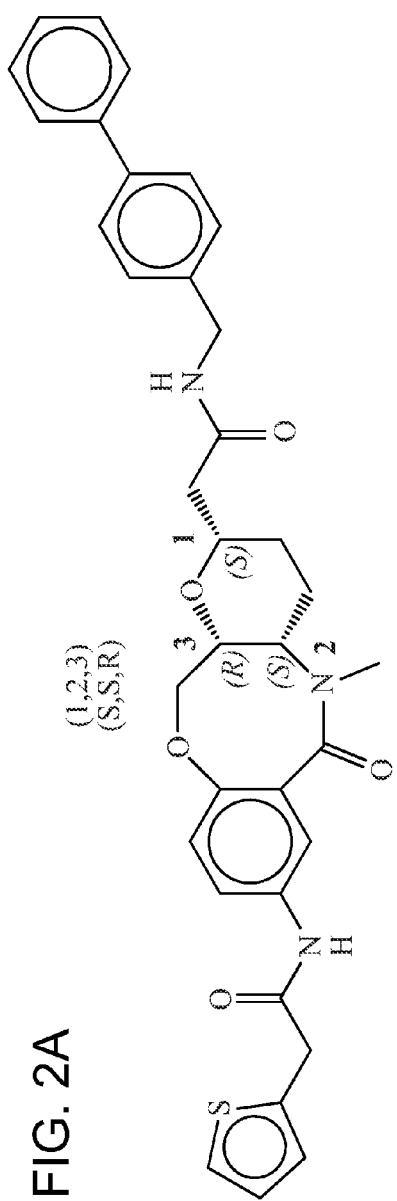
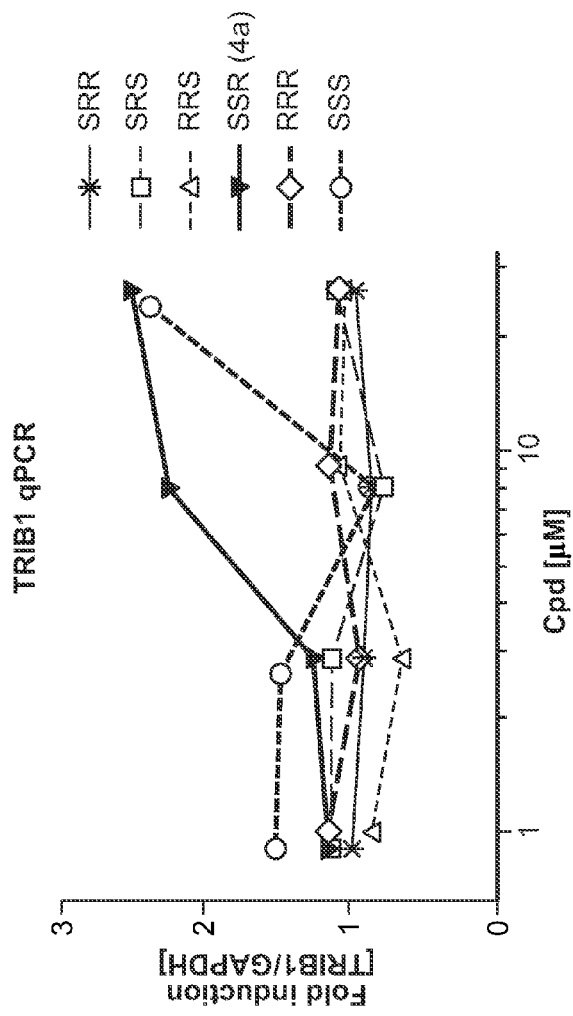

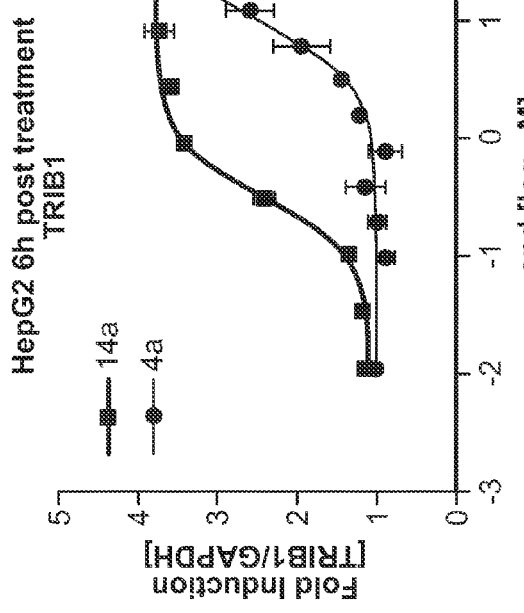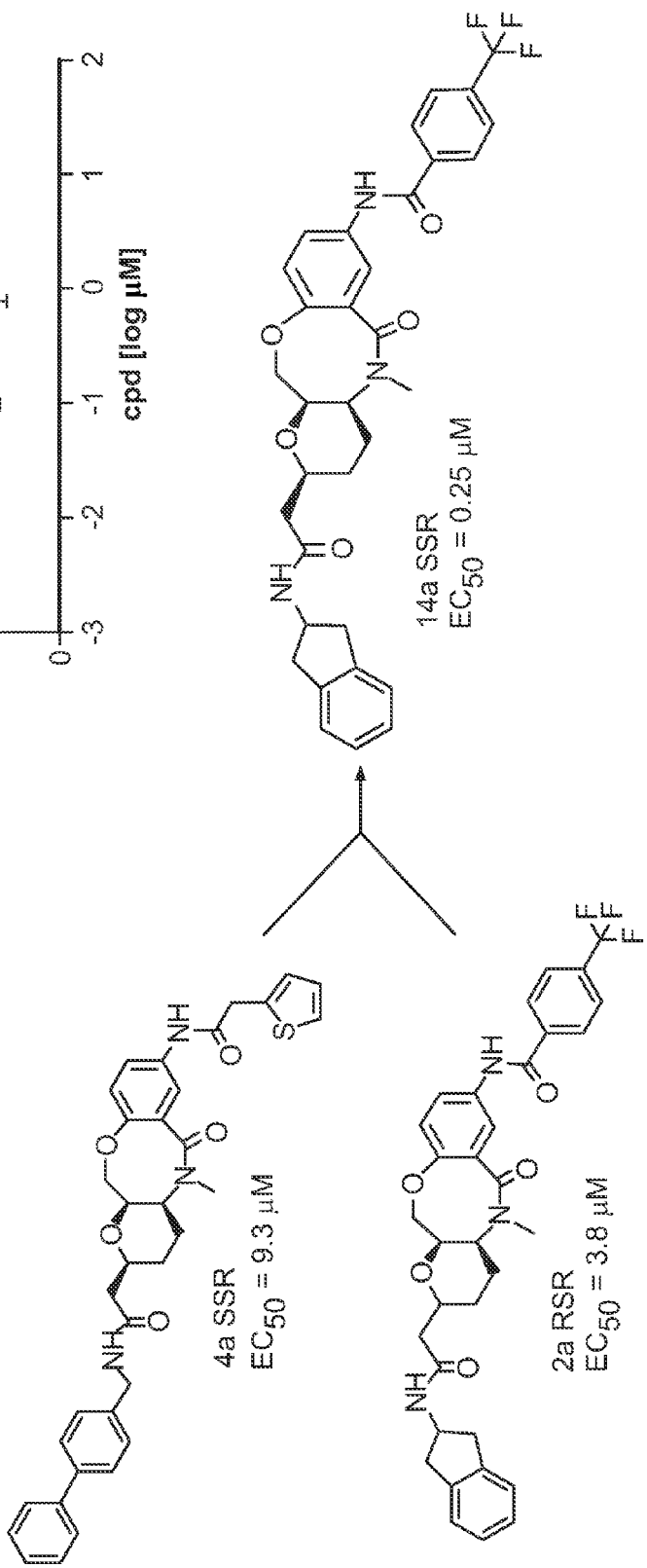
FIG. 2B

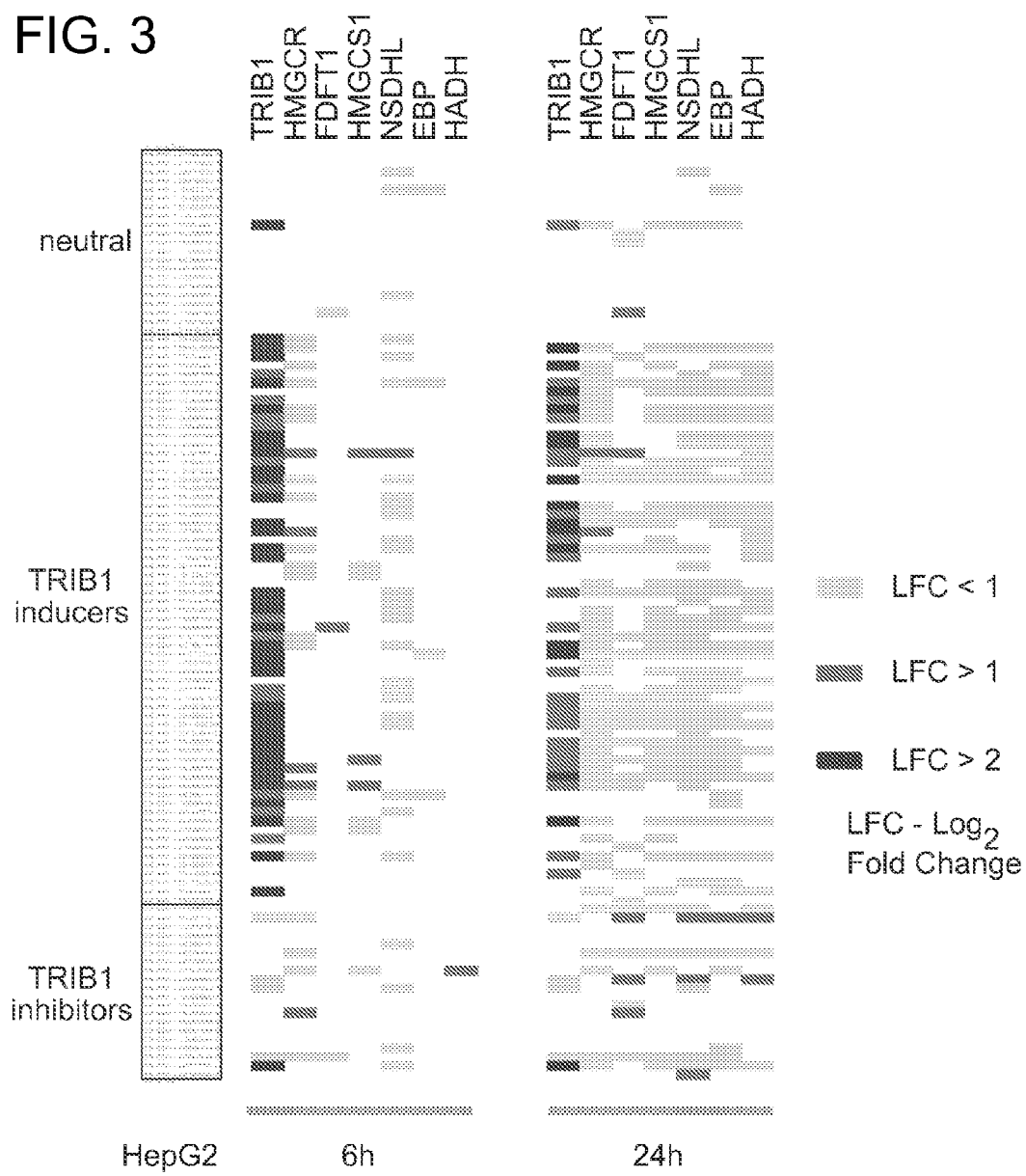

FIG. 4A  Natural product – plant alkaloid
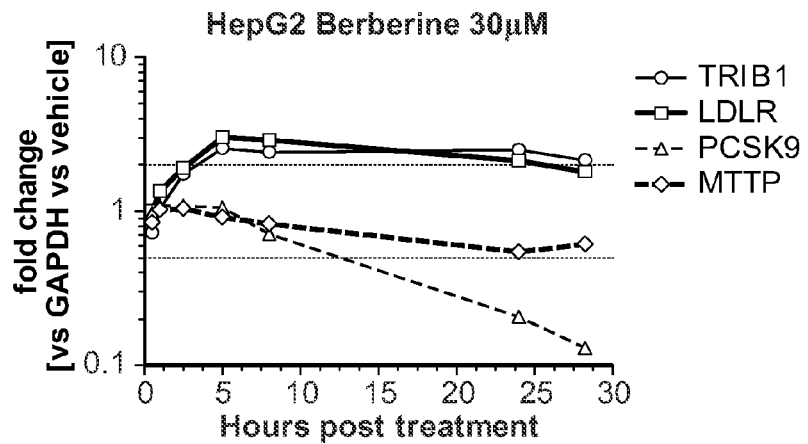
FIG. 4B  Benzofuran series
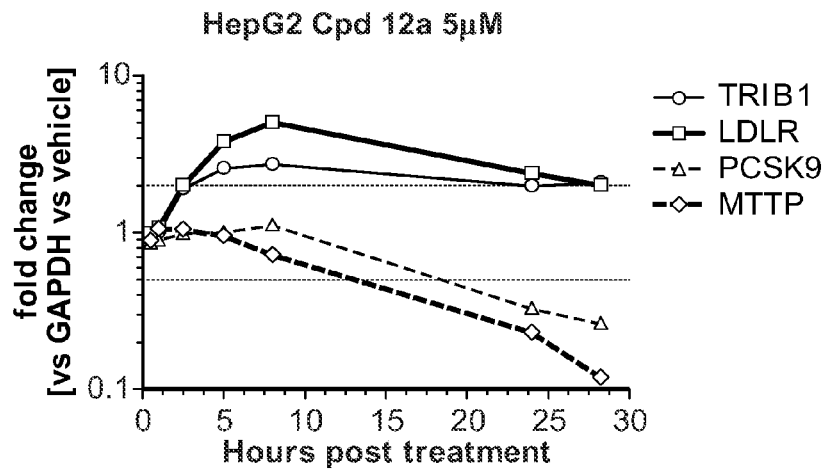
FIG. 4C  Tricyclic glycal series
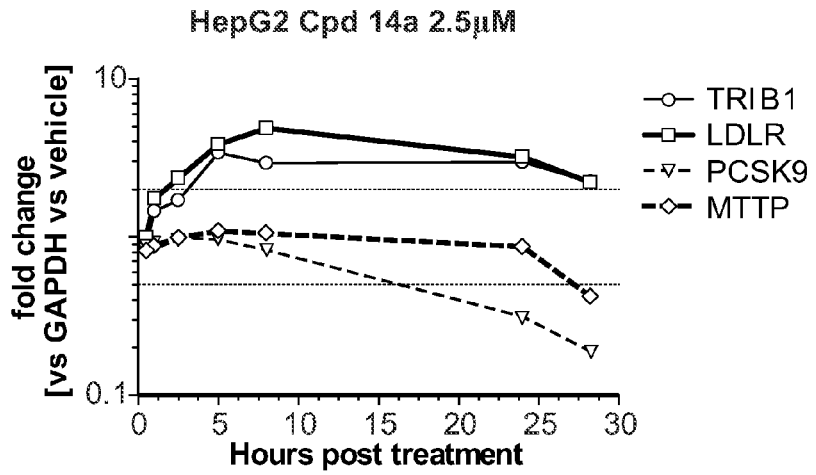

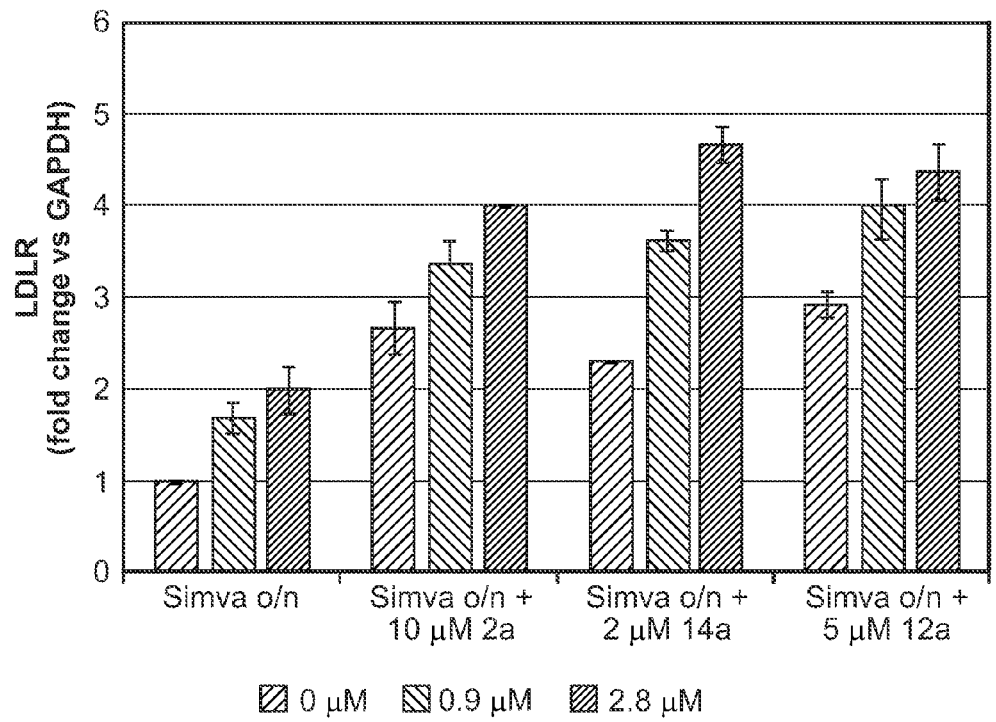
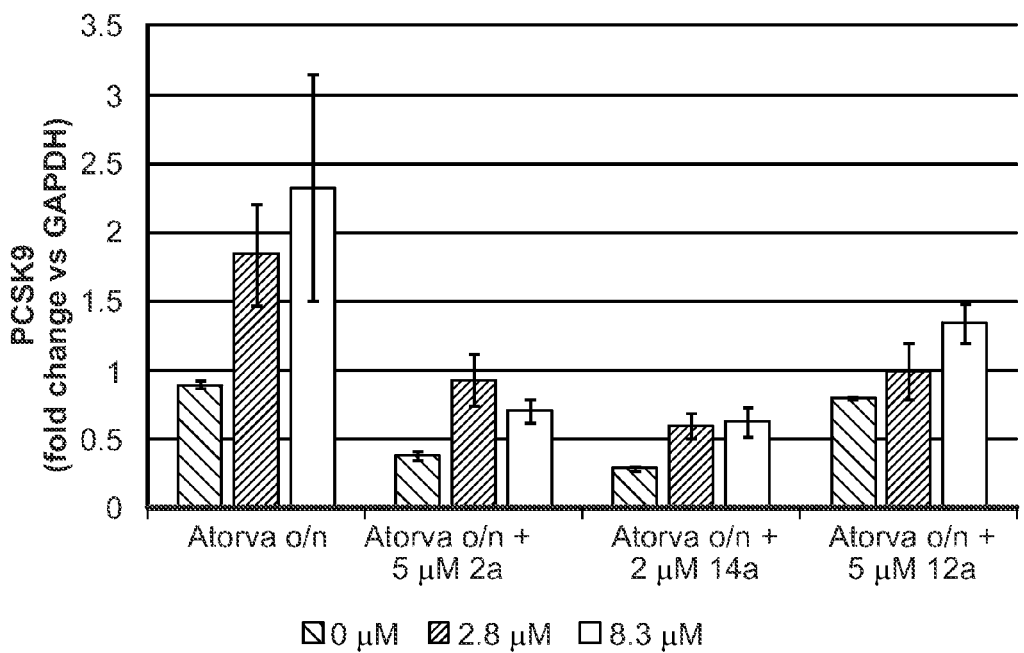

Formula I

MODULATORS OF HEPATIC LIPOPROTEIN METABOLISM

CROSS-REFERENCE TO RELATED APPLICATIONS

The present application is a 35 U.S.C. §371 national phase application of, and claims priority to, PCT Application No. PCT/US13/055630, filed Aug. 19, 2013, which claims priority under 35 U.S.C. §119(e) to U.S. Provisional Patent Applications No. 61/782,872, filed Mar. 14, 2013, and No. 61/684,281, filed Aug. 17, 2012.

BACKGROUND OF THE INVENTION

Cardiovascular disease is one of the leading causes of death worldwide. It is estimated that over 70 million people in the United States alone suffer from a cardiovascular disease, such as hypercholesterolemia, myocardial infarction, and coronary artery disease. Heterozygous familial hypocholesterolemia is a common genetic disorder, with a prevalence of 1/500 that leads to elevated low-density lipoprotein cholesterol (LDL-C) in circulation, and is associated with increased risk of coronary artery disease and myocardial infarction.

There is compelling evidence from population-based data and clinical trials that LDL-C reduction is an effective strategy for preventing coronary artery disease, slowing its progression or reducing damage (Grundy et al., Circulation, 2004, 110, 222-239). Statins are efficacious LDL-C lowering agents that represent the current therapy of choice. Despite the widespread use of statins, almost half a million people die from myocardial infarction each year in the United States alone. Recent surveys have shown that patients who are at the highest cardiovascular risk are also the ones that fail more often to achieve their therapeutic goal, in particular diabetics (Davidson et al., Am. J. Cardiol. 2005, 96, 556-563). Some patients also require larger reductions of LDL-C due to their high baseline levels, like those with familial hypercholesterolemia. A substantial proportion of patients are also intolerant to statin therapy. Therefore, there is a critical need for additive or replacement therapy to statins for improved treatments for cardiovascular diseases and related disorders.

SUMMARY OF THE INVENTION

The invention relates generally to the field of compounds for modulating cardiovascular disease and/or liver disease and to methods of making and using them. These compounds or pharmaceutically acceptable salts or solvates thereof are useful for treating, preventing, and/or alleviating a cardiovascular disease and/or liver disease in a human or animal.

More specifically, the invention relates to a compound or a pharmaceutically acceptable salt or solvate there of having the formula I:

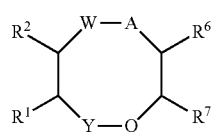

(I)

or a pharmaceutically acceptable salt thereof, wherein $R^1$, $R^2$, W, A, Y, $R^6$, and $R^7$ can be selected from the respective groups of chemical moieties later defined in the detailed description.

In addition, the invention provides pharmaceutical compositions comprising an effective amount of a compound of the invention and a pharmaceutical carrier, diluent, or excipient.

In one aspect, the invention provides a method of treating or preventing cardiovascular disease in a subject in need thereof comprising administering to the subject an effective amount of a compound of the invention or a pharmaceutically acceptable salt or solvate thereof. In one aspect, the cardiovascular disease is myocardial infarction, coronary heart disease, atherosclerosis or hypercholesterolemia. In one aspect, the cardiovascular disease is any cardiovascular disease that can be treated by increasing expression levels of TRIM. In one aspect, the cardiovascular disease is any cardiovascular disease that can be prevented by increasing expression levels of TRIM.

In one aspect, the invention provides a method of treating or preventing a liver disease or disorder in a subject in need thereof comprising administering to the subject an effective amount of a compound of the invention or a pharmaceutically acceptable salt or solvate thereof. In one aspect, the liver disease or disorder is liver cirrhosis, hepatocellular carcinoma, liver injury or abnormal liver function.

In one aspect, the invention provides a method of treating or preventing a disease in a subject in need thereof comprising administering to the subject an effective amount of a compound of the invention or a pharmaceutically acceptable salt or solvate thereof, wherein said compound downregulates the expression level of PCSK9 and upregulates expression level of TRIM. In one aspect, the disease is a cardiovascular disease or a liver disease or disorder. In one aspect, the subject is at an elevated risk for cardiovascular disease. In one aspect, the expression level of PCSK9 is down regulated by at least about 30%. In one aspect, the expression level of TRIB1 is up regulated by at least about 50%.

In one aspect, the invention provides a method of assessing the efficacy of a therapeutic agent for treating a disease in a subject comprising: (a) determining the expression level of TRIB1 in a sample from the subject; and (b) comparing the expression level of TRIB1 to a reference profile, wherein an increase in TRIB1 expression compared to the reference profile indicates that the therapeutic agent is effective for treating the disease.

In one aspect, the invention provides a method of assessing the efficacy of a therapeutic agent for treating a disease in a subject comprising: (a) determining the expression level of TRIB1 and PCSK9 in a sample from the subject; and (b) comparing the expression level of TRIB1 and PCSK9 to a reference profile; wherein an increase in TRIB1 expression and a decrease in PCKS9 expression compared to the reference profile indicates that the therapeutic agent is effective for treating the disease. In one aspect, the disease is any disease that is associated with decreased expression of TRIB1. In one aspect, the disease is any disease that is treated or prevented by increasing TRIM.

In one aspect, the invention provides a method, wherein the disease is any cardiovascular disease or lipoprotein related disorder (e.g., cholesterol related disorder) that is associated with decreased expression of TRIM. In one aspect, the disease is any cardiovascular disease or lipoprotein related disorder (e.g., cholesterol related disorder) that is treated or prevented by increasing TRIM.

In one aspect, the invention provides a method, wherein determining the expression level is determining the level of protein or RNA transcripts.

In one aspect, the invention provides a method, wherein the reference profile is obtained from a subject that does not have the disease.

In one aspect, the invention provides a method, wherein said expression level of TRIB1 in the subject is upregulated by at least about 50%.

In one aspect, the invention provides a method, wherein said expression level of PCSK9 is downregulated by at least about 50%.

In one aspect, the invention provides a method, wherein the therapeutic agent is a compound of the invention or a pharmaceutically acceptable salt of solvate thereof.

In one aspect, the invention provides a method, wherein the disease is a cardiovascular disease. In one aspect, the invention provides a method, wherein the disease is a cholesterol related disorder. In one aspect, the disease is a lipoprotein related disorder.

In one aspect, the invention provides a method of assessing the efficacy of a therapeutic agent for treating a disease in a subject comprising: (a) determining the protein expression level of ApoB in a sample from the subject; and (b) comparing the protein expression level of ApoB to a reference profile; wherein a decrease in expression compared to the reference profile indicates that the therapeutic agent is effective for treating the disease. In one aspect, the protein expression level of ApoB in the sample from the subject is down regulated by at least about 50%. In one aspect, the protein expression level of ApoB decreased by at least about 2-fold, 3-fold, 4-fold, 5-fold, 10-fold, 15-fold, or 20-fold.

In one aspect, the invention provides a method of assessing the efficacy of a therapeutic agent for treating a disease in a subject comprising: (a) determining the protein expression level of LDLR in a sample from the subject; and (b) comparing the protein expression level of LDLR to a reference profile; wherein an increase in expression compared to the reference profile indicates that the therapeutic agent is effective for treating the disease. In one aspect, the protein expression level of LDLR in the sample from the subject is up regulated by at least about 50%. In one aspect, the protein expression level of LDLR is increased by at least about 1.5-fold, 2-fold, 3-fold, 4-fold, 5-fold, 10-fold, 15-fold, or 20-fold.

In one aspect, the invention provides a method of assessing the efficacy of a therapeutic agent for treating a disease in a subject comprising: (a) determining the protein expression level of PCSK9 in a sample from the subject; and (b) comparing the protein expression level of PCSK9 to a reference profile; wherein a decrease in expression as compared to the reference profile indicates that the therapeutic agent is effective for treating the disease. In one aspect, the protein expression level of PCSK9 in the sample from the subject is down regulated by at least about 50%. In one aspect, the protein expression level of PCSK9 is decreased by at least about 1.5-fold, 2-fold, 3-fold, 4-fold, 5-fold, 10-fold, 15-fold, or 20-fold.

In one aspect, the invention provides a method of assessing the efficacy of a therapeutic agent for treating a disease in a subject comprising: (a) determining the RNA transcript level of MTTP in a sample from the subject; and (b) comparing the RNA transcript level of MTTP to a reference profile; wherein a decrease in expression compared to the reference profile indicates that the therapeutic agent is effective for treating the disease. In one aspect, the RNA transcript level of MTTP in the sample from the subject is down regulated by at least about 50%. In one aspect, the RNA transcript level of MTTP is decreased by at least about 1.5-fold, 2-fold, 3-fold, 4-fold, 5-fold, 10-fold, 15-fold, or 20-fold.

In one aspect, the invention provides a method of assessing the efficacy of a therapeutic agent for treating a disease in a subject comprising: (a) determining the RNA transcript level of APOC3 in a sample from the subject; and (b) comparing the RNA transcript level of APOC3 to a reference profile; wherein a decrease in expression compared to the reference profile indicates that the therapeutic agent is effective for treating the disease. In one aspect, the RNA transcript level of APOC3 in the sample from the subject is down regulated by at least about 50%. In one aspect, the RNA transcript level of APOC3 is decreased by at least about 1.5-fold, 2-fold, 3-fold, 4-fold, 5-fold, 10-fold, 15-fold, or 20-fold.

In one aspect, the invention provides a method of assessing the efficacy of a therapeutic agent for treating a disease in a subject comprising: (a) determining the RNA transcript level of SREBF1 in a sample from the subject; and (b) comparing the RNA transcript level of SREBF1 to a reference profile; wherein a decrease in expression compared to the reference profile indicates that the therapeutic agent is effective for treating the disease. In one aspect, the RNA transcript level of SREBF1 in the sample from the subject is down regulated by 1-2 fold.

In one aspect, the invention provides a method of assessing the efficacy of a therapeutic agent for treating a disease in a subject comprising: (a) determining the RNA transcript level of HMGCR in a sample from the subject; and (b) comparing the RNA transcript level of HMGCR to a reference profile; wherein a decrease in expression compared to the reference profile indicates that the therapeutic agent is effective for treating the disease. In one aspect, the RNA transcript level of HMGCR in the sample from the subject is down regulated by at least 50%. In one aspect, the RNA transcript level of HMGCR is decreased by about 2-fold, 3-fold, 4-fold, 5-fold, 10-fold, 15-fold, or 20-fold.

In one aspect, the invention provides a method of assessing the efficacy of a therapeutic agent for treating a disease in a subject comprising: (a) determining the RNA transcript level of HMGCS in a sample from the subject; and (b) comparing the RNA transcript level of HMGCS to a reference profile; wherein a decrease in expression compared to the reference profile indicates that the therapeutic agent is effective for treating the disease. In one aspect, the RNA transcript level of HMGCS in the sample from the subject is down regulated by at least about 2-fold.

In one aspect, the invention provides a method of assessing the efficacy of a therapeutic agent for treating a disease in a subject comprising: (a) determining the RNA transcript level of FASN in a sample from the subject; and (b) comparing the RNA transcript level of FASN to a reference profile; wherein a decrease in expression compared to the reference profile indicates that the therapeutic agent is effective for treating the disease. In one aspect, the RNA transcript level of FASN in the sample from the subject is down regulated by at least about 2-fold.

In one aspect, the invention provides a method of assessing the efficacy of a therapeutic agent for treating a disease in a subject comprising: (a) determining the RNA transcript level of SCD1 in a sample from the subject; and (b) comparing the RNA transcript level of SCD1 to a reference profile; wherein a decrease in expression compared to the reference profile indicates that the therapeutic agent is effective for treating the disease. In one aspect, the RNA transcript level of SCD1 in the sample from the subject is down regulated by at least about 2-fold.

In any of the foregoing methods, the reference profile is obtained from a subject that does not have the disease.

In any of the foregoing methods, the therapeutic agent is a compound of the invention or a pharmaceutically acceptable salt of solvate thereof.

In any of the foregoing methods, the disease is a cardiovascular disease. In any of the foregoing methods the disease is a lipoprotein related disorder (e.g., cholesterol related disorder).

In one aspect, the invention provides a method of synthesizing a compound of the invention or a pharmaceutically acceptable salt or solvate thereof.

In one aspect, the invention provides a medical device containing a compound of the invention or a pharmaceutically acceptable salt or solvate thereof.

BRIEF DESCRIPTION OF THE DRAWINGS

FIG. 2A a graph and illustration that show the stereochemical structure-activity relationship between Compound 4a stereoisomers and TRIB1 expression induction.

FIG. 2B a graph and scheme that show dose dependent increases in TRIB1 expression for Compound 14a SSR and 4a SSR.

FIG. 3 is a heat map that shows the L-1000 gene expression profiling results of expression of TRIB1 and six cholesterol pathway genes, with compounds clustered by function.

FIG. 4 is a series of graphs that shows the kinetics of gene expression modulation over a 28 hour time course after treatment with the following compounds at the indicated doses: (A) Berberine; (B) Compound 12a; and (C) Compound 14a. Fold change of expression (relative expression normalized to GAPDH, compared to vehicle control) was calculated for the following genes: TRIB1 (circle); LDLR (square); and PCSK9 (triangle) and MTTP (diamond).

FIG. 8A is a bar graph that shows up-regulation of LDLR expression by co-adminstration of a compound of the invention (2a, 12a and 14a) and a HMG-CoA reductase inhibitor (simvastatin).

FIG. 8B is a bar graph that shows down-regulation of PCSK9 by co-administration of a compound of the invention (2a, 12a and 14a) and a HMG-CoA reductase inhibitor (atorvastatin).

FIG. 9 is a graph that shows inhibition of the rate of triglyceride (TG) synthesis in HepG2 cells after treatment with compound 14a.

DESCRIPTION OF THE INVENTION

Figure 1A:
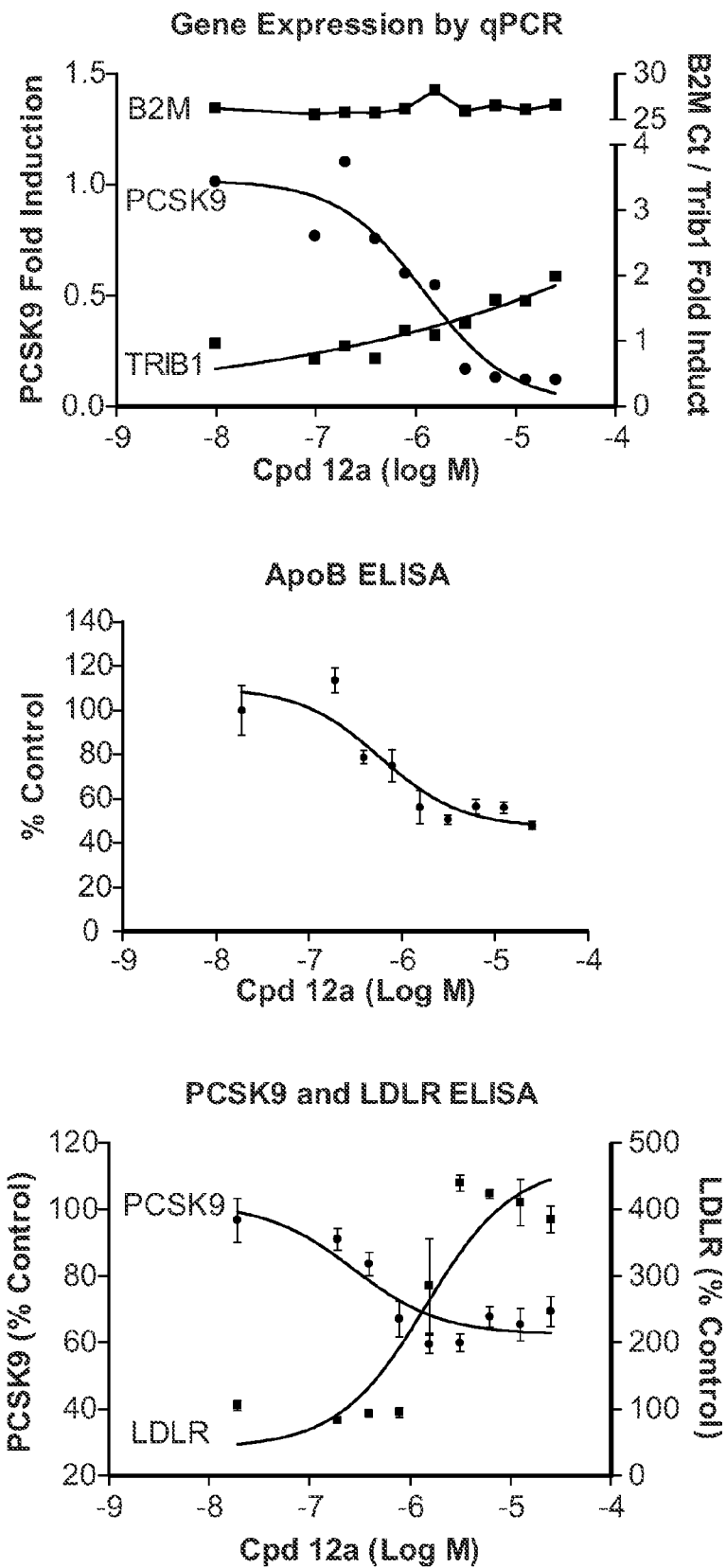
FIG. 1A-B is a series of graphs that shows the responses of HepG2 cells to indicated concentration dosages of Compound 12a (left); and Compound 2a (right). Induction of TRIB1 expression and inhibition of PCSK9 expression were measured by qPCR. Count values for the endogenous control gene B2M are also shown and demonstrate lack of effect of TRIB1 inducers on housekeeping control genes. Induction of the total LDL receptor levels in cells and inhibition of secreted ApoB and secreted PCSK9 protein levels were measured by ELISA.

Despite widespread use of statins, cardiovascular disease remains one of the leading causes of death worldwide accounting as a direct cause for 33.6% of deaths in the US (V. L. Roger et al., *Circulation* 123, e18 (Feb. 1, 2011). Epidemiological studies have repeatedly demonstrated that elevated levels of circulating LDL-C have strong association with the development of coronary artery disease (CAD) and myocardial infarction (MI). Because in humans 70% of LDL is removed from circulation by LDL receptor mediated uptake in liver, therapeutic strategies that lead to elevated hepatic expression of the LDL receptor gene (LDLR) have proven to be efficacious in lowering LDL-C and provide protection from cardiovascular disease. Statins, through the inhibition of HMG CoA reductase, deplete cholesterol in the ER of hepatic cells leading to activation of the SREBF2 dependent transcriptional program, which includes increased expression of LDLR. Paradoxically, clinical efficacy of statin therapy is limited by the fact that activation of SREBF2 also leads to increased expression of PCSK9, which acts as a negative regulator of LDL uptake by promoting degradation of LDL receptor. Recent results from clinical trials with anti-PCSK9 mAbs suggest that PCSK9 blockade may indeed provide a more efficacious mechanism for elevating LDL receptor levels than traditional inhibition of HMG CoA reductase. Alternative strategies of lowering circulating LDL-C include treatments that lower hepatic secretion of very-low-density lipoprotein (VLDL) particles—the precursor of LDL particles—into the bloodstream. Recently approved examples of such treatments include inhibitors of microsomal triglyceride transfer protein (MTP) and antisense DNA directed against apoB.

Limited efficacy as well as dose limiting toxicities of statins prevent 60% of patients from reaching their cholesterol treatment goals (S. S. Daskalopoulou, D. P. Mikhailidis, Curr Med Res Opin 22, 511 (March, 2006)) Limitations and the side effects of statins, including recent concerns about cognitive impairment and the link to diabetes, as well the side effects—particularly hepatic fat accumulation and liver toxicity—described for other treatments underscore the critical need for development of new therapeutic strategies to lower LDL-C and to prevent MI.

One technical problem to be solved by the present invention is the identification of compounds for the treatment or prevention of a lipoprotein related disorder (e.g., cholesterol related disorder), including cardiovascular disease. It is an objective of the present invention to provide a compound with a unique activity profile that favorably differs from profiles produced by statins or other lipoprotein-active therapies. TRIB1 is a novel locus strongly associated with decreased risk of coronary artery disease (CAD) and myocardial infarction (MI) as well as with decreased levels of low-density lipoprotein cholesterol (LDL-C) and triglycerides (TG) in blood. The present invention provides a compound that induces TRIB1 gene expression and modifies expression of cholesterol and triglyceride metabolic genes leading to decreased secretion of apolipoprotein B (apoB) and increased uptake of LDL by hepatic cells. In one aspect, the present invention provides a compound that inhibits the expression of PCSK9 mRNA and secretion of PCSK9 protein. This activity profile is unique and provides advantages over current therapies.

Figure 10:
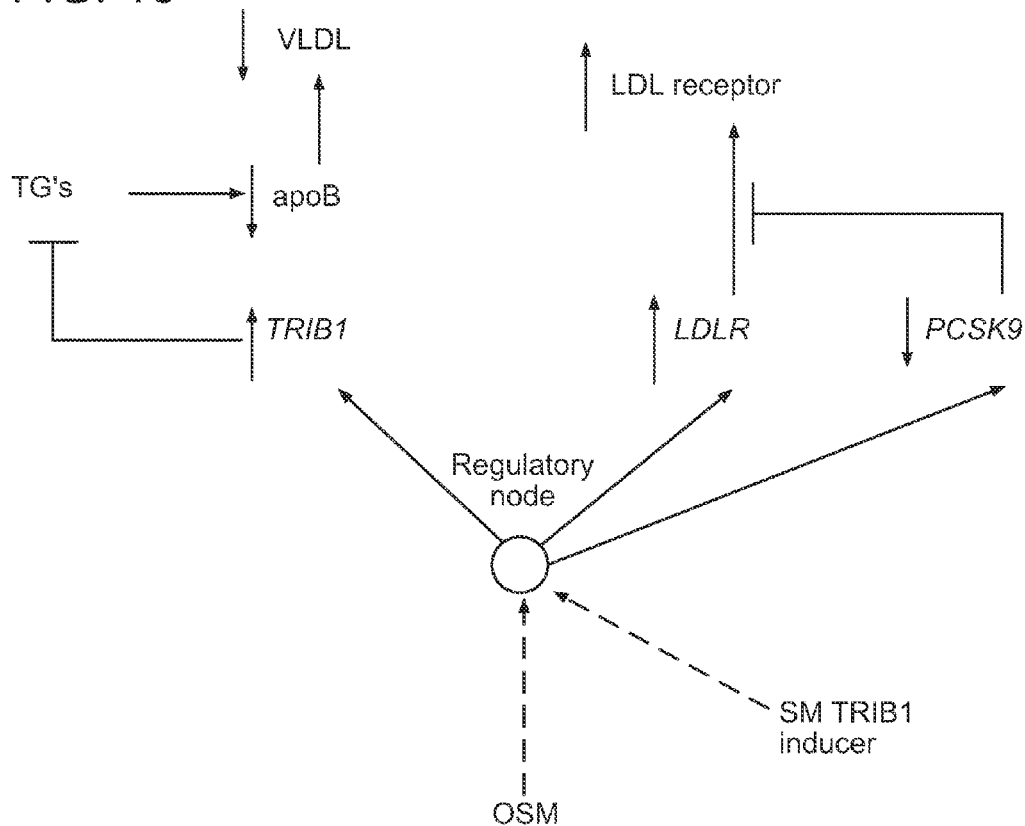
FIG. 10 is a scheme that shows a SREBF-2 independent, regulatory node present in the hepatic lipoprotein metabolic network that can be perturbed with a compound of the invention to upregulate LDL uptake.
Figure 11:
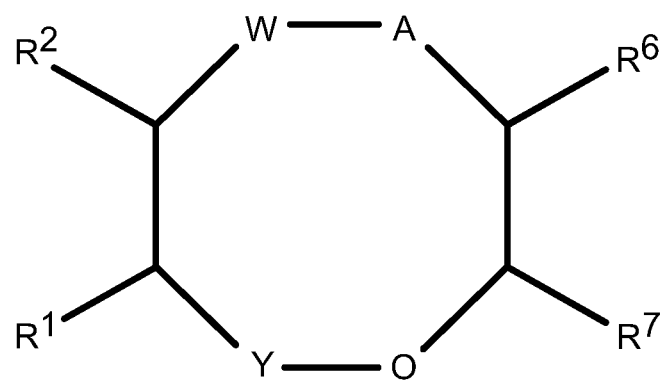
FIG. 11 is a formula of the compounds of the invention.

Without wishing to be bound by theory, the discovery of the ability of compounds of the invention to modulate LDL metabolism as described herein raises a compelling possibility that there is a novel, SREBF2 independent, regulatory node present in the hepatic lipoprotein metabolic network that can be perturbed to up-regulate LDL uptake with concomitant down-regulation of the flux through triglyceride and cholesterol biosynthetic pathways resulting in the overall increase in LDL clearance and a decrease in VLDL production as shown in FIG. 10.

For purposes of the present invention, the following definitions will be used (unless expressly stated otherwise):

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties that have 1, 2, 3, or 4 carbon atoms including methyl, ethyl, n-propyl, and n-butyl. The term "$C_3$-$C_6$ cycloalkyl" or "$C_3$-$C_6$ cycloalkyl ring" refers to cyclopropyl, cyclobutyl, cyclopentyl, and cyclohexyl. The term "$C_3$-$C_7$ cycloalkyl" or "$C_3$-$C_7$ cycloalkyl ring" also includes cycloheptyl. The term "$C_3$-$C_8$ cycloalkyl" or "$C_3$-$C_8$ cycloalkyl ring" also includes cyclooctyl. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted as specified herein.

The term "$C_4$-$C_8$ cycloalkenyl" refers cyclobutenyl, cyclopentyl, cyclohexenyl, cycloheptenyl, and cyclooctenyl rings having one or more sites of unsaturation e.g., one or more double bonds.

The term "3 to 8 membered ring" includes a 3, 4, 5, 6, 7, and 8-membered ring.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom.

The term "halogen" refers to fluoro, chloro, bromo, or iodo.

The term "hydroxyl" or "hydroxy" means OH.

The term "aryl" or "aromatic ring" alone or in combination, means a carbocyclic aromatic system containing one, two or three rings wherein such rings may be attached together in a pendent manner or may be fused. The term "aryl" or "aromatic ring" embraces aromatic radicals such as phenyl ($C_6H_6$), naphthyl, tetrahydronapthyl, indane and biphenyl, and includes carbocyclic aryl, heterocyclic aryl and biaryl groups, all of which may be optionally substituted.

The term "heteroaryl" or "heteroaromatic ring" as used herein includes 5-, 6- and 7-membered single-ring aromatic groups that also include from 1, 2, 3, or 4 heteroatoms, for example, pyrrole, furan, thiophene, imidazole, oxazole, thiazole, triazole, pyrazole, pyridine, pyrazine, pyridazine, azepine, oxepine, oxazine, triazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like.

The term "heterocyclic ring" or "heterocycle" is taken to mean a saturated, unsaturated, or partially unsaturated containing from 1, 2, 3, or 4 heteroatoms selected from nitrogen, oxygen and sulfur, said ring optionally being benzofused. A heterocylic ring can be multicyclic e.g., bicyclic or tricyclic. The term "3- to 8-membered heterocyclic ring" refers to a ring having from 3, 4, 5, 6, 7 or 8 atoms. The term "3- to 6-membered heterocyclic ring" refers to a ring having from 3, 4, 5, or 6 atoms. The term "5- to 6-membered heterocyclic ring" refers to a ring having 5 or 6 atoms. Exemplary heterocyclic rings, for the purposes of the present invention, include furanyl, thiophenyl (thienyl or thiopheneyl), pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Heterocyclic rings include bicyclic rings for example, 3-azabicyclo[3.1.0]hexane, 8-oxa-3-azabicyclo[13.2.1]octane. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted, which also of course includes optionally substituted on the benzo ring when the heterocycle is benzofused.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds unless otherwise specified. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient(s) and salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

The term "acid addition salt" refers to a salt of a compound of the invention prepared by reaction of a compound of the invention with a mineral or organic acid. For exemplification of pharmaceutically acceptable acid addition salts see, e.g., Berge, S. M, Bighley, L. D., and Monkhouse, D. C., *J. Pharm. Sci.*, 66:1, 1977. Compounds of this invention which are an amine compound are basic in nature and accordingly react with any of a number of inorganic and organic acids to form pharmaceutically acceptable acid addition salts.

Pharmaceutically acceptable acid addition salts of the invention can be formed by the reaction of a compound of the invention with an equimolar or excess amount of acid. Alternatively, hemi-salts can be formed by the reaction of a compound of the invention with the desired acid in a 2:1 ratio, compound to acid. The reactants are generally combined in a mutual solvent such as diethylether, tetrahydrofuran, methanol, ethanol, isopropanol, benzene, or the like. The salts normally precipitate out of solution within about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

Some of the compounds of the present invention may exist in unsolvated as well as solvated forms such as, for example, hydrates.

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the compounds of the invention, methods of delivering the same and compositions containing the same. "Prodrugs" are intended to include any covalently bonded carriers that release an active parent drug of the present invention in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the invention wherein a hydroxyl or amino, group is bonded to any group that, when the prodrug of the present invention is administered to a mammalian subject, it cleaves to form a free hydroxyl or free amino group, respectively. Examples of prodrugs include, but are not limited to, acetate, formate, and benzoate derivatives of alcohol and amine functional groups in the compounds of the present invention.

"Solvate" means a solvent addition form that contains either a stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "suitable solvent" refers to any solvent, or mixture of solvents, inert to the ongoing reaction that sufficiently solubilizes the reactants to afford a medium within which to effect the desired reaction.

The compounds described herein can have asymmetric centers. Compounds of the invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention. Furthermore, the invention also includes metabolites of the compounds described herein.

The invention also comprehends isotopically-labeled compounds, which are identical to those recited in the formulae of the invention, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$, $^2H$ and $^{18}F$.

Compounds of the invention and salts, hydrates, solvates or prodrugs of said compounds that contain the aforementioned isotopes and/or other isotopes of other atoms are within the scope of the present invention. Isotopically-labeled compounds of the invention, for example those into which radioactive isotopes such as $^3H$, $^{14}C$ are incorporated, are useful in drug and/or substrate tissue distribution assays. Tritiated, i.e., 3H, and carbon-14, i.e., $^{14}C$, isotopes are particularly preferred for their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, isotopically labeled compounds of this invention can generally be prepared by carrying out the procedures disclosed in the Schemes and/or in the Examples below, by substituting a readily available isotopically labeled reagent for a non-isotopically labeled reagent. In one embodiment, the compounds of the invention, salts, hydrates, solvates, or prodrugs thereof are not isotopically labelled.

When any variable (e.g., $R^h$) occurs more than one time in any constituent or formula for a compound, its definition at each occurrence is independent of its definition at every other occurrence. Thus, for example, if a group is shown to be substituted with one or more $R^h$ moieties, then $R^h$ at each occurrence is selected independently from the definition of $R^h$. Also, combinations of substituents and/or variables are permissible, but only if such combinations result in stable compounds within a designated atom's normal valency.

As used herein, the term "treat," "treatment" or "treating" herein, is meant decreasing the symptoms, markers, and/or any negative effects of a condition in any appreciable degree in a patient who currently has the condition. Treatment can include a decrease in the severity of symptoms in acute or chronic disease as well as a decrease in the relapse or exacerbation rate in relapsing-remitting disease. In one aspect, treating a disease means reversing or stopping the disease's progression. Ameliorating a disease and alleviating a disease are equivalent to treating a disease.

As used herein, the term "prevent," "prevention," or "preventing" refers to any method to partially or completely prevent or delay the onset of one or more symptoms or features of a disease, disorder, and/or condition. Prevention is causing the clinical symptoms of the disease state not to develop i.e., inhibiting the onset of disease, in a subject that may be exposed to or predisposed to the disease state, but does not yet experience or display symptoms of the disease state. Prevention may be administered to a subject who does not exhibit signs of a disease, disorder, and/or condition.

As used herein, the term "reducing the risk of" refers to any method of reducing the risk of developing a disease, disorder, and/or condition in a subject who exhibits only early signs of the condition.

As used herein, an "effective amount" of a therapeutic agent e.g. a compound of the invention refers to an amount effective, at dosages and for periods of time necessary, to achieve the desired therapeutic or prophylactic effect.

As used herein, "subject" means a human or animal (in the case of an animal, more typically a mammal). In one aspect, the subject is a human. Such subject can be considered to be in need of treatment of a cardiovascular disease.

As used herein, the term "sample" in the context of the present invention is any biological sample isolated from a subject. In one aspect, the sample is a tissue from a biopsy, including a liver biopsy sample. In one aspect, the sample is a blood sample, such as whole blood or peripheral blood mononuclear cells (PBMCs).

As used herein, "therapeutic agent" refers to any agent or compound that can be used to treat, prevent, ameliorate, lessen, or reduce at least one symptom of a disease or disorder, particularly a lipoprotein related disorder (e.g., cholesterol related disorder), cardiovascular disease or disorder or liver disease or disorder. The term "therapeutic agent" as used herein includes a compound of the invention.

In one aspect, the term "therapeutic agent" means any compound or pharmaceutically acceptable salt that can be used to treat a disease or disorder described herein. In one aspect, the term "therapeutic agent" means only a compound of the invention.

As used herein, the term "lipoprotein" refers to an assembly that contains both protein and lipid. Lipoprotein includes, e.g., cholesterol, triglycerides, and ApoB (all relevant members to this set).

For the avoidance of doubt, the term "a compound of the invention" refers to a compound disclosed herein e.g., a compound of the invention includes a compound of formulae I, II, III, IIIA, IV, IVA, X, XI, XII, XIII, XIV, XV, XVI, XVII, AA, AB, AC, AD, AE, AF, or AG or a compound in Table A. Whenever the term is used in the context of the present invention it is to be understood that the reference is being made to both the free base and the corresponding salts, solvates (hydrates) and prodrugs, provided that such is possible and/or appropriate under the circumstances.

As used herein, "a method of the invention" refers to any method described herein.

As used herein, "unsaturated" refers to compounds or structures having at least one degree of unsaturation (e.g., at least one double or triple bond).

The term "modulating" as used herein means increasing or decreasing, e.g. activity, by a measurable amount.

As used herein, the term "reference profile" means an expression profile measured in samples obtained from subjects treated with vehicle and/or placebo.

As used herein, the term "metabolism" means catabolism and anabolism.

Compounds of the Invention

The invention relates to a compound or a pharmaceutically acceptable salt or solvate there of having the formula I:

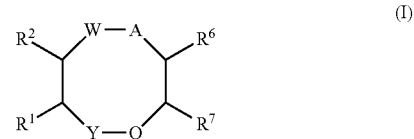

or a pharmaceutically acceptable salt or solvate thereof, wherein

W is a bond or $NR^3$;

A is a bond, $CH_2$, C=O, or $SO_2$;

Y is a bond, or $CH_2$;

$R^1$ is $C_1$-$C_8$ alkyl;

$R^2$ is hydrogen;

or $R^1$ and $R^2$ taken together form a 5- or 6-membered saturated heterocyclic ring, further wherein said saturated heterocyclic ring is unsubstituted or substituted with one or more $R^u$;

$R^u$ is selected from $(CH_2)_nC(O)NR^4R^5$ and $(CH_2)_wOH$;

$R^4$ and $R^5$ are each independently selected from hydrogen, 4-6 membered heterocyclic ring, $C_3$-$C_8$ cycloalkyl ring, and $(CH_2)_s$-aromatic ring, further wherein said heterocyclic, cycloalkyl, or aromatic ring is unsubstituted or substituted with one or more $R^x$;

or $R^4$ and $R^5$ taken together form a 4-6 membered heterocyclic ring, further wherein said heterocyclic ring is unsubstituted or substituted with two $R^a$ on adjacent carbon atoms taken together to form a fused aromatic ring;

$R^x$ is selected from $(CH_2)_g$-aromatic ring and $OR^{10}$ or two $R^x$ on adjacent carbon atoms taken together form a fused aromatic ring;
$R^{10}$ is aromatic ring;
$R^3$ is $C_1$-$C_8$ alkyl, wherein said alkyl is unsubstituted or substituted with one or more $R^e$;
$R^e$ is selected from $C_1$-$C_8$ alkyl, OH, $CF_3$, and aromatic ring, further wherein said aromatic ring is unsubstituted or substituted with one or more $R^f$;
$R^f$ is $OR^{11}$;
$R^{11}$ is $(CH_2)_q$-aromatic ring;
$R^6$ and $R^7$ are each independently selected from hydrogen, $O(C_1$-$C_8$ alkyl), 0-aromatic ring, $O(C_3$-$C_8$ cycloalkyl ring), and OH;
or $R^6$ and $R^7$ taken together form an aromatic ring, further wherein said aromatic ring is unsubstituted or substituted with one or more $R^y$;
$R^y$ is $R^{12}$ or $NR^8QR^9$;
Q is $C(O)$, $S(O)_p$, bond, $C(O)NR^8$, $C(O)CH_2$, $C(O)O$, or $C(O)OCH_2$;
$R^{12}$ is halogen, $C_1$-$C_8$ alkyl, $CF_3$, $N(C_1$-$C_8$ alkyl)$_2$, or $OR^{13}$;
$R^{13}$ is $C_1$-$C_8$ alkyl or hydrogen;
$R^8$ and $R^9$ is each independently selected from hydrogen, $C_1$-$C_8$ alkyl, $(CH_2)_t$-4-8 membered heterocyclic ring, and $(CH_2)_v$-aromatic ring, further where said alkyl, aromatic ring or heterocyclic ring are unsubstituted or substituted with one or more $R^z$;
$R^z$ is selected from halogen, $CF_3$, $C_1$-$C_8$ alkyl and $O(C_1$-$C_8$ alkyl)$_2$; or two $R^z$ on adjacent carbon atoms taken together form a 1,3-dioxole ring;
or $R^8$ and $R^9$ taken together form a 4-8 membered heterocyclic ring, further wherein said heterocyclic ring is unsubstituted or substituted with one or more $R^m$;
$R^m$ is halogen, $CF_3$, $C_1$-$C_8$ alkyl, or $OR^{17}$;
$R^{17}$ is hydrogen or $C_1$-$C_8$ alkyl;
t is 0, 1, 2, or 3;
v is 0, 1, 2, or 3;
p is 0, 1, or 2;
w is 0, 1, 2, or 3;
n is 0, 1, 2, or 3;
q is 0, 1, or 2; s is 0, 1, 2, or 3; and
g is 0, 1, 2, or 3.

In one aspect, the invention provides a compound of formula II:

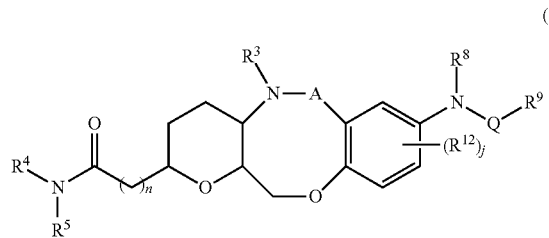

(II)

or a pharmaceutically acceptable salt or solvate thereof, wherein
A is $SO_2$, $CH_2$, or $C(O)$;
Q is $S(O)_p$, $C(O)$, bond, $C(O)NR^8$, $C(O)CH_2$, $C(O)O$, or $C(O)OCH_2$;
$R^3$ is $C_1$-$C_8$ alkyl, wherein said alkyl is unsubstituted or substituted with one or more $R^e$;
$R^e$ is selected from $C_1$-$C_8$ alkyl, $CF_3$, OH, and aromatic ring, further wherein said aromatic ring is unsubstituted or substituted with one or more $R^f$;

$R^f$ is $OR^{11}$;
$R^{11}$ is $(CH_2)_q$-aromatic ring;
$R^{12}$ is halogen, $C_1$-$C_8$ alkyl, $CF_3$, $N(C_1$-$C_8$ alkyl)$_2$, or $OR^{13}$;
$R^{13}$ is $C_1$-$C_8$ alkyl or hydrogen;
$R^4$ and $R^5$ are each independently selected from hydrogen, 4-6 membered heterocyclic ring, $C_3$-$C_8$ cycloalkyl ring and $(CH_2)_s$-aromatic ring, further wherein said heterocyclic, cycloalkyl, or aromatic ring is unsubstituted or substituted with one or more $R^x$;
or $R^4$ and $R^5$ taken together form a 4-6 membered heterocyclic ring, further wherein said heterocyclic ring is unsubstituted or substituted with two $R^a$ on adjacent carbon atoms taken together to form a fused aromatic ring;
$R^x$ is selected from $(CH_2)_g$-aromatic ring and $OR^{10}$ or two $R^x$ on adjacent carbon atoms taken together form a fused aromatic ring;
$R^{10}$ is aromatic ring;
$R^8$ and $R^9$ is each independently selected from hydrogen, $C_1$-$C_8$ alkyl, $(CH_2)_t$-4-8 membered heterocyclic ring, and $(CH_2)_v$-aromatic ring, further where said alkyl, aromatic ring or heterocyclic ring are unsubstituted or substituted with one or more $R^z$;
$R^z$ is selected from halogen, $CF_3$, $C_1$-$C_8$ alkyl, and $O(C_1$-$C_8$ alkyl);
or two $R^z$ on adjacent carbon atoms taken together form a 1,3-dioxole ring;
or $R^8$ and $R^9$ taken together form a 4-8 membered heterocyclic ring, further wherein said heterocyclic ring is unsubstituted or substituted with one or more $R^m$;
$R^m$ is halogen, $CF_3$, $C_1$-$C_8$ alkyl, or $OR^{17}$;
$R^{17}$ is hydrogen or $C_1$-$C_8$ alkyl;
s is 0, 1, 2, or 3;
p is 0, 1, or 2;
n is 0, 1, 2, or 3;
q is 0, 1, or 2;
j is 0, 1, 2, or 3;
v is 0, 1, 2, or 3;
t is 0, 1, 2, or 3; and
g is 0, 1, 2, or 3.

In one aspect, the invention provides a compound selected from formula III and IV:

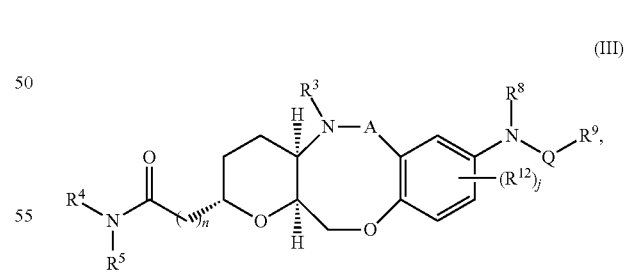

(III)

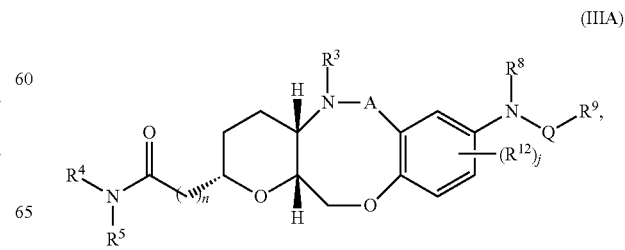

(IIIA)

-continued (IV)

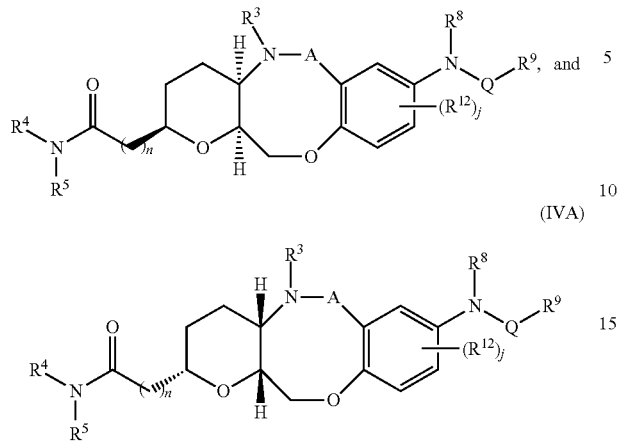

(IVA)

or a pharmaceutically acceptable salt thereof, wherein $R^3$, $R^4$, $R^5$, $R^8$, $R^9$, $R^{12}$, j, n and A are as described for formula II.

In one aspect, the invention provides a compound of formula I, II, III, IIIA, IV, or IVA, wherein A is $SO_2$. In one aspect, the invention provides a compound of formula I, II, III, IIIA, IV, or IVA, wherein A is CO. In one aspect, the invention provides a compound of formula I, II, III, IRA, IV, or IVA, wherein A is $CH_2$.

In one aspect, the invention provides a compound of formula I, II, III, IIIA, IV, or IVA, wherein Q is C(O).

In one aspect, the invention provides a compound of formula I, II, III, IIIA, IV, or IVA, wherein Q is $S(O)_p$.

In one aspect, the invention provides a compound of formula I, II, III, IIIA, IV, or IVA, wherein Q is bond.

In one aspect, the invention provides a compound of formula I, II, III, IIIA, IV, or IVA, wherein Q is $C(O)NR^8$.

In one aspect, the invention provides a compound of formula I, II, III, IIIA, IV, or IVA, wherein Q is $C(O)CH_2$.

In one aspect, the invention provides a compound of formula I, II, III, IIIA, IV, or IVA, wherein Q is C(O)O.

In one aspect, the invention provides a compound of formula I, II, III, IIIA, IV, or IVA, wherein Q is $C(O)OCH_2$. In one aspect, the invention provides a compound of formula I, II, III, IIIA, IV, or IVA, wherein n is 1.

In one aspect, the invention provides a compound of formula I, II, III, IIIA, IV, or IVA, wherein q is 0.

In one aspect, the invention provides a compound of formula I, II, III, IIIA, IV, or IVA, wherein $R^{11}$ is phenyl.

In one aspect, the invention provides a compound of formula II, III, IIIA, IV, or IVA, wherein j is 0.

In one aspect, the invention provides a compound of formula I, II, III, IIIA, IV, or IVA, wherein $R^3$ is methyl.

In one aspect, the invention provides a compound of formula I, II, III, IIIA, IV, or IVA, wherein one of $R^4$ or $R^5$ is hydrogen.

In one aspect, the invention provides a compound of formula I, II, III, IIIA, IV, or IVA, wherein $R^8$ is hydrogen.

In one aspect, the invention provides a compound of formula I, II, III, IIIA, IV, or IVA, wherein $R^9$ is selected from $(CH_2)_v$-aromatic ring or $(CH_2)_t$-4-8 membered heterocyclic ring, wherein t is 0 or 1 and v is 0 or 1, and further wherein aromatic and heterocyclic ring are unsubstituted or substituted.

In one aspect, the invention provides a compound of formula X:

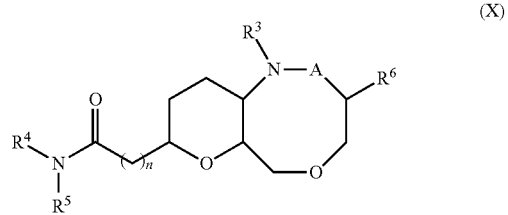

or a pharmaceutically acceptable salt or solvate thereof, wherein

A is $SO_2$, $CH_2$, or C(O);

$R^3$ is $C_1$-$C_8$ alkyl, wherein said alkyl is unsubstituted or substituted with one or more $R^e$;

$R^e$ is selected from $C_1$-$C_8$ alkyl, $CF_3$, OH, and aromatic ring, further wherein said aromatic ring is unsubstituted or substituted with one or more $R^f$;

$R^f$ is $OR^{11}$;

$R^{11}$ is $(CH_2)_q$-aromatic ring;

$R^6$ is selected from hydrogen, $O(C_1$-$C_8$ alkyl), 0-aromatic ring, $O(C_3$-$C_8$ cycloalkyl), and OH;

$R^4$ and $R^5$ are each independently selected from hydrogen, 4-6 membered heterocyclic ring, $C_3$-$C_8$ cycloalkyl ring, and $(CH_2)_s$-aromatic ring, further wherein said heterocyclic, cycloalkyl, or aromatic ring is unsubstituted or substituted with one or more $R^x$;

or $R^4$ and $R^5$ taken together form a 4-6 membered heterocyclic ring, further wherein said heterocyclic ring is unsubstituted or substituted with two $R^a$ on adjacent carbon atoms taken together to form a fused aromatic ring;

$R^x$ is selected from $(CH_2)_g$-aromatic ring and $OR^{10}$ or two $R^x$ on adjacent carbon atoms taken together form a fused aromatic ring;

$R^{10}$ is aromatic ring;

n is 0, 1, 2, or 3;

q is 0, 1, or 2;

s is 0, 1, 2, or 3; and g is 0, 1, 2, or 3.

In one aspect, the invention provides a compound selected from formula XI, XII, XIII, and XIV:

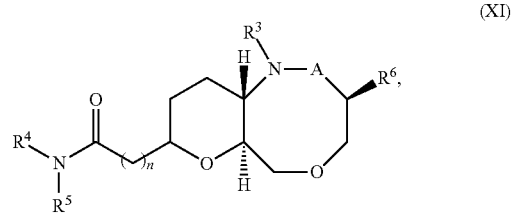

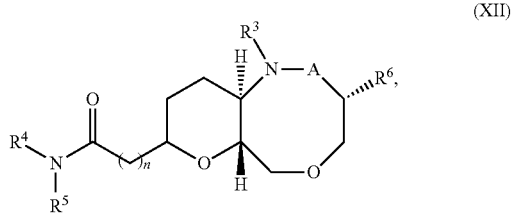

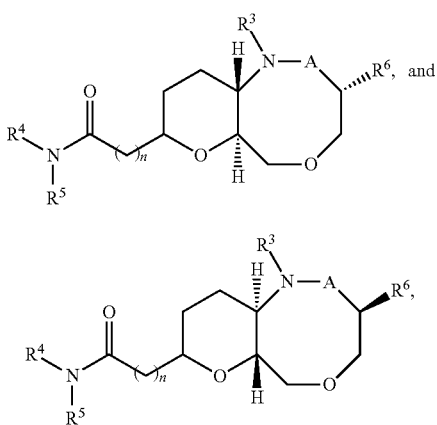

(XIII)

(XIV)

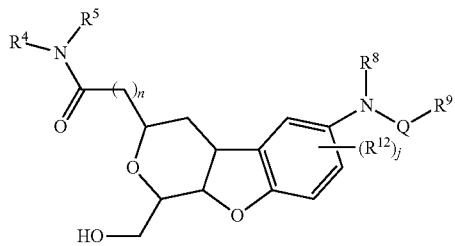

or a pharmaceutically acceptable salt or solvate thereof, wherein A, n, $R^3$, $R^4$, $R^5$ and $R^6$ are as described for formula X.

In one aspect, the invention provides a compound of formulae X, XI, XII, XIII, or XIV, wherein A is $SO_2$.

In one aspect, the invention provides a compound of formulae X, XI, XII, XIII, or XIV, wherein A is $CH_2$.

In one aspect, the invention provides a compound of formulae X, XI, XII, XIII, or XIV, wherein A is C(O).

In one aspect, the invention provides a compound of formulae X, XI, XII, XIII, or XIV, wherein n is 1.

In one aspect, the invention provides a compound of formulae X, XI, XII, XIII, or XIV, wherein $R^3$ is $C_1$-$C_8$ alkyl substituted with phenyl, further substituted with one $R^f$.

In one aspect, the invention provides a compound of formulae X, XI, XII, XIII, or XIV wherein $R^f$ is O-phenyl.

In one aspect, the invention provides a compound of formula X, XI, XII, XIII, or XIV, wherein $R^3$ is —$CH_2CH_3CF_3$.

In one aspect, the invention provides a compound of formula X, XI, XII, XIII, or XIV wherein $R^4$ and $R^5$ taken together form a 4-6 membered heterocyclic ring, further wherein said heterocyclic ring is unsubstituted or substituted with two $R^a$ on adjacent carbon atoms taken together to form a fused aromatic ring.

In one aspect, the invention provides a compound of formula X, XI, XII, XIII, or XIV wherein $R^4$ and $R^5$ taken together form a 6-membered heterocyclic ring, further wherein heterocyclic ring is unsubstituted or substituted two $R^a$ on adjacent carbon atoms taken together form a fused phenyl ring.

In one aspect, the invention provides a compound of formula X, XI, XII, XIII, or XIV, wherein $R^6$ is OH.

In one aspect, the invention provides a compound of formula X, XI, XII, XIII, or XIV, wherein $R^6$ is O($C_1$-$C_8$ alkyl).

In one aspect, the invention provides a compound of formula X, XI, XII, XIII, or XIV, wherein $R^6$ is O-aromatic ring.

In one aspect, the invention provides a compound of formula X, XI, XII, XIII, or XIV, wherein $R^6$ is O($C_3$-$C_8$ cycloalkyl ring).

In one aspect, the invention provides a compound of formula XV:

(XV)

or a pharmaceutically acceptable salt or solvate thereof, wherein
Q is C(O), S(O)$_p$, bond, C(O)$NR^8$, C(O)$CH_2$, C(O)O, or C(O)$OCH_2$;
$R^4$ and $R^5$ are each independently selected from hydrogen, 4-6 membered heterocyclic ring, $C_3$-$C_8$ cycloalkyl ring, and ($CH_2$)$_s$-aromatic ring, further wherein said heterocyclic, cycloalkyl, or aromatic ring is unsubstituted or substituted with one or more $R^x$;
or $R^4$ and $R^5$ taken together form a 4-6 membered heterocyclic ring, further wherein said heterocyclic ring is unsubstituted or substituted with two $R^a$ on adjacent carbon atoms taken together to form a fused aromatic ring;
$R^x$ is selected from ($CH_2$)$_g$-aromatic ring and $OR^{10}$ or two $R^x$ on adjacent carbon atoms taken together form a fused aromatic ring;
$R^8$ and $R^9$ is each independently selected from hydrogen, $C_1$-$C_8$ alkyl, ($CH_2$)$_t$-4-8 membered heterocyclic ring, and ($CH_2$)$_v$-aromatic ring, further wherein said alkyl, aromatic ring or heterocyclic ring are unsubstituted or substituted with one or more $R^z$;
$R^z$ is selected from halogen, $CF_3$, $C_1$-$C_8$ alkyl, and O($C_1$-$C_8$ alkyl);
or two $R^z$ on adjacent carbon atoms taken together form a 1,3-dioxole ring, or $R^8$ and $R^9$ taken together form a 4-8 membered heterocyclic ring, further wherein said heterocyclic ring is unsubstituted or substituted with one or more $R^m$;
$R^m$ is halogen, $CF_3$, $C_1$-$C_8$ alkyl, or $OR^{17}$;
$R^{17}$ is hydrogen or $C_1$-$C_8$ alkyl;
$R^{10}$ is aromatic ring,
p is 0, 1, or 2;
s is 0, 1, 2, or 3;
v is 0, 1, 2, or 3;
n is 0, 1, 2, or 3;
t is 0, 1, 2, or 3; and
g is 0, 1, 2, or 3.

In one aspect, the invention provides a compound selected from formulae XVI and XVII:

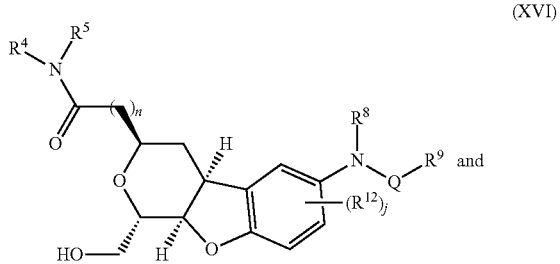

(XVI)

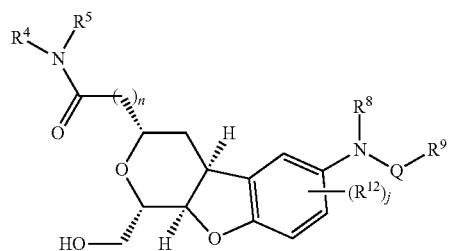

(XVII)

or a pharmaceutically acceptable salt or solvate thereof, wherein Q, $R^4$, $R^5$, $R^8$ $R^9$, $R^{12}$, and j are as described for formula XV.

In one aspect, the invention provides a compound of formula XV, XVI, or XVII, wherein n is 1.

In one aspect, the invention provides a compound of formula XV, XVI, or XVII, wherein j is 1.

In one aspect, the invention provides a compound of formula XV, XVI, or XVII, wherein Q is C(O).

In one aspect, the invention provides a compound of formula XV, XVI, or XVII, wherein Q is $S(O)_2$.

In one aspect, the invention provides a compound of formula XV, XVI, or XVII, wherein Q is bond.

In one aspect, the invention provides a compound of formula XV, XVI, or XVII, wherein Q is $C(O)NR^8$.

In one aspect, the invention provides a compound of formula XV, XVI, or XVII, wherein Q is $C(O)CH_2$.

In one aspect, the invention provides a compound of formula XV, XVI, or XVII, wherein Q is C(O)O.

In one aspect, the invention provides a compound of formula XV, XVI, or XVII, wherein Q is $C(O)OCH_2$.

In one aspect, the invention provides a compound of formula XV, XVI, or XVII, wherein $R^4$ is hydrogen.

In one aspect, the invention provides a compound of formula XV, XVI, or XVII, wherein $R^5$ is —$CH_2$-aromatic ring further substituted with one $R^z$.

In one aspect, the invention provides a compound of formula XV, XVI, or XVII, wherein $R^5$ is —$CH_2$-phenyl further substituted with $OR^{11}$.

In one aspect, the invention provides a compound of formula XV, XVI, or XVII, wherein $R^4$ and $R^5$ are both $C_1$-$C_8$ alkyl.

In one aspect, the invention provides a compound of formula XV, XVI, or XVII, wherein $R^4$ and $R^5$ are both methyl.

In one aspect, the invention provides a compound of formula XV, XVI, or XVII, wherein $R^{11}$ is unsubstituted phenyl.

In one aspect, the invention provides a compound of formula XV, XVI, or XVII, wherein $R^8$ is hydrogen.

In one aspect, the invention provides a compound of formula XV, XVI, or XVII, wherein $R^9$ is aromatic ring substituted with one or more $R^z$.

In one aspect, the invention provides a compound of formula XV, XVI, or XVII, wherein $R^9$ is phenyl substituted with two $R^z$ on adjacent carbon atoms taken together to form a 1,3-dioxole ring.

In one aspect, the present invention relates to a pharmaceutical composition comprising a compound of formula AA:

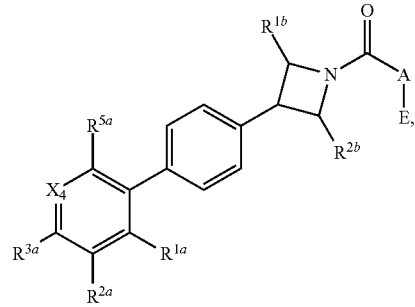

(AA)

or a pharmaceutically acceptable salt thereof and one or more pharmaceutically acceptable carriers or excipients, wherein A is a bond, —NH—, —N($C_1$-$C_8$ alkyl)-, 4-6 membered heterocyclic ring, or $C_3$-$C_8$ cycloalkyl ring;

E is $C_1$-$C_8$ alkyl, 4-6 membered heterocyclic ring, or $C_3$-$C_8$ cycloalkyl ring;

$X^4$ is $CR^{4a}$ or N;

$R^{1a}$, $R^{2a}$, $R^{3a}$, $R^{4a}$, and $R^{5a}$ are independently selected from hydrogen, halogen, $C(O)NH_2$, $C(O)NH(C_1$-$C_8$ alkyl), and $C(O)N(C_1$-$C_8$ alkyl$)_2$;

$R^{1b}$ is selected from hydrogen, halogen, OH, O($C_1$-$C_8$ alkyl), and CN; and $R^{2b}$ is selected from hydrogen, halogen, OH, ($C_1$-$C_8$ alkyl)-OH, ($C_1$-$C_8$ alkyl)-O($C_1$-$C_8$ alkyl).

In one aspect, the compound is selected from formulae AB and AC:

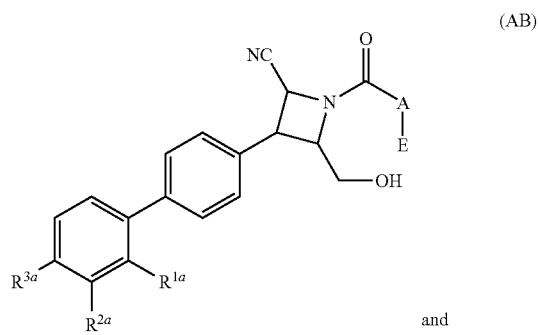

(AB)

and

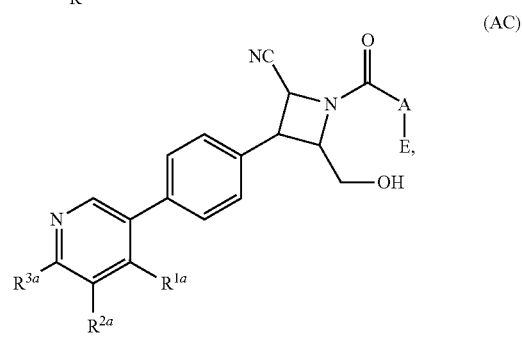

(AC)

or a pharmaceutically acceptable salt thereof.

In one aspect, the present invention relates to a pharmaceutical composition comprising a compound selected from formulae AD, AE, and AF:

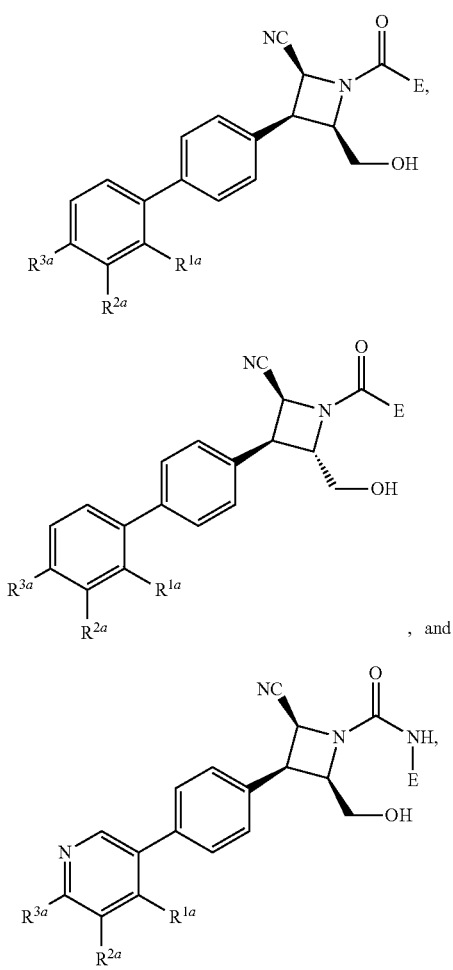

or a pharmaceutically acceptable salt thereof.

In one aspect, the present invention relates to a pharmaceutical composition comprising a compound of formula AA, AB, AC, AD, AE, and AF, wherein $R^{1a}$ is hydrogen or fluoro. In one aspect, $R^{1a}$ is hydrogen. In one aspect, $R^{1a}$ is fluoro. In one aspect, $R^{2a}$ is hydrogen or fluoro. In one aspect, $R^{2a}$ is hydrogen. In one aspect, $R^{2a}$ is fluoro.

In one aspect, the present invention relates to a pharmaceutical composition comprising a compound of formula AG

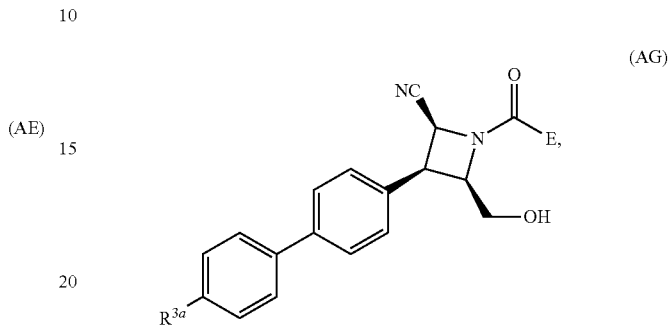

or pharmaceutically acceptable salt thereof.

In one aspect, the present invention relates to a pharmaceutical composition comprising a compound of formula AA, AB, AC, AD, AE, AF, and AG, wherein $R^{3a}$ is hydrogen or $C(O)N(C_1\text{-}C_8\ \text{alkyl})_2$. In one aspect, $R^{3a}$ is $C(O)N(CH_3)_2$.

In one aspect, the present invention relates to a pharmaceutical composition comprising a compound of formula AA, AB, AC, AD, AE, AF, and AG, E is $C_1$-$C_6$ alkyl, 6 membered heterocyclic ring, or $C_4$-$C_6$ cycloalkyl ring. In one aspect, wherein E is cyclobutyl, cyclopentyl, or cyclohexyl. In one aspect, E is n-propyl. In one aspect, E is pyridinyl.

The invention relates to a compound in Table A or a pharmaceutically acceptable salt or solvate thereof.

TABLE A

| MS Data | Compound no. | Structure |
|---|---|---|
| Exact Mass: 618.27, MS Found [M + H]⁺: 619.01 | 1a | |
| Exact Mass: 607.23 MS Found [M + H]⁺: 608.53 | 2a | |

TABLE A-continued

| MS Data | Compound no. | Structure |
|---|---|---|
| Exact Mass: 594.25, MS Found [M + H]⁺: 595.35 | 3a | |
| Exact Mass: 609.23, MS Found [M + H]⁺: 610.19 | 4a | |
| Exact Mass: 542.28, MS Found [M + H]⁺: 543.18 | 5a | |
| Exact Mass: 542.28, MS Found [M + H]⁺: 543.46 | 6a | |

TABLE A-continued
| MS Data | Compound no. | Structure |
|---|---|---|
| Exact Mass: 542.28, MS Found [M + H]+: 543.63. | 7a | 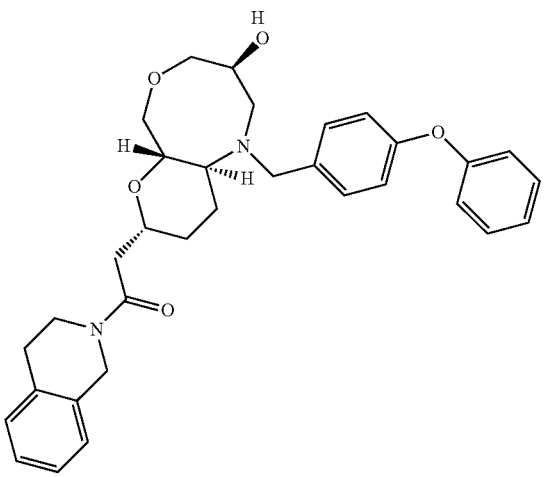 |
| Exact Mass: 522.23, MS Found [M + H]+: 523.57. | 8a | 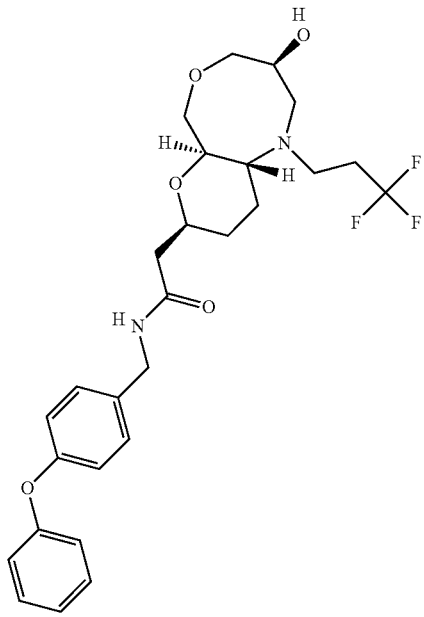 |
| Exact Mass: 542.28, MS Found [M + H]+: 543.45. | 9a | 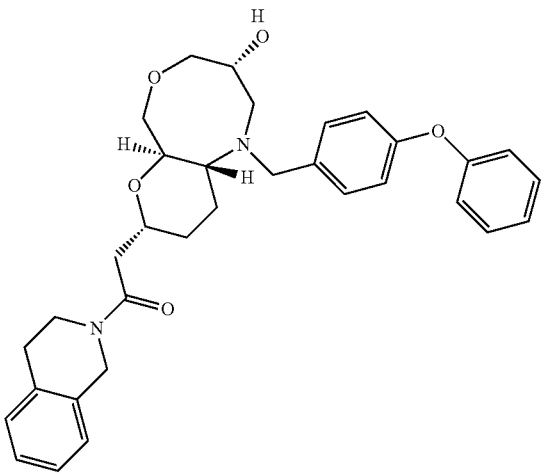 |

TABLE A-continued

| MS Data | Compound no. | Structure |
|---|---|---|
| Exact Mass: 522.23, MS Found [M + H]⁺: 523.15. | 10a | |
| Exact Mass: 608.22, MS Found [M + H]⁺: 609.52 | 11a | |
| Exact Mass: 488.23, MS Found [M + H]⁺: 489.51. | 12a | |

TABLE A-continued

| MS Data | Compound no. | Structure |
|---|---|---|
| Exact Mass: 618.18, MS Found [M + H]+: 619.53 | 13a | 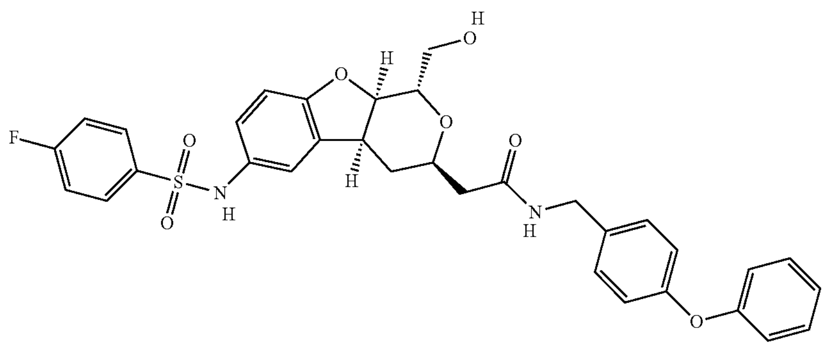 |
| Exact Mass: 607.23 MS Found [M + H]+: 608.18 | 14a | Chiral |
| MS calculated: 622.26 Found [M + H]+: 623.35 | 15a | Chiral |

TABLE A-continued
| MS Data | Compound no. | Structure |
|---|---|---|
| MS calculated: 507.24 Found [M + H]+: 508.14 | 16a | Chiral  |
| | 17a | 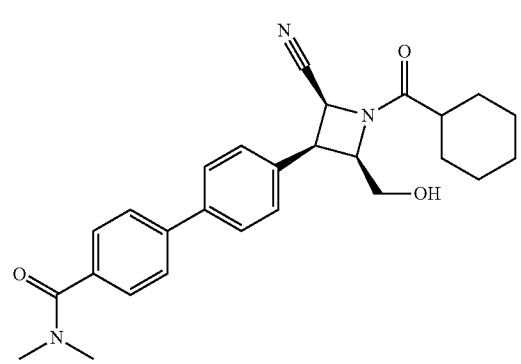 [SMILES: CN(C)C(=O)c1ccc(-c2ccc([C@H]3[C@@H](C#N)N(C(=O)C4CCCCC4)[C@H]3CO)cc2)cc1] |
| | 18a | 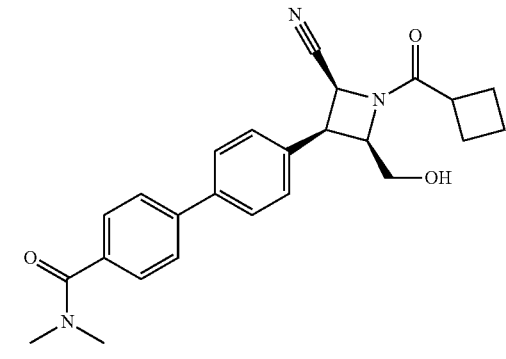 [SMILES: CN(C)C(=O)c1ccc(-c2ccc([C@H]3[C@@H](C#N)N(C(=O)C4CCC4)[C@H]3CO)cc2)cc1] |
| | 19a | 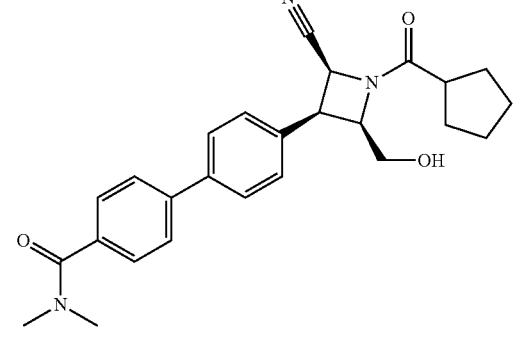 |

TABLE A-continued

| MS Data | Compound no. | Structure |
|---|---|---|
| | 20a | |
| | 21a | |
| | 22a | |
| | 23a | |
| | 24a | |

MS Found data determined using a single quadrupole mass spectrometer.

The invention relates to a compound of the invention or a pharmaceutically acceptable salt, solvate, or prodrug thereof. In one aspect, the invention relates to a compound of the invention or a pharmaceutically acceptable salt. In one aspect, the invention relates to a compound of the invention or a pharmaceutically acceptable salt or solvate thereof. In one aspect, the invention relates to a pharmaceutically acceptable salt of a compound of the invention. In one aspect, the invention relates to a solvate of a compound of the invention. In one aspect, the invention relates to a hydrate of a compound of the invention. In one aspect, the invention relates to a prodrug of a compound of the invention.

The invention relates to methods of synthesizing a compound of the invention. A compound of the invention can be synthesized using a variety of methods known in the art. The schemes and description below depict general routes for the preparation of a compound of the invention. The preparation of starting material A is described in J. Org. Chem. 2011, 76, 1898-1901.

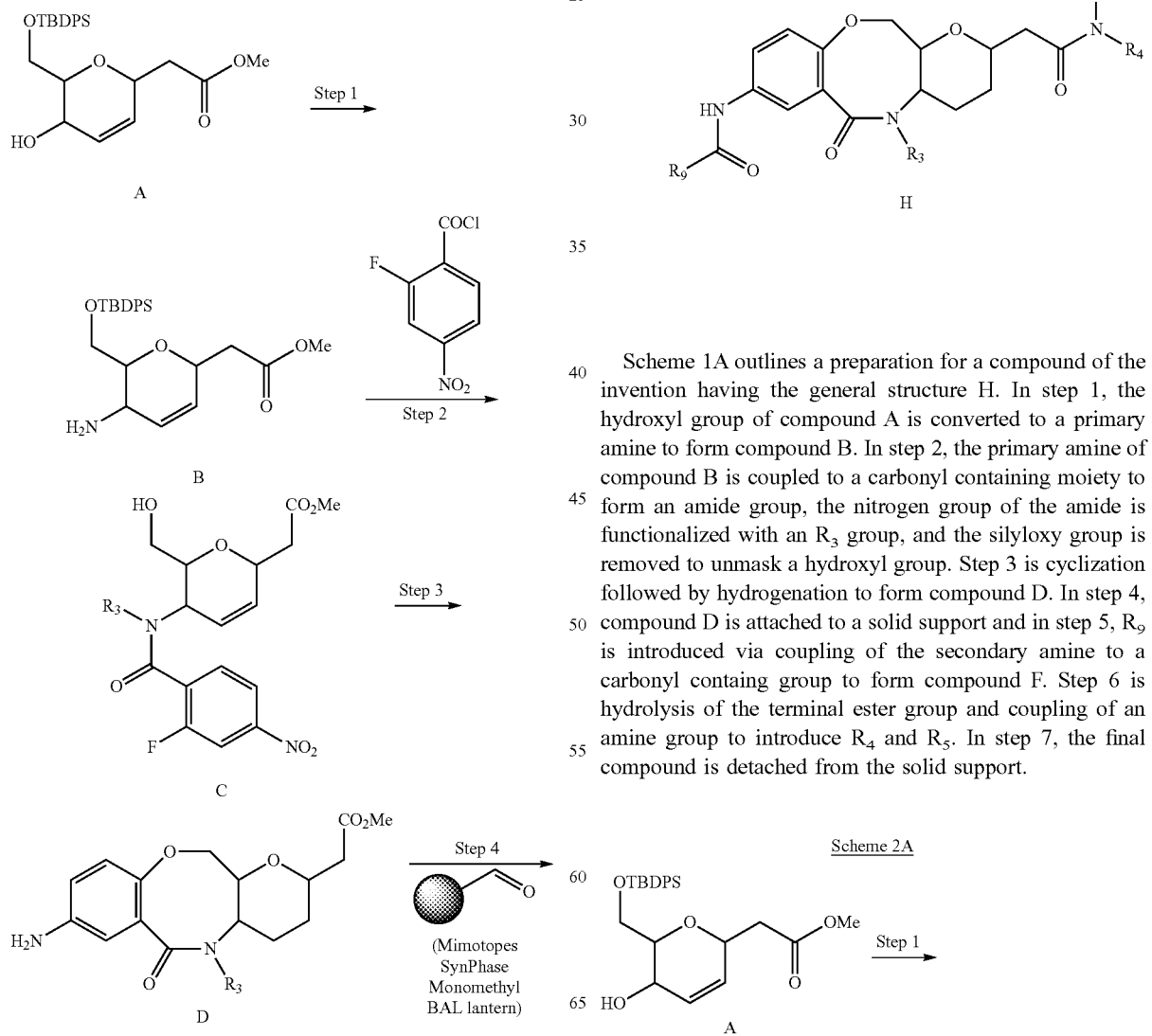

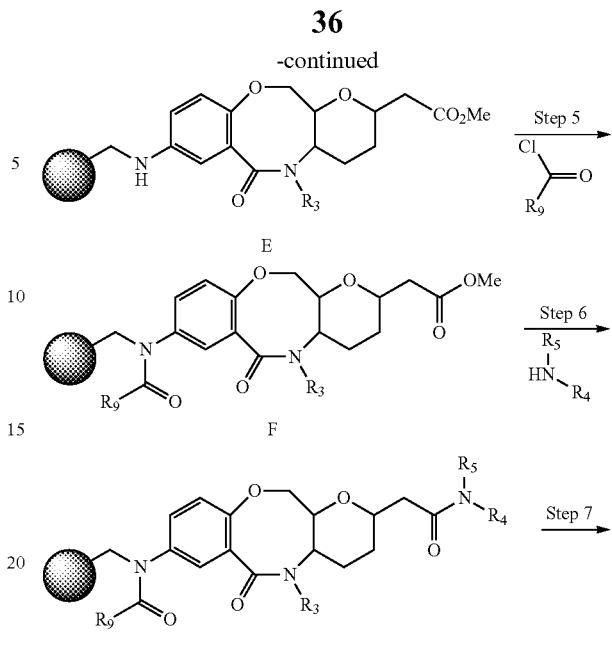

Scheme 1A outlines a preparation for a compound of the invention having the general structure H. In step 1, the hydroxyl group of compound A is converted to a primary amine to form compound B. In step 2, the primary amine of compound B is coupled to a carbonyl containing moiety to form an amide group, the nitrogen group of the amide is functionalized with an $R_3$ group, and the silyloxy group is removed to unmask a hydroxyl group. Step 3 is cyclization followed by hydrogenation to form compound D. In step 4, compound D is attached to a solid support and in step 5, $R_9$ is introduced via coupling of the secondary amine to a carbonyl containg group to form compound F. Step 6 is hydrolysis of the terminal ester group and coupling of an amine group to introduce $R_4$ and $R_5$. In step 7, the final compound is detached from the solid support.

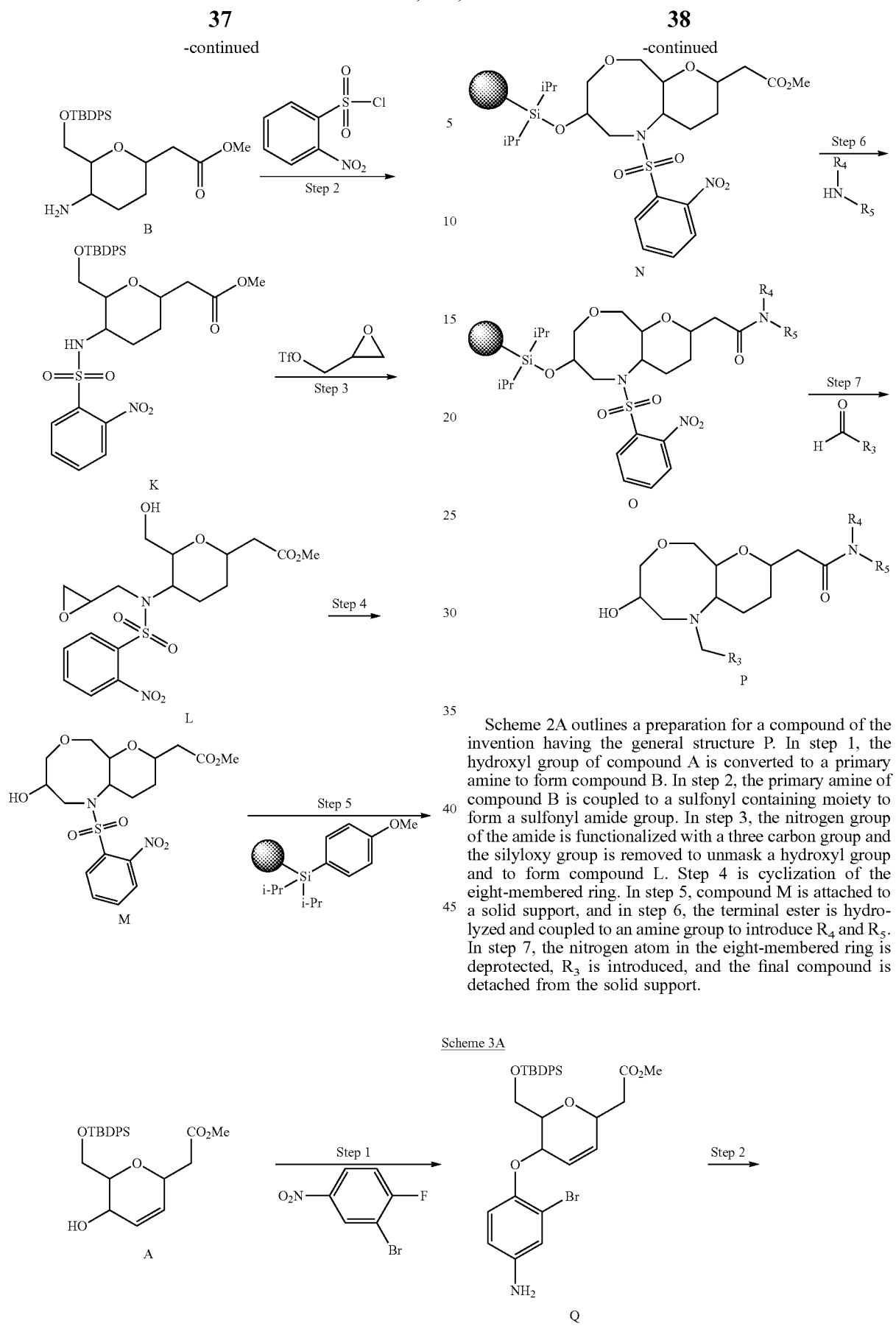

Scheme 2A outlines a preparation for a compound of the invention having the general structure P. In step 1, the hydroxyl group of compound A is converted to a primary amine to form compound B. In step 2, the primary amine of compound B is coupled to a sulfonyl containing moiety to form a sulfonyl amide group. In step 3, the nitrogen group of the amide is functionalized with a three carbon group and the silyloxy group is removed to unmask a hydroxyl group and to form compound L. Step 4 is cyclization of the eight-membered ring. In step 5, compound M is attached to a solid support, and in step 6, the terminal ester is hydrolyzed and coupled to an amine group to introduce $R_4$ and $R_5$. In step 7, the nitrogen atom in the eight-membered ring is deprotected, $R_3$ is introduced, and the final compound is detached from the solid support.

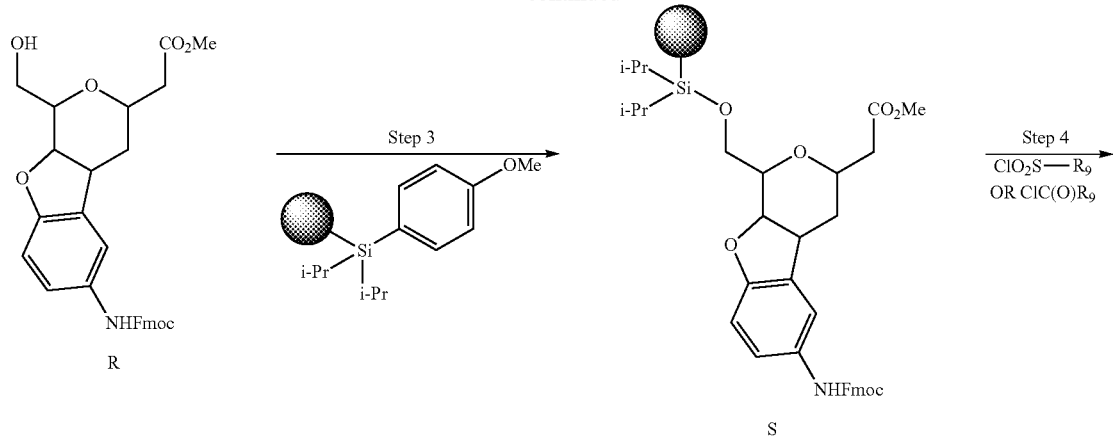

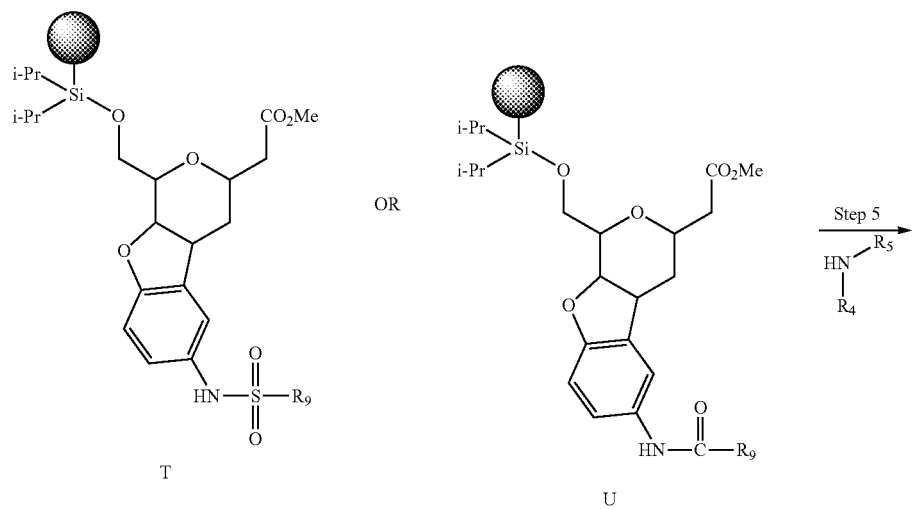

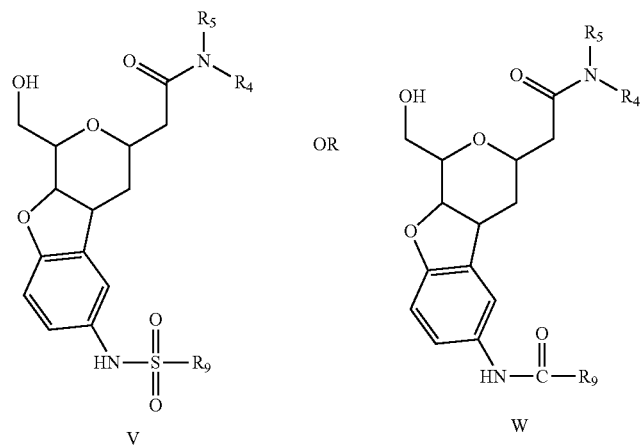

Scheme 3A outlines a preparation for a compound of the invention having the general structure V or W. In step 1, the hydroxyl group of compound A is converted to a phenoxy group to form compound Q. In step 2, the central 5-membered ring is formed. In step 3, compound R is attached to the solid support. In step 4, the aryl amine group is deprotected and the $R_9$ group is introduced via a sulfonyl linker to form compound T (or alternatively the $R_9$ group is introduced via a carbonyl linker to form compound U). In step 5, the terminal ester is hydrolyzed and coupled to an amine group to introduce $R_4$ and $R_5$ and the final compound is detached from the solid support to produce compound V (or alternatively compound W).

Scheme 4A

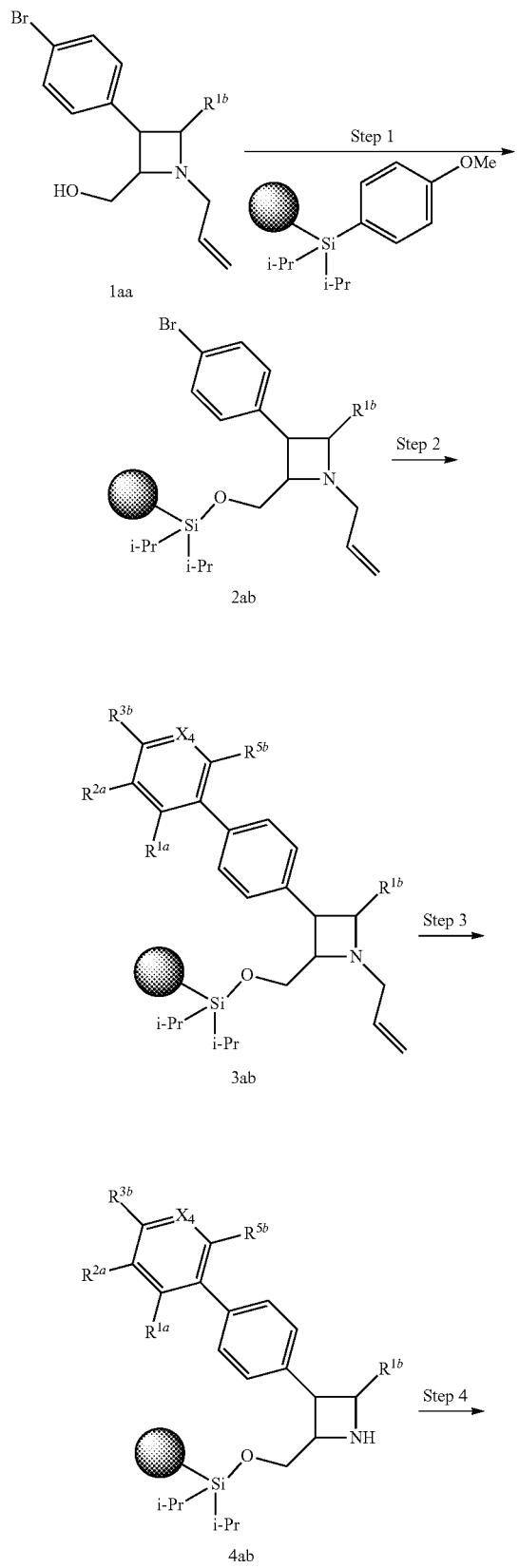

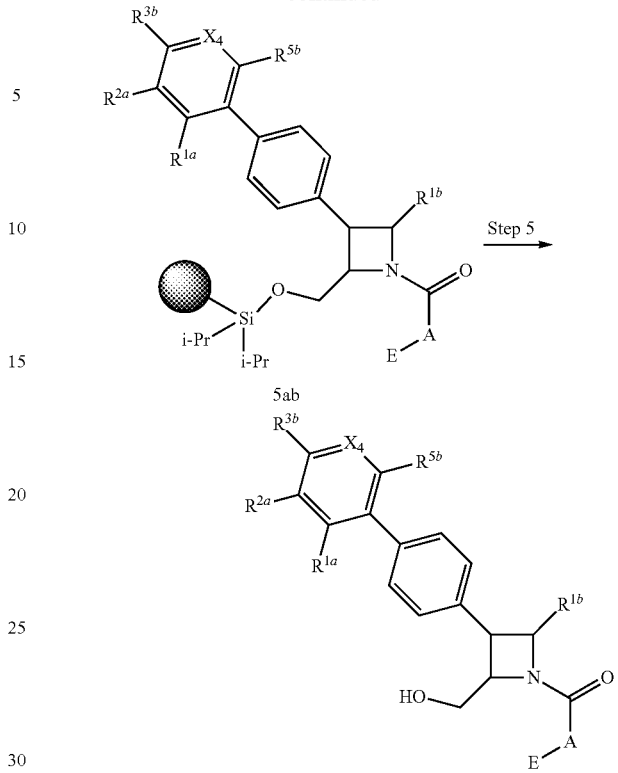

Scheme 4A outlines a preparation for a compound of the invention having the general structure AA. Compound 1aa can be prepared according to methods known in the art. For example, compound 1aa can be prepared according to Lowe et al Journal of Organic Chemistry, 2012, 77, 7187 (e.g., Scheme 1, and Scheme 5 provides procedures to remove the protecting group and derivatize with substituents on the azetidine nitrogen). In step 1 compound 1aa is attached to a solid support. In step 2, the aryl bromide is coupled with aromatic boronic acids to form compound 3a. In step 3 the allyl group is removed to form compound 4a. In step 4, the C(O)EA moiety is introduced via coupling of the secondary amine to acids and isocyanates to form compound 5a. In step 5, the final compound is detached from the solid support.

The invention relates to a medical device containing a compound of the invention or a pharmaceutically acceptable salt or solvate thereof.

Modulation of TRIB1 and Other Key Regulators in Lipoprotein Metabolism

Recent genome-wide association (GWAS) studies have uncovered novel genes associated with CAD and MI. TRIB1 emerged in several GWAS studies as a novel cardiovascular locus where the protective allele is strongly associated with decreased levels of circulating LDL-C and triglycerides (TG), increased levels of high-density lipoprotein (HDL) as well as with reduced incidence of CAD and MI (T. M. Teslovich et al., Nature 466, 707 (Aug. 5, 2010)). Additional studies in mice confirmed the link between TRIB1 and lipid levels and demonstrated that increased expression of TRIB1 is protective against the disease (R. Burkhardt et al., *J Clin Invest* 120, 4410 (December, 2010)). Hepatic overexpression of TRIB1 in mice reduces the secretion of VLDL particles from the liver into the bloodstream and consistently, overexpression of TRIB1 in human hepatoma cells reduces apoB secretion. The precise molecular mechanism by which overexpression of TRIB1 regulates the rate of VLDL particle formation and secretion is not known although hepatic overexpression of TRIB1 in mice correlates with decreased expression of TG biosynthetic genes (Fasn, Scd1, Dgat2) and decreased rate of TG formation suggesting that reduced availability of TG's leads to insufficient apoB lipidation targeting nascent apoB to ER-associated degradation (R. Burkhardt et al., 2010)). TRIB1, as other members of tribbles family, is a pseudokinase and it is thought to act as an adaptor protein in the MEK/ERK signaling pathway. It has been reported to be involved in inflammation (T. Yokoyama, T. Nakamura, Cancer Sci 102, 1115 (June, 2011)), however prior to cardiovascular GWAS studies it was not known to modulate hepatic lipoprotein metabolism (E. Kiss-Toth, Biochem Soc Trans 39, 684 (April, 2011)).

Compounds of the invention are inducers or upregulators of TRIB1 expression. As a result, these compounds are useful in treating and/or preventing various diseases, disorders and conditions of the cardiovascular system, including e.g., myocardial infarction, coronary heart disease, atherosclerosis and dyslipidemia. The compounds of the invention are useful in treating and/or preventing various diseases, disorders and conditions of the liver, including e.g., cirrhosis and liver cancer. The compounds of the invention are useful in treating and/or preventing various diseases, disorders and conditions that will benefit from higher expression of TRIB1 and/or higher expression levels of LDLR and/or lower expression levels of PCSK9 and/or lower expression levels of MTTP and/or lower expression levels of APOC3.

In one aspect, the invention provides a method of increasing the uptake of LDL in a cell, the method comprising contacting a cell or a population of cells with a compound of the invention or a pharmaceutically acceptable salt or solvate thereof with an amount sufficient to increase the uptake of LDL as compared to the LDL of the cell or population of cells in the absence of the compound or pharmaceutically acceptable salt or solvate thereof. In one aspect, the uptake of LDL is increased by at least about 1.5-fold, 2-fold, 3-fold, 5-fold, 10-fold, 15-fold, 20-fold or 30-fold. In one aspect, the type of cell or population of cells is selected from heptic, skin, adrenal gland, muscle, or kidney cell. In one aspect, the type of cell is HepG2 cell. In one aspect, the compound of the invention thereof modulates the expression of one or more genes or one or more products of one or more genes selected from TRIB1, SCAP, SREBF1, SREBF2, PCSK9, LDLR, HMGCR, HMGCS, FASN, SCD1, MTTP and APOC3. The number of genes or products of genes modulated is 1, 2, 3, 4, 5, 6, 7, 8, 9, 10, 11, or 12.

In one aspect, the compound of the invention increases the expression of TRIB1. In one aspect, the compound of the invention increases the expression of TRIB1 and decreases the expression of PCSK9. In one aspect, the compound of the invention increases the expression of TRIB1 and LDLR and decreases the expression of PCSK9, MTTP and APOC3. In one aspect, the compound of the invention decreases expression of one or more genes selected from HMGCR, HMGCS, FASN, SREBF1, and SCD1. The number of genes is 1, 2, 3, 4, or 5. In one aspect, the compound of the invention does not change the expression of one or more genes selected from SCAP or SREBF2. The number of genes is 1 or 2. In one aspect, the compound of the invention modulates the protein expression level of a protein selected from ApoB and LDLR.

In one aspect, the invention provides a method of increasing the LDL receptor level on a cell, the method comprising contacting a cell or a population cells with a compound of the invention with an amount sufficient to increase LDL receptor level as compared to the LDL receptor level of the cell or population of cells in the absence of the compound. In one aspect, the uptake of LDL is increased by least 1.5-fold, 2-fold, 3-fold, 5-fold, 10-fold, 15-fold, 20-fold or 30-fold. In one aspect, the type of cell or population of cells is selected from heptic, skin, adrenal gland, muscle, or kidney cell. In one aspect, the type of cell is HepG2 cell. In aspect, the compound of the invention modulates the expression of one or more genes or one or more products of one or more genes selected from TRIB1, SCAP, SREBF1, SREBF2, PCSK9, LDLR, HMGCR, HMGCS, FASN, SCD1, MTTP and APOC3. The number of genes or products of genes is 1, 2, 3, 4, 5, 6, 7, 8, 9, 10, 11, or 12.

In one aspect, the compound of the invention increases the expression of TRIB1. In one aspect, the compound of the invention increases the expression of TRIB1 and decreases the expression of PCSK9. In one aspect, the compound of the invention increases the expression of TRIB1 and LDLR and decreases the expression PCSK9, MTTP and APOC3. In one aspect, the compound of the invention decreases expression of one or more genes selected from HMGCR, HMGCS, FASN, SREBF1 and SCD1. The number of genes is 1, 2, 3, 4, or 5. In one aspect, the compound of the invention does not change the expression of one or more genes selected from SCAP or SREBF2. The number of genes is 1 or 2. In one aspect, the compound of the invention thereof modulates the protein expression level of a protein selected from ApoB and LDLR.

The invention provides methods of treating or preventing a disease, disorder, or condition. In one aspect, the invention provides a method of treating a disease, disorder, or condition. In one aspect, the invention provides a method of preventing a disease, disorder, or condition.

In one aspect, the invention provides a method of treating or preventing a disease, disorder, or condition associated with elevated LDL-cholesterol in a subject in need thereof comprising administering to the subject an effective amount of a compound of the invention or a pharmaceutically acceptable salt or solvate thereof.

In one aspect, the invention provides a method of treating or preventing a lipoprotein related disorder (e.g., cholesterol related disorder) in a subject in need thereof comprising administering to the subject an effective amount of a compound of the invention or a pharmaceutically acceptable salt or solvate thereof. In one aspect, the lipoprotein related disorder (e.g., cholesterol related disorder) is any disorder that is characterized by decreased levels of TRIB1 in the subject. In one aspect, the lipoprotein related disorder (e.g., cholesterol related disorder) is any disorder that can be treated by increasing expression levels of TRIB1 in a subject in need of treatment. In one aspect, the lipoprotein related disorder (e.g., cholesterol related disorder) is any disorder that can be prevented by increasing expression levels of TRIB1 in a subject in need of prevention.

In one aspect, the invention provides a method of increasing availability of LDLR in a subject comprising administering to the subject an effective amount of a compound of the invention or a pharmaceutically acceptable salt or solvate thereof.

In one aspect, the invention provides a method of reducing LDL-cholesterol level in a subject comprising administering to the subject an effective amount of a compound of the invention or a pharmaceutically acceptable salt or solvate thereof.

In one aspect, the invention provides a method of lowering serum LDL-cholesterol level in a subject comprising administering to the subject an effective amount of a compound of the invention or a pharmaceutically acceptable salt or solvate thereof.

In one aspect, the invention provides a method of treating or preventing a disease in a subject in need thereof comprising administering to the subject an effective amount of a compound of the invention or a pharmaceutically acceptable salt or solvate thereof, wherein said compound increases LDL uptake.

In one aspect, the invention provides a method of treating or preventing diseases, conditions, or disorders in a subject in need thereof, where said diseases, conditions, or disorders are generally addressable through the use of statins.

In one aspect, the invention provides a method of treating or preventing cardiovascular disease in a subject in need thereof comprising administering to the subject an effective amount of a compound of the invention or a pharmaceutically acceptable salt or solvate thereof. In one aspect, the cardiovascular disease is myocardial infarction, coronary heart disease, atherosclerosis or hypocholesterolemia. In one aspect, the cardiovascular disease is any cardiovascular disease that is characterized by decreased levels of TRIB1 in the subject. In one aspect, the cardiovascular disease is any cardiovascular disease that can be treated by increasing expression levels of TRIB1 in a subject in need of treatment. In one aspect, the cardiovascular disease is any cardiovascular disease that can be prevented by increasing expression levels of TRIB1 in a subject in need of prevention.

In one aspect, the invention provides a method of treating hypercholesterolemia in a subject, comprising administering to the subject an effective amount of a compound of the invention or a pharmaceutically acceptable salt or solvate thereof.

In one aspect, the invention provides a method of treating or preventing a liver disease or disorder in a subject in need thereof comprising administering to the subject an effective amount of a compound of the invention or a pharmaceutically acceptable salt or solvate thereof. In one aspect, the liver disease or disorder is liver cirrhosis, hepatocellular carcinoma, liver injury or abnormal liver function.

In one aspect, the invention provides a method of treating or preventing a disease in a subject in need thereof comprising administering to the subject an effective amount of a compound of the invention or a pharmaceutically acceptable salt or solvate thereof, wherein said compound down regulates the expression level of PCSK9, MTTP and APOC3 and up regulates expression level of TRIB1 and LDLR. In one aspect, the disease is a lipoprotein related disorder (e.g., cholesterol related disorder). In one aspect, the disease is a cardiovascular disease or a liver disease or disorder. In one aspect, the subject is at an elevated risk for cardiovascular disease. In one aspect, the expression level of PCSK9 is down regulated by at least about 50%. In one aspect, the expression level of TRIB1 is up regulated by at least about 50%.

Modulation of TRIB1

TRIB1 (tribbles homolog 1, TRB1) is a regulator of lipoprotein metabolism. Recent genome-wide association studies identified TRIB1 as having minor alleles associated with lower levels of plasma triglyceride and LDL-C (low density lipoprotein cholesterol), higher levels of HDL-C (high density lipoprotein-C), as well as significantly decreased risk for myocardial infarction and coronary heart disease (T. M. Teslovich et al., Nature 466, 707 (Aug. 5, 2010)). TRIB1 is highly expressed in the liver, which is the major site for the formation, secretion, and clearance of circulating lipoproteins. Overexpression of TRIB1 in mouse models causes significant reduction of VLDL (very low density lipoprotein), LDL, and HDL cholesterol and triglycerides (R. Burkhardt et al., J Clin Invest 120, 4410 (December, 2010)). In one aspect, a compound of the invention modulates or upregulates TRIB1 for treating and/or a preventing cardiovascular disease (e.g., myocardial infarction, coronary heart disease, atherosclerosis, or dyslipidemia).

TRIB1 alleles have also been shown to be associated with concentrations of liver enzymes (J. C. Chambers et al., Nat Genet 43, 1131 (November, 2011)). High liver enzyme concentrations are associated with increased risk of cirrhosis, hepatocellular carcinoma, liver injury (e.g., alcohol misuse, viral and other infections, metabolic disorders, obesity, autoimmune disease, and drug toxicity), and abnormal liver function (D. S. Pratt, M. M. Kaplan, N Engl J Med 342, 1266 (Apr. 27, 2000)). In one aspect, a compound of the invention is useful for treating and/or preventing liver diseases (e.g., cirrhosis or liver cancer).

In one aspect, a compound of the present invention increases the expression levels of TRIB1. In one aspect, the protein expression level of TRIB1 is increased. In one aspect, the RNA transcript level is increased. In one aspect, a compound of the invention increases TRIB1 expression by at least about 50%. In one aspect, a compound of the invention increases TRIB1 expression by at least 1.5-fold, 2-fold, 3-fold, 4-fold, 5-fold, 10-fold, 15-fold, or 20-fold.

In one aspect, a compound of the invention is useful for diseases that are associated with decreased levels of TRIB1 in a subject. In one aspect, a compound of the invention is useful for diseases that are treated or prevented by increasing levels of TRIB1 in a subject. In one aspect, a compound of the invention also decreases the expression of PCSK9.

In one aspect, a compound of the invention also increases the expression of LDLR (low density lipoprotein receptor). In one aspect, expression or expression levels refers to protein expression and/or gene expression (e.g., RNA).

In one aspect, a compound of the invention stimulates a unique signature of cellular responses, without affecting cellular ATP levels or cell viability. This unique signature of cellular responses comprises: 1) upregulation of transcript levels for TRIB1; 2) downregulation of transcript levels for PCSK9; or 3) up regulation of transcript levels for LDLR. The unique signature of cellular responses may further comprise any one or more of the following: 1) downregulation of transcript levels for genes in the cholesterol biosynthetic pathway (e.g., HMGCS, HMGCR); 2) downregulation of transcript levels for genes in the triglyceride biosynthetic pathway (e.g., FASN, SCD1); 3) down regulation of transcript levels of a gene for microsomal triglyceride transfer protein (MTTP) important for the lipidation of the ApoB 4) down regulation of transcript levels of a gene for apolipoprotein C3 that up regulates triglyceride levels (APOC3) 5) decreased level of secreted ApoB 100 protein; 6) decreased level of secreted PCSK9 protein; or 7) increased level of LDLR in cells. Each of the responses listed above has individually been linked to the reduction of LDL-C and/or TG in circulation.

The transcriptional profile produced by a compound of the invention is markedly different from the transcriptional profile produced by statin treatment. In addition to TRIB1 upregulation, treatment with a compound of the invention also modulates the expression of one or more genes involved in sterol regulatory pathways. In one aspect, a compound of the invention up regulates the expression of LDLR and down regulates the expression of PCKS9, HMGCS, HMGCR, FASN, SCD1, MTTP and APOC3. In contrast, treatment with a statin, such as atorvastatin, up regulates the expression of PCSK9, as well as LDLR, HMGCS and HMGCR. In one aspect, downregulation of PCKS9 is indicative or confers additional therapeutic benefits of treatment with a compound of the invention. Differences in pharmacological mode of action between a compound of the invention and statins suggest different efficacies in treating and preventing cardiovascular diseases and related disorders. Downregulation of PSCK9 expression with a compound of the invention may provide therapeutic benefit similar to treatments with anti-PCSK9 monoclonal antibodies or other biologic PSCK9 blockers but will differ from anti-PCSK9 biologics in the route of administration and offer a convenience and the ease of use of an oral drug versus intravenous therapy.

In one aspect, the invention provides a method of assessing the efficacy of a therapeutic agent for treating a disease in a subject comprising: (a) administering the therapeutic agent to the subject; (b) determining a first level of expression of one or more signature genes or one or more products of one or more signature genes in a sample from the subject at a first time point; and (c) comparing the first level of expression of one or more signature genes or one or more products of one or more signature genes at the first time point to a reference profile; wherein the difference in the level of expression at the first time point as compared to the level of expression of the reference profile indicates that the therapeutic agent is effective for treating the disease. In one aspect, the one or more signature genes are selected from TRIB1, SCAP, SREBF1, SREBF2, PCSK9, LDLR, HMGCR, HMGCS, FASN, SCD1, MTTP and APOC3. In one aspect, the number of signature genes is 1, 2, 3, 4, 5, 6, 7, 8, 9, 10, 11, or 12. In one aspect, the disease is associated with decreased expression of TRIB1. In one aspect, determining the expression level is determining the level of protein or RNA transcripts. In one aspect, the reference profile is obtained from a subject that does not have the disease. In one aspect, the reference profile is obtained from the subject at a time point prior to administering the therapeutic agent. In one aspect, the disease is a lipoprotein (e.g., cholesterol) related disorder. In one aspect, the disease is a cardiovascular disease. In one aspect, the therapeutic agent is a compound of the invention.

In one aspect, the invention provides a method of assessing the efficacy of a therapeutic agent for treating a disease in a subject comprising: (a) administering the therapeutic agent to the subject; (b) determining the expression level of TRIB1 in a sample from the subject at a first time point; and (c) comparing the expression level of TRIB1 at the first time point to a reference profile, wherein an increase in TRIB1 expression compared to the reference profile indicates that the therapeutic agent is effective for treating the disease.

In one aspect, the invention provides a method of accessing the efficacy of a therapeutic agent for treating a disease in a subject comprising: (a) administering the therapeutic agent to the subject; (b) determining the expression level of PCKS9 in a sample from the subject at a first time point; and (c) comparing the expression level of PCKS9 at a first time point to a reference profile, wherein a decrease in the level of PCKS9 expression at the first time point as compared to the reference profile indicates that the therapeutic agent is effective for treating the disease.

In one aspect, the invention provides a method of assessing the efficacy of a therapeutic agent for treating a disease in a subject comprising: (a) administering the therapeutic agent to the subject; (b) determining the expression level of TRIB1 and PCSK9 in a sample from the subject at a first time point; and (c) comparing the expression level of TRIB1 and PCSK9 at a first time point to a reference profile; wherein an increase in TRIB1 expression and a decrease in PCKS9 expression compared to the reference profile indicates that the therapeutic agent is effective for treating the disease. In one aspect, the disease is associated with decreased expression of TRIB1. In one aspect, the invention provides a method, wherein determining the expression level is determining the level of protein or RNA transcripts.

In one aspect, the invention provides a method of assessing the efficacy of a therapeutic agent related to determining the expression level of TRIB1 and/or PCSK9, wherein the reference profile is obtained from a subject that does not have the disease. In one aspect, the reference profile is obtained from the subject a time point prior to administering the therapeutic agent.

In one aspect, the expression level of TRIB1 at the first time point is up regulated by at least about 50%. In one aspect, the expression level of TRIB1 at the first time point is increased by at least about 1.5-fold, 2-fold, 3-fold, 4-fold, 5-fold, 10-fold, 15-fold, or 20-fold. In one aspect, the invention provides a method, wherein said expression level of PCSK9 is down regulated by at least about 50%. In one aspect, the expression level of PCSK9 is decreased by at least about 2-fold, 3-fold, 4-fold, 5-fold, 10-fold, 15-fold, or 20-fold. In one aspect, the therapeutic agent is a compound of the invention. In one aspect, the disease is a lipoprotein related disorder (e.g., cholesterol related disorder). In one aspect, the disease is a cardiovascular disease.

In one aspect, the invention provides a method of assessing the efficacy of a therapeutic agent for treating a disease in a subject comprising: (a) administering a therapeutic agent to the subject; (b) determining the protein expression level of ApoB in a sample from the subject at a first time point; and (c) comparing the protein expression level of ApoB at the first time point to a reference profile; wherein a decrease in expression of ApoB at the first time point compared to the reference profile indicates that the therapeutic agent is effective for treating the disease. In one aspect, the reference profile is obtained from a subject that does not have the disease. In one aspect, the reference profile is obtained from the subject a time point prior to administering the therapeutic agent. In one aspect, the protein expression level of ApoB at the first time point is down regulated by at least about 50%. In one aspect, the expression of ApoB is increased by at least about 1.5-fold, 2-fold, 3-fold, 4-fold, 5-fold, 10-fold, 15-fold, or 20-fold. In one aspect, the therapeutic agent is a compound of the invention. In one aspect, the disease is a lipoprotein related disorder (e.g., cholesterol related disorder). In one aspect, the disease is a cardiovascular disease.

In one aspect, the invention provides a method of assessing the efficacy of a therapeutic agent for treating a disease in a subject comprising: (a) administering a therapeutic agent to the subject; (b) determining the protein expression level of LDLR in a sample from the subject at a first time point; and (c) comparing the protein expression level of LDLR at the first time point to a reference profile; wherein an increase in expression of LDLR at the first time point compared to the reference profile indicates that the therapeutic agent is effective for treating the disease. In one aspect, the reference profile is obtained from the subject prior to administering the therapeutic agent. In one aspect, the protein expression level of LDLR at the first time point is up regulated by at least about 50%. In one aspect, the expression of LDLR is increased by at least about 1.5-fold, 2-fold, 3-fold, 4-fold, 5-fold, 10-fold, 15-fold, or 20-fold. In one aspect, the therapeutic agent is a compound of the invention. In one aspect, the disease is a lipoprotein related disorder (e.g., cholesterol related disorder). In one aspect, the disease is a cardiovascular disease.

In one aspect, the invention provides a method of assessing the efficacy of a therapeutic agent for treating a disease in a subject comprising: (a) administering the therapeutic agent to the subject; (b) determining the RNA transcript level of SREBF1 in a sample from the subject at a first time point; and (c) comparing the RNA transcript level of SREBF1 at the first time point to a reference profile; wherein a decrease in expression of SREBF1 at the first time point compared to the reference profile indicates that the therapeutic agent is effective for treating the disease. In one aspect, the RNA transcript level of SREBF1 in the sample from the subject is down regulated by 1-2 fold. In one aspect, the reference profile is obtained from the subject prior to administering the therapeutic agent. In one aspect, the therapeutic agent is a compound of the invention. In one aspect, the disease is a lipoprotein (e.g., cholesterol related disorder). In one aspect, the disease is a cardiovascular disease.

In one aspect, the invention provides a method of assessing the efficacy of a therapeutic agent for treating a disease in a subject comprising: (a) administering the therapeutic agent to the subject; (b) determining the RNA transcript level of HMGCR in a sample from the subject at a first time point; and (c) comparing the RNA transcript level of HMGCR at the first time point to a reference profile; wherein a decrease in expression of HMGCR at the first time point compared to the reference profile indicates that the therapeutic agent is effective for treating the disease. In one aspect, the RNA transcript level of HMGCR in the sample from the subject is down regulated by at least about 50%. In one aspect, the expression of HMGCR is decreased by at least about 2-fold, 3-fold, 4-fold, 5-fold, 10-fold, 15-fold, or 20-fold. In one aspect, the reference profile is obtained from the subject prior to administering the therapeutic agent. In one aspect, the therapeutic agent is a compound of the invention. In one aspect, the disease is a lipoprotein related disorder (e.g., cholesterol related disorder). In one aspect, the disease is a cardiovascular disease.

In one aspect, the invention provides a method of assessing the efficacy of a therapeutic agent for treating a disease in a subject comprising: (a) administering a therapeutic agent to the subject; (b) determining the RNA transcript level of HMGCS in a sample from the subject at a first time point; and (c) comparing the RNA transcript level of HMGCS at the first time point to a reference profile; wherein a decrease in the RNA transcript level of HMGCS at the first time point compared to the reference profile indicates that the therapeutic agent is effective for treating the disease. In one aspect, the RNA transcript level of HMGCS in the sample from the subject is down regulated by at least about 50%. In one aspect, the RNA transcript level of HMGCS is decreased by at least about 2-fold, 3-fold, 4-fold, 5-fold, 10-fold, 15-fold, or 20-fold. In one aspect, the reference profile is obtained from the subject prior to administering the therapeutic agent. In one aspect, the therapeutic agent is a compound of the invention. In one aspect, the disease is a lipoprotein related disorder. In one aspect, the disease is a cholesterol related disorder. In one aspect, the disease is a cardiovascular disease.

In one aspect, the invention provides a method of assessing the efficacy of a therapeutic agent for treating a disease in a subject comprising: (a) administering the therapeutic agent to the subject; (b) determining the RNA transcript level of FASN in a sample from the subject at a first time point; and (c) comparing the RNA transcript level of FASN at the first time point to a reference profile; wherein a decrease in RNA transcript level at the first time point compared to the reference profile indicates that the therapeutic agent is effective for treating the disease. In one aspect, the RNA transcript level of FASN in the sample from the subject is down regulated by at least about 50%. In one aspect, the RNA transcript level of FASN is decreased by at least about 2-fold, 3-fold, 4-fold, 5-fold, 10-fold, 15-fold, or 20-fold. In one aspect, the reference profile is obtained from the subject prior to administering the therapeutic agent. In one aspect, the therapeutic agent is a compound of the invention. In one aspect, the disease is a lipoprotein related disorder. In one aspect, the disease is a cholesterol related disorder. In one aspect, the disease is a cardiovascular disease.

In one aspect, the invention provides a method of assessing the efficacy of a therapeutic agent for treating a disease in a subject comprising: (a) administering the therapeutic agent to the subject; (b) determining the RNA transcript level of SCD1 in a sample from the subject at a first time point; and (c) comparing the RNA transcript level of SCD1 at the first time point to a reference profile; wherein a decrease in the RNA transcript level at the first time point compared to the reference profile indicates that the therapeutic agent is effective for treating the disease. In one aspect, the RNA transcript level of SCD1 in the sample from the subject is down regulated by at least about 50. In one aspect, the RNA transcript level of SCD1 is decreased by at least about 2-fold, 3-fold, 4-fold, 5-fold, 10-fold, 15-fold, or 20-fold. In one aspect, the reference profile is obtained from the subject prior to administering the therapeutic agent. In one aspect, the therapeutic agent is a compound of the invention. In one aspect, the disease is a lipoprotein related disorder. In one aspect, the disease is a cholesterol related disorder. In one aspect, the disease is a cardiovascular disease.

In one aspect, the invention provides a method of assessing the efficacy of a therapeutic agent for treating a disease in a subject comprising: (a) administering the therapeutic agent to the subject; (b) determining the RNA transcript level of MTTP in a sample from the subject at a first time point; and (c) comparing the RNA transcript level of MTTP at the first time point to a reference profile; wherein a decrease in the RNA transcript level at the first time point compared to the reference profile indicates that the therapeutic agent is effective for treating the disease. In one aspect, the RNA transcript level of MTTP in the sample from the subject is down regulated by any detectable amount. For example, the RNA transcript level of MTTP is down regulated by at least about 50%. In one aspect, the RNA transcript level of MTTP is decreased by at least about 2-fold, 3-fold, 4-fold, 5-fold, 10-fold, 15-fold, or 20-fold. In one aspect, the reference profile is obtained from the subject prior to administering the therapeutic agent. In one aspect, the therapeutic agent is a compound of the invention. In one aspect, the disease is a lipoprotein related disorder. In one aspect, the disease is a cholesterol related disorder. In one aspect, the disease is a cardiovascular disease.

In one aspect, the invention provides a method of assessing the efficacy of a therapeutic agent for treating a disease in a subject comprising: (a) administering the therapeutic agent to the subject; (b) determining the RNA transcript level of APOC3 in a sample from the subject at a first time point; and (c) comparing the RNA transcript level of APOC3 at the first time point to a reference profile; wherein a decrease in the RNA transcript level at the first time point compared to the reference profile indicates that the therapeutic agent is effective for treating the disease. In one aspect, the RNA transcript level of APOC3 in the sample from the subject is down regulated by any detectable amount. For example, the RNA transcript level of APOC3 is down regulated by at least about 50%. In one aspect, the RNA transcript level of APOC3 is decreased by at least about 2-fold, 3-fold, 4-fold, 5-fold, 10-fold, 15-fold, or 20-fold. In one aspect, the reference profile is obtained from the subject prior to administering the therapeutic agent. In one aspect, the therapeutic agent is a compound of the invention. In one aspect, the disease is a lipoprotein related disorder. In one aspect, the disease is a cholesterol related disorder. In one aspect, the disease is a cardiovascular disease. The invention provides a method of reducing the level of circulating LDL-cholesterol in a subject comprising administering to the subject a compound of the invention. In one aspect, the invention provides a method of monitoring a reduction in the level of circulating LDL-cholesterol in a subject, comprising: (a) determining a first level of expression of one or more signature genes or one or more products of one or more signature genes in a sample from the subject at a first time point; (b) administering to the subject a compound of the invention; (c) determining a second level of expression of the one or more signature genes or one or more products of one or more signature genes in a sample from the subject at a second time point; and (d) comparing the first level of expression with the second level of expression, wherein a change in the first level as compared to the second level indicates a reduction in the level of circulating LDL-cholesterol. In one aspect, the one or more signature genes selected from TRIB1, SCAP, SREBF1, SREBF2, PCSK9, LDLR, HMGCR, HMGCS, FASN, SCD1, MTTP and APOC3. The number of signature genes is 1, 2, 3, 4, 5, 6, 7, 8, 9, 10, 11, or 12.

In one aspect, invention provides a method of monitoring a reduction in the level of circulating LDL-cholesterol in a subject, comprising: (a) determining the level of LDL-cholesterol in a sample from the subject at a first time point; (b) administering to the subject a compound of the invention; (c) determining the level of LDL-cholesterol in a sample from the subject at a second time point after administration of the compound; and (d) comparing the level of LDL-cholesterol at the first and second time points. In one aspect, the level of circulating LDL-cholesterol is reduced by at least about 2-fold, 3-fold, 5-fold, 10-fold, 15-fold, or 20-fold.

The invention provides a method of reducing the level of circulating triglycerides in a subject comprising administering to the subject a compound of the invention. In one aspect, the invention provides a method of monitoring a reduction in the level of circulating triglycerides in a subject, comprising: (a) determining a first level of expression of one or more signature genes or one or more products of one or more signature genes in a sample from the subject at a first time point; (b) administering to the subject a compound of the invention; (c) determining a second level of expression of the one or more signature genes or one or more products of one or more signature genes in a sample from the subject at a second time point; and (d) comparing the first level of expression with the second level of expression, wherein a change in the first level as compared to the second level indicates a reduction in the level of circulating triglycerides. In one aspect, the one or more signature genes are selected from TRIB1, SCAP, SREBF1, SREBF2, PCSK9, LDLR, HMGCR, HMGCS, FASN, SCD1, MTTP and APOC3. The number of signature genes is 1, 2, 3, 4, 5, 6, 7, 8, 9, 10, 11, or 12.

In one aspect, the invention provides a method of monitoring a reduction in the level of circulating triglycerides in a subject, comprising: (a) determining the level of triglycerides in a sample from the subject at a first time point; (b) administering to the subject a compound of the invention; (c) determining the level of triglycerides in a sample from the subject at a second time point after administration of the compound; (d) comparing the levels of triglycerides obtained at the first and second time points. In one aspect, the level of circulating triglycerides is reduced by at least about 2-fold, 3-fold, 5-fold, 10-fold, 15-fold, or 20-fold.

The invention provides a method of reducing the secretion of VLDL particles from the liver into the bloodstream in a subject comprising administering to the subject a compound of the invention. In one aspect, the invention provides a method of monitoring a reduction in the secretion of VLDL particles in a subject, comprising: (a) determining a first level of expression of one or more signature genes or one or more products of one or more signature genes at a first time point; (b) administering to the subject a compound of the invention; (c) determining a second level of expression of the one or more signature genes or one or more products of one or more signature genes at a second time point; and (d) comparing the first level of expression with the second level of expression, wherein a change in the first level as compared to the second level indicates a reduction in the level of secretion of VLDL particles. In one aspect, the one or more signature genes selected from TRIB1, SCAP, SREBF1, SREBF2, PCSK9, LDLR, HMGCR, HMGCS, FASN, SCD1, MTTP and APOC3. The number of signature genes is 1, 2, 3, 4, 5, 6, 7, 8, 9, 10, 11, or 12.

In one aspect, the invention provides a method of monitoring a reduction in the secretion of VLDL particles from the liver into the bloodstream in a subject, comprising: (a) determining a first level of VLDL particles in a sample from the subject at a first time point; (b) administering to the subject a compound the invention; (c) determining the second level of VLDL particles in a sample from the subject at a second time point after administration of the compound; and (d) comparing the first level with the second level of VLDL particles. In one aspect, the level of VLDL particles is reduced by at least about 2-fold, 3-fold, 5-fold, 10-fold, 15-fold, or 20-fold.

The invention provides a method of reducing ApoB secretion in a subject comprising administering to the subject a compound the invention. In one aspect, the invention provides a method of monitoring a reduction in ApoB secretion in a subject, comprising: (a) determining a first level of expression of one or more signature genes or one or more products of one or more signature genes in a sample from the subject at a first time point; (b) administering to the subject a compound of the invention; (c) determining a second level of expression of the one or more signature genes or one or more products of one or more signature genes in a sample from the subject at a second time point; and (d) comparing the first level of expression with the second level of expression, wherein a change in the first level as compared to the second level indicates a reduction in the level of secretion of ApoB. In one aspect, the one or more signature genes selected from TRIB1, SCAP, SREBF1, SREBF2, PCSK9, LDLR, HMGCR, HMGCS, FASN, SCD, MTTP and APOC3. The number of signature genes is 1, 2, 3, 4, 5, 6, 7, 8, 9, 10, 11, or 12.

In one aspect, the invention provides a method of monitoring a reduction in ApoB secretion in a subject, comprising: (a) determining the level of ApoB in a sample from the subject at a first time point; (b) administering to the subject a compound of the invention; (c) determining the level of ApoB in a sample from the subject at a second time point after administration of the compound; and (d) comparing the levels of ApoB at the first and second time points. In one aspect, the level of ApoB is reduced by at least about 2-fold, 3-fold, 5-fold, 10-fold, 15-fold, or 20-fold.

The invention provides a method of reducing total serum cholesterol in a subject comprising administering to the subject a compound of the invention. In one aspect, the invention provides a method of monitoring a reduction in total serum cholesterol in a subject, comprising: (a) determining a first level of expression of one or more signature genes or one or more products of one or more signature genes in a sample from the subject at a first time point; (b) administering to the subject a compound of the invention; (c) determining a second level of expression of the one or more signature genes or one or more products of one or more signature genes in a sample from the subject at a second time point; and (d) comparing the first level of expression with the second level of expression, wherein a change in the first level as compared to the second level indicates a reduction in the level of total serum cholesterol. In one aspect, the one or more signature genes selected from TRIB1, SCAP, SREBF1, SREBF2, PCSK9, LDLR, HMGCR, HMGCS, FASN, SCD, MTTP and APOC3. The number of signature genes is 1, 2, 3, 4, 5, 6, 7, 8, 9, 10, 11, or 12.

In one aspect, the invention provides a method of monitoring a reduction in the total serum cholesterol level in a subject, comprising: (a) determining the level of total serum cholesterol in a sample from the subject at a first time point; (b) administering to the subject a compound of the invention; (c) determining the level of total serum cholesterol in a sample from the subject at a second time point after administration of the compound; and (d) comparing the levels of total serum cholesterol at the first and second time points. In one aspect, the level of total serum cholesterol is reduced by at least about 2-fold, 3-fold, 5-fold, 10-fold, 15-fold, or 20-fold.

Cholesterol Related Disorders

In one aspect, "a cholesterol related disorder" includes any one or more of the following: hypercholesterolemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using a compound of the invention, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apoplipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. A compound of the invention can also be useful in preventing or treating atherosclerotic diseases, such as, for example, coronary heart disease, coronary artery disease, peripheral arterial disease, stroke (ischaemic and hemorrhagic), angina pectoris, or cerebrovascular disease and acute coronary syndrome, myocardial infarction. In certain embodiments, the compounds of the invention are useful in reducing the risk of: nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries. In certain embodiments, the compounds of the invention and methods described herein can be used to reduce the risk of recurrent cardiovascular events.

In one aspect, the invention provides methods and compositions for treating and/or preventing cardiovascular diseases and related disorders. Cardiovascular diseases and related disorders referred to herein are diseases and disorders that involve the heart or blood vessels (e.g., arteries and veins). Cardiovascular diseases and related disorders include atherosclerosis, cardiac dysrhythmia, cardiomyopathy, coronary heart disease, hypertension, dyslipidemia, myocardial infarction, myocarditis, congestive heart failure, valvular heart disease, and vascular disease.

In one aspect, the invention provides a method and/or composition for treating and/or preventing myocardial infarction, coronary heart disease, atherosclerosis or dyslipidemia.

Myocardial infarction (MI) or acute myocardial infarction (AMI), commonly known as a heart attack, is the interruption of blood supply to part of the heart, causing myocardial cellular death. Classical symptoms of acute myocardial infarction include sudden chest pain, shortness of breath, nausea, vomiting, palpitations, sweating, anxiety, weakness, a feeling of indigestion, and fatigue. Myocardial infarctions are commonly a result of atherosclerosis, but are also associated with severe infections, intense psychological stress or physical exertion, coronary heart disease, and diabetes.

Coronary heart disease refers to any condition in which there is the narrowing or blockage of the coronary arteries, usually caused by atherosclerosis. Examples of coronary heart disease include, but are not limited to coronary artery disease.

Atherosclerosis is the buildup of cholesterol and fatty deposits, called plaques, on the inner walls of the arteries. Plaque formation causes thickening of the blood vessel walls, which obstructs blood flow and leads to diminished amounts of oxygen and nutrients reaching the target organ. Atherosclerosis can lead to ischemia, myocardial infarction, coronary heart disease, and/or congestive heart failure. Examples of atherosclerosis include, but are not limited to arteriosclerosis and ateriolosclerosis.

Dyslipidemia or dyslipidaemia is an abnormal amount of lipids in the blood. Examples of dyslipidemia include, but are not limited to hyperlipidemia, hypercholesterolemia, hyperglyceridemia, hyperlipoproteinemia, hyperchylomicronemia, and combined hyperlipidemia.

Cardiac dysrhythmia (also known as cardiac arrhythmia or irregular heartbeat) is a term for any of a large and heterogeneous group of conditions in which there is abnormal electrical activity in the heart. The most common symptom is palpitations, or abnormal heartbeats, which can be frequent, infrequent, or continuous. Arrhythmias can be associated with higher risk of blood clotting within the heart, embolism, stroke, heart failure and sudden cardiac death.

Examples of cardiac dysrhythmias include, but are not limited to proarrhythmia, sinus arrhythmia, premature atrial contractions, wandering atrial pacemaker, atrial flutter, premature ventricular contractions, accelerated idioventricular rhythm, atrioventricular blocks, sudden arrthythmic death syndrome, tachycardias (e.g., multifocal atrial tachycardia, supraventricular tachycardia, atrioventricular nodal reentrant tachycardia, junctional tachycardia, monomorphic ventricular tachycardia, polymorphic ventricular tachycardia), fibrillations (e.g., atrial fibrillation, ventricular fibrillation), and bradycardias.

Vascular disease includes diseases affecting the arteries, veins, lymph vessels, and blood disorders that affect circulation. Most commonly, vascular disease is associated atherosclerosis. Examples of vascular disease include, but are not limited to, cerebrovascular disease, peripheral artery disease, aneurysm, renal artery disease, Raynaud's Phenomenom, Buerger's Disease, peripheral venous disease, varicose veins, blood clotting disorders, blood clots in the veins, and lymphedema.

Cardiomyopathy is the deterioration of the function of the myocardium (the heart muscle), usually leading to heart failure. Examples of cardiomyopathies include, but are not limited to, hypertrophic cardiomyopathy, arrhythmogenic right ventricular cardiomyopathy, isolated ventricular noncompaction, mitochondrial myopathy, dilated cardiomyopoathy, restrictive cardiomyopathy, Takotsubo cardiomyopathy, Loeffler endocarditis, amyloidosis, hemochromatosis, Chagas disease, diabetic cardiomyopathy, alcoholic cardiomyopathy, obesity-associated cardiomyopathy, ischemic cardiomyopathy, and congestive heart failure.

Congestive heart failure (CHF), or heart failure, is a condition in which the heart is restricted from pumping enough blood to the body's other organs. This can result from narrowed arteries that supply blood to the heart muscle (e.g., coronary artery disease), past myocardial infarction having scar tissue that interferes with the heart muscle's normal work, high blood pressure, heart valve disease due to past rheumatic fever or other causes, cardiomyopathy, congenital heart defects, endocarditis and/or myocarditis.

Hypertension, or high blood pressure, is a chronic medical condition in which the blood pressure in the arteries is elevated. Hypertension increases the risk for ischemic heart disease, strokes, peripheral vascular disease, heart failure, aortic aneurysm, diffuse atherosclerosis, pulmonary embolism, hypertensive retinopathy, and hypertensive nephropathy.

Valvular heart disease refers to any disease process involving one or more of the valves of the heart (e.g., the aortic valve, the mitral valve, the pulmonary valve, and the tricuspid valve). Valvular heart diseases include, but are not limited to, rheumatic heart disease, mitral valve prolapse, heart valve dysplasia, Ebstein's anomaly, tetralogy of Fallot, aortic stenosis, mitral stenosis, pulmonary stenosis, tricuspid stenosis, aortic regurgitation or incompetence, mitral regurgitation or incompetence, pulmonary regurgitation or incompetence, tricuspid regurgitation or incompetence and restenosis.

Myocarditis is inflammation of heart muscle (myocardium) often resulting in damage to the heart. The most common cause is infection. Endocarditis is inflammation of the inside lining of the heart chambers and heart valves (endocardium). Associated conditions include chest pain, congestive heart failure, dilated cardiomyopathy, cardiac arrhythmias and heart blocks.

Other cardiovascular related disorders include stroke, diabetes, inflammation-related heart conditions, aneurysm and ischemia.

Liver Disease and Related Disorders

In one aspect, the invention relates to a method for treating and/or preventing liver disease, liver cancer, liver injury (e.g., alcohol misuse, viral and other infections, metabolic disorders, obesity, autoimmune disease, and drug toxicity), or abnormal liver function.

The term "liver disease" applies to a disease or disorder that causes the liver to function improperly or stop functioning. Examples include, but are not limited to, steatosis, nonalcoholic steatohepatitis (NASH), cirrhosis, amebic liver abscess, autoimmune hepatitis, biliary atresia, coccidioidomycosis, delta agent (Hepatitis D), drug-induced cholestasis, hemochromatosis, Hepatitis A, Hepatitis B, Hepatitis C, alcohol-induced liver disease, primary biliary cirrhosis, pyogenic liver abscess, Reye syndrome, sclerosing cholangitis, and Wilson's disease.

As used herein, liver cancer includes a disorder and/or a stage of progression associated with liver cancer. Examples of liver cancer include, but are not limited to, liver cell dysplasia, hepatic microvasculary dysplasia, portal atresia, primary liver cancer, hepatoma, hepatocellular carcinoma, or metastatic liver cancer (in which the cancer has spread to the liver, but originated from a different organ).

Combination Therapies

The invention includes combination therapies including the methods of treating and/or preventing conditions described herein. Combination therapy includes administering one or more compounds of the invention, or one or more compounds of the invention in combination with at least one or more additional medicaments. In one aspect, the other medicament may be a pharmaceutically active agent or a non-pharmaceutically active ingredient (e.g., surgery).

The invention provides a pharmaceutical composition comprising a compound of the invention and one or more additional medicaments. In one aspect, the invention provides a combination therapy for use in any of the methods described herein. In one aspect, the invention provides a method of treating or preventing a disease in a subject in need thereof comprising administering to the subject an effective amount of a first medicament and one or more additional medicaments. In one aspect, a compound of the invention is the first medicament of the combination therapy. In one aspect, one or more additional medicaments are the second medicament of the combination therapy. In one aspect, there is one additional medicament. In one aspect, there are two additional medicaments. In one aspect, there are three additional medicaments.

In one aspect, the invention provides a combination therapy for use in a method of the invention, wherein administration of the one or more additional medicaments of the combination therapy reduces the level of Low Density Lipoprotein-cholesterol (LDL-C) in the blood, and more particularly in the serum, of the subject. In some aspects, the one or more additional medicaments decrease LDL-C levels by at least about 2-fold, 3-fold, 5-fold, 10-fold, 15-fold, or 20-fold as compared to pre-treatment levels. In one aspect, administration of the one or more additional medicaments decreases LDL-C levels such that the level LDL-C is less than the level of LDL-C obtained through administration of the one or more additional medicaments alone. In one aspect, the invention provides a combination therapy for use in a method of the invention, wherein administration of one or more additional medicaments of the combination therapy elevates the level of HDL-cholesterol in the blood, and in one aspect, in the serum, of the subject. In some aspects, the one or more additional medicaments increase the HDL-cholesterol levels by at least about 2-fold, 3-fold, 5-fold, 10-fold, 15-fold, or 20-fold as compared to pre-treatment levels. In one aspect, administration of the one or more additional medicaments increases the level of HDL-cholesterol such that the level HDL-cholesterol is greater than the level of HDL-cholesterol obtained through administration of the one or more additional medicaments alone.

In one aspect, the invention provides a combination therapy for use in a method of the invention, wherein the one or more additional medicaments of the combination therapy upregulate the expression level of LDLR. In one aspect, administration of the one or more additional medicaments increases LDLR expression levels in the subject by 5 to 60%. In some aspects, LDLR expression levels are increased by at least about 1, 2, 3, 4, 5, 6, 7, 8, 9, 10, 11, 12, 13, 14, 15, 16, 17, 18, 19, 20, 25, 30, 35, 40, 45, 50, 55, or by at least about 60%. In one aspect, administration of the one or more additional medicaments increases LDLR expression levels for at least about 1, 2, 3, 4, 5, 7, 10, 14, 21, 25, 30 or 40 or more days. In one aspect, administration of the one or more additional medicaments increases LDLR expression levels such that the level of LDLR expression is greater than the level of LDLR obtained through administration of the one or more additional medicaments alone.

In one aspect, the invention provides a combination therapy for use in a method of the invention, wherein administration of the one or more additional medicaments upregulate the expression level of PCSK9. In one aspect, the additional medicament is a statin. In one aspect, the additional medicament is atorvastatin.

In one aspect, administration of the one or more additional medicaments reduces PCSK9 expression. In one aspect, the one or more additional medicaments reduces the levels by at least about 2-fold, 3-fold, 5-fold, 10-fold, 15-fold, or 20-fold as compared to pre-treatment levels. In one aspect, the expression level of PCSK9 is lower than the expression level of PCSK9 obtained through administration of the first medicament or one or more additional medicaments alone.

In one aspect, the invention provides a combination therapy for use in any of the methods described herein, wherein the combination therapy comprises a compound of the invention and one or more additional medicaments selected from a small molecule, an antibody, or a small interferring RNA (siRNA) or a combination thereof.

In one aspect, the invention provides a combination therapy for use in any of the methods described herein, wherein the additional medicament is a small molecule. In one aspect, the small molecule is a HMG-CoA reductase inhibitor. Exemplary HMG-CoA reductase inhibitors include atorvastatin (Pfizer's Lipitor®/Tahor/Sortis/Torvast/Cardyl), pravastatin (Bristol-Myers Squibb's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis). In one aspect, the HMG-CoA reductase is a statin. In one aspect, the statin is selected from atorvastatin, fluvastatin, lovastatin, mevastatin, pitavastatin, pravastatin, rosuvastatin, simvastatin, cerivastatin, and any combination thereof. In one aspect, the statin is simvastatin. In one aspect, the statin is atorvastatin.

In one aspect, the invention provides a combination therapy for use in any of the methods described herein, wherein the additional medicament is an antibody. In one aspect, the antibody is a PCSK9 antibody (See e.g., US 2012/0195910). In one aspect, the anti-PCSK9 antibody inhibits binding of human PCSK9 to LDLR by at least about 20-40%, 40-60%, 60-80%, 80-85%, or more.

In one aspect, the invention provides a combination therapy for use in any of the methods described herein, wherein the additional medicament is a siRNA (See e.g, US 2012/0244207). In one aspect, the siRNA targets a VSP, TTR, PCSK-9, SCAP, S14, MIG12, APOC3, APOB, PNPLA3, Hepcidin, or a PCSK5 gene. In one aspect, siRNA targeted gene is suppressed by at least about 5%, 10%, 15%, 20%, 25%, 30%, 35%, 40%, 45%, or 50% by administration of a siRNA. In one aspect, the siRNA targeted gene is suppressed by at least about 60%, 70%, or 80% by administration of the siRNA. In one aspect, the siRNA targeted gene is suppressed by at least about 85%, 90%, or 95% by administration of the siRNA.

In one aspect, the siRNA is a PCSK9 targeted siRNA. In one aspect, the siRNA targeted to the PCSK9 gene and administration results in a decrease in LDLc (low density lipoprotein cholesterol) levels in the blood, and more particularly in the serum, of the mammal. In one aspect, LDLc levels are decreased by at least 5%, 10%, 15%, 20%, 25%, 30%, 40%, 50%, or 60%, or more, as compared to pretreatment levels.

In one aspect, the PCSK9 targeted siRNA comprises AD-10792 or AD-9680.

In one aspect, the invention provides a method, wherein administration of the first medicament and one or more additional medicaments of the combination therapy upregulates the expression level of LDLR.

In one aspect, the invention provides a method, wherein the expression level of LDLR is greater than the expression level of LDLR obtained through administration of the first medicament or one or more additional medicaments alone.

In one aspect, the invention provides a method, wherein the expression level of PCSK9 is lower than the expression level of PCSK9 obtained through administration of one or more additional medicaments alone.

In one aspect, the additional medicament of the combination therapy is for preventing and/or treating atherosclerosis and/or cardiovascular disease. In one aspect, the additional medicament is for use in a method of reducing the risk of recurrent cardiovascular events. In one aspect, the additional medicament is for elevating the level of HDL-cholesterol in a subject.

In one aspect, the additional medicament of the combination therapy is an inhibitor of PCSK9 expression, e.g., a PCSK9 antibody or a PCSK9 targeted siRNA.

Examples of other medicaments for use in the combination therapy with a compound of the invention include: antibiotics; anti-histamines; aspirin; antiarrthythmic agents (e.g., quinidine, procainadmide, disopyramide, lidocain, phenytoin, mexiletine, flecainid), anticoagulants (e.g., warfarin and heparins); antiplatelet drug therapy (e.g., aspirin and clopidogrel); angiotensin-converting enzyme (ACE) inhibitors (e.g., captopril, zofenopril, enalapril, ramipril, quinapril, perindopril, lisinopril, benazepril, fosinopril, casokinins and lactokinins); aldosterone antogonis agents (e.g., eplerenone and spironolactone); antianginal drugs; antihypertensive drugs; angiotensin antagonists; antiviral drugs; antifungal drugs; immunosuppressants; inotropes (e.g., Milrinone), estradiol, berberine, statins (e.g., atorvastatin, cerivastatin, fluvastatin, lovastatin, pitavastatin, mevastatin, pravastatin, rosuvastatin, and simvastatin), growth factors; hormones; steroids; thrombolytic drugs; cardioplegic solutions; cariotonic agents; fibrinolytic agents; nitric oxide donors; nitroglycerin; potassium channel blockers; sodium channel blockers; vasoconstrictors; vasodilators; beta blockers; cholesterol-lowering medications; calcium channel blockers; digitalis; diuretics; dietary supplements (e.g., folic acid, niacin, omega 3 fatty acids, and Vitamin C); receptor kinase inhibitors; and chemotherapeutic reagents.

In one aspect, the one or more additional medicaments for use in the combination therapy is selected from an HMG-CoA reductase inhibitor, a fibrate, a bile acid sequestrant, niacin, an antiplatelet agent, an angiotensin converting enzyme inhibitor, an angiotensin II receptor antagonist, an acyl-CoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR) agonist, a gene-based therapy, a composite vascular protestant, a glycoprotein IIb/IIIa inhibitor, aspirin or an aspirin-like compound, an IBAT inhibitor, a squalene synthase inhibitor, and a monocyte chemoattractant protein (MCP)-I inhibitor.

In another aspect, the one or more additional medicaments for use in the combination therapy a compound of the invention is selected from an HMG-CoA reductase inhibitor (e.g., a statin), a fibrate, a bile acid sequestrant, niacin, an antiplatelet agent, an angiotensin converting enzyme inhibitor, an angiotensin II receptor antagonist (e.g., losartan potassium, such as Merck & Co.'s Cozaar®, an acylCoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR) agonist, a gene-based therapy, a composite vascular protectant (e.g., AGI-1067, from Atherogenics), a glycoprotein IIb/IIIa inhibitor, aspirin or an aspirin-like compound, an IBAT inhibitor (e.g., S-8921, from Shionogi), a squalene synthase inhibitor, or a monocyte chemoattractant protein (MCP)-I inhibitor. Examplary HMG-CoA redutase inhibitors are described herein. Exemplary fibrates include, e.g., bezafibrate (e.g., Roche's Befizal®/Cedur®/Bezalip®, Kissei's Bezatol), clofibrate (e.g., Wyeth's Atromid-S®), fenofibrate (e.g., Fournier's Lipidil/Lipantil, Abbott's Tricor®, Takeda's Lipantil, generics), gemfibrozil (e.g., Pfizer's Lopid/Lipur) and ciprofibrate (Sanofi-Synthelabo's Modalim®). Exemplary bile acid sequestrants include, e.g., cholestyramine (Bristol-Myers Squibb's Questran® and Questran Light™), colestipol (e.g., Pharmacia's Colestid), and colesevelam (Genzyme/Sankyo's WelChol™). Exemplary niacin therapies include, e g, immediate release formulations, such as Aventis' Nicobid, Upsher-Smith's Niacor, Aventis' Nicolar, and Sanwakagaku's Perycit. Niacin extended release formulations include, e.g., Kos Pharmaceuticals' Niaspan and Upsher-Smith's SIo-Niacin. Exemplary antiplatelet agents include, e.g., aspirin (e.g., Bayer's aspirin), clopidogrel (Sanofi-Synthelabo/Bristol-Myers Squibb's Plavix), and ticlopidine (e.g., Sanofi-Synthelabo's Ticlid and Daiichi's Panaldine). Other aspirin-like compounds useful in combination with a dsRNA include, e.g., Asacard (slow-release aspirin, by Pharmacia) and Pamicogrel (Kanebo/Angelini Ricerche/CEPA). Exemplary angiotensin-converting enzyme inhibitors include, e.g., ramipril (e.g., Aventis' Altace) and enalapril (e.g., Merck & Co.'s Vasotec). Exemplary acyl CoA cholesterol acetyltransferase (ACAT) inhibitors include, e.g., avasimibe (Pfizer), eflucimibe (BioMerieux Pierre Fabre/Eli Lilly), CS-505 (Sankyo and Kyoto), and SMP-797 (Sumito). Exemplary cholesterol absorption inhibitors include, e.g., ezetimibe (Merck/Schering-Plough Pharmaceuticals Zetia®) and Pamaqueside (Pfizer). Exemplary CETP inhibitors include, e.g., Torcetrapib (also called CP-529414, Pfizer), JTT-705 (Japan Tobacco), and CETi-I (Avant Immunotherapeutics). Exemplary microsomal triglyceride transfer protein (MTTP) inhibitors include, e.g., implitapide (Bayer), R-103757 (Janssen), and CP-346086 (Pfizer). Other exemplary cholesterol modulators include, e.g., NO-1886 (Otsuka/TAP Pharmaceutical), CI-1027 (Pfizer), and WAY-135433 (Wyeth-Ayerst). Exemplary bile acid modulators include, e.g., HBS-107 (Hisamitsu/Banyu), Btg-511 (British Technology Group), BARI-1453 (Aventis), S-8921 (Shionogi), SD-5613 (Pfizer), and AZD-7806 (AstraZeneca). Exemplary peroxisome proliferation activated receptor (PPAR) agonists include, e.g., tesaglitazar (AZ-242) (AstraZeneca), Netoglitazone (MCC-555) (Mitsubishi/Johnson & Johnson), GW-409544 (Ligand Pharmaceuticals/GlaxoSmithKline), GW-501516 (Ligand Pharmaceuticals/GlaxoSmithKline), LY-929 (Ligand Pharmaceuticals and Eli Lilly), LY-465608 (Ligand Pharmaceuticals and Eli Lilly), LY-518674 (Ligand Pharmaceuticals and Eli Lilly), and MK-767 (Merck and Kyorin). Exemplary gene-based therapies include, e.g., AdGWEGF121.10 (GenVec), ApoA1 (UCB Pharma/Groupe Fournier), EG-004 (Trinam) (Ark Therapeutics), and ATP-binding cassette transporter-A1 (ABCA1) (CV Therapeutics/Incyte, Aventis, Xenon). Exemplary Glycoprotein IIb/IIIa inhibitors include, e.g., roxifiban (also called DMP754, Bristol-Myers Squibb), Gantofiban (Merck KGaA/Yamanouchi), and Cromafiban (Millennium Pharmaceuticals). Exemplary squalene synthase inhibitors include, e.g., BMS-1884941 (Bristol-Myers Squibb), CP-210172 (Pfizer), CP-295697 (Pfizer), CP-294838 (Pfizer), and TAK-475 (Takeda). An exemplary MCP-I inhibitor is, e.g., RS-504393 (Roche Bioscience). The anti-atherosclerotic agent BO-653 (Chugai Pharmaceuticals), and the nicotinic acid derivative Nyclin (Yamanouchi Pharmaceuticals) are also appropriate for administering in combination with a compound of the invention. Exemplary combination therapies suitable for administration with a compound of the invetnion, e.g., advicor (Niacin/lovastatin from Kos Pharmaceuticals), amlodipine/atorvastatin (Pfizer), and ezetimibe/simvastatin (e.g., Vytorin®10/10, 10/20, 10/40, and 10/80 tablets by Merck/Schering-Plough Pharmaceuticals). Agents for treating hypercholesterolemia, and suitable for administration in combination with a compound of the invention include, e.g., lovastatin, niacin Altoprev®Extended-Release Tablets (Andrx Labs), lovastatin Caduet™. Tablets (Pfizer), amlodipine besylate, atorvastatin calcium Crestor®Tablets (AstraZeneca), rosuvastatin calcium Lescol® Capsules (Novartis), fluvastatin sodium Lescol® (Reliant, Novartis), fluvastatin sodium Lipitor® Tablets (Parke-Davis), atorvastatin calcium Lofibra® Capsules (Gate), Niaspan Extended-Release Tablets (Kos), niacin Pravachol Tablets (Bristol-Myers Squibb), pravastatin sodium TriCor® Tablets (Abbott), fenofibrate Vytorin® 10/10 Tablets (Merck/Schering-Plough Pharmaceuticals), ezetimibe, simvastatin WelChol™ Tablets (Sankyo), colesevelam hydrochloride Zetia® Tablets (Schering), ezetimibe Zetia® Tablets (Merck/Schering-Plough Pharmaceuticals), and ezetimibe Zocor® Tablets (Merck).

Other therapies or medicaments known in the art for treating cholesterol disorders, cardiovascular diseases and related conditions which may be combined with one or more compound of the invention include: angioplasty; brachytherapy; surgery; coronary artery bypass; stents; pacemakers; ventricular assist devices (LVADs); defibrillators; heart transplant; liver transplant; intracoronary radiation; exercise; weight control; smoking cessation; and dietary restriction.

It is understood that the combination therapies described herein can be used in any of the methods of the invention, including but not limited to a method of treating a disease, including a cholesterol disorder or cardiovascular disease. It is understood that any of the methods of assessing the efficacy of a therapeutic agent can be applied to assess the efficacy of a combination therapy e.g., the therapeutic agent is a compound of the invention and one or more additional agents as described herein. The methods of monitoring the effects of a compound of the invention described herein are also applicable for monitoring the effects of combination therapies described herein e.g., methods of monitoring a reduction in the level of circulating LDL-cholesterol, a reduction in the level of circulating triglycerides, a reduction in the secretion of VLDL particles, etc.

In one aspect, the invention provides a combination therapy for use in a method of the invention, wherein the first medicament and one or more additional medicaments are administered simultaneously or in parallel by combination of the first and one or more additional medicaments in a co-formulation or separate formulations or by alternation.

In one aspect, the invention provides a combination therapy for use in method of the invention, wherein administration of the first medicament and one or more additional medicaments by alteration consists of delivering the first medicament and the one or more additional medicaments serially, sequentially, or alternating in separate pharmaceutical formulations.

In one aspect, the invention provides a combination therapy for use in a method of the invention, wherein the one or more additional medicaments are administered before the first medicament.

In one aspect, the invention provides a combination therapy for use in a method of the invention, comprising administration of the first medicament and one additional medicament.

In one aspect, the invention provides a combination therapy for use in a method of the invention, wherein the first medicament being administered after the one or more additional medicaments reduces the expression level of PCSK9.

The invention further provides a medical device containing a combination therapy e.g., compound of the invention and one or more additional medicaments. The one or more additional medicaments can be any of the medicaments described above. In one aspect, the additional medicament is a statin. In one aspect, the medical device is a stent.

Formulation

The compounds of the invention may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus calmatte-guerin, Shigella, Lactobacillus*); Live viral vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The term an "effective amount" of a compound of the invention refers to the amount necessary or sufficient to realize a desired biologic effect. For example, an effective amount of a compound of the invention is that amount sufficient to treat a disease, disorder, or condition. In another aspect, an effective amount of a compound is that amount sufficient to prevent a disease, disorder, or condition. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the condition being treated, the particular compounds being administered the size of the subject, or the severity of the condition.

The compounds of the invention may be administered by any route known, such as, for example, orally, transdermally, intravenously, cutaneously, subcutaneously, nasally, intramuscularly, intraperitoneally, intracranially, and intracerebroventricularly.

In certain embodiments, compounds of the invention are administered at dosage levels greater than about 0.001 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can also be administered to a subject.

In one embodiment, the compound of the invention is administered once-daily, twice-daily, or three-times daily. In one embodiment, the compound of the invention is administered continuously (i.e., every day) or intermittently (e.g., 3-5 days a week). In another embodiment, administration could be on an intermittent schedule.

Further, administration less frequently than daily, such as, for example, every other day may be chosen. In additional embodiments, administration with at least 2 days between doses may be chosen. By way of example only, dosing may be every third day, bi-weekly or weekly. As another example, a single, acute dose may be administered. Alternatively, compounds of the invention can be administered on a non-regular basis e.g., whenever symptoms begin. For any compound described herein the effective amount can be initially determined from animal models.

Toxicity and efficacy of the compounds of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds of the invention for use in humans. The dosage of such agents lies preferably within a range of circulating concentrations that include the ED50 with little or no toxicity. The dosage may vary within this range depending upon the dosage form employed and the route of administration utilized. For any compound used in the method of the invention, the effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. Multiple doses of the compounds of the invention are also contemplated.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of one or more compounds of the invention can be administered to a subject by any mode that delivers the compound(s) to the desired surface, e.g., mucosal, systemic. Administering the pharmaceutical composition of the present invention may be accomplished by any means known to the skilled artisan. Compounds of the invention may be administered orally, transdermally, intravenously, cutaneously, subcutaneously, nasally, intramuscularly, intraperitoneally, intracranially, or intracerebroventricularly.

For oral administration, one or more compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of one or more compounds of the invention. The compound(s) may be chemically modified so that oral delivery of the derivative is efficacious. Generally, the chemical modification contemplated is the attachment of at least one moiety to the compound itself, where said moiety permits (a) inhibition of proteolysis; and (b) uptake into the blood stream from the stomach or intestine. Also desired is the increase in overall stability of the compound(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4: 185-189. Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The compound of the invention can be included in the formulation as fine multiparticulates in the form of granules or pellets of particle size about 1 mm. The formulation of the material for capsule administration could also be as a powder, lightly compressed plugs or even as tablets. The compound of the invention could be prepared by compression.

Colorants and flavoring agents may all be included. For example, the compound of the invention may be formulated (such as by liposome or microsphere encapsulation) and then further contained within an edible product, such as a refrigerated beverage containing colorants and flavoring agents.

One may dilute or increase the volume of compound delivered with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell. Disintegrants may be included in the formulation of the therapeutic into a solid dosage form. Materials used as disintegrates include but are not limited to starch, including the commercial disintegrant based on starch, Explotab.

Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the compound of the invention to prevent sticking during the formulation process. Lubricants may be used as a layer between the compound and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compound into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the invention. The compound is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63: 135-144 (leuprolide acetate); Braquet et al., 1989, Journal of Cardiovascular Pharmacology, 13(suppl. 5): 143-146 (endothelin-1); Hubbard et al., 1989, Annals of Internal Medicine, Vol. IJJ, pp. 206-212 (a1-antitrypsin); Smith et al., 1989, J. Clin. Invest. 84: 1 145-1 146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified compound may also be prepared in different formulations depending on the type of chemical modification or the type of device employed. Formulations suitable for use with a nebulizer, either jet or ultrasonic, will typically comprise compound dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifiuoromethane, dichlorotetrafluoroethanol, and 1,1,1,2-tetrafluoroethane, or combinations thereof. Suitable surfactants include sorbitan trioleate and soya lecithin Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., 50 to 90% by weight of the formulation. The compound should most advantageously be prepared in particulate form with an average particle size of less than 10 mm (or microns), most preferably 0.5 to 5 mm, for most effective delivery to the distal lung.

Nasal delivery of a compound of the invention is also contemplated. Nasal delivery allows the passage of a compound of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compound, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions.

Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249: 1527-1533, 1990, which is incorporated herein by reference.

The compounds of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a compound of the invention optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the invention, and with each other, in a manner such that there is no interaction which would substantially impair the desired pharmaceutical efficiency.

The dsRNA molecules of the combination therapy described herein may be administered in a number of ways depending upon whether local or systemic treatment is desired and upon the area to be treated. Administration of the dsRNA may be topical, pulmonary, e.g., by inhalation or insufflation of powders or aerosols, including by nebulizer; intratracheal, intranasal, epidermal and transdermal, and subdermal, oral or parenteral, e.g., subcutaneous. For example, when treating a subject with hyperlipidemia, the dsRNA may be administered systemically via parental means. Parenteral administration includes intravenous, intra-arterial, subcutaneous, intraperitoneal or intramuscular injection or infusion; or intracranial, e.g., intraparenchymal, intrathecal or intraventricular, administration. For example, dsRNAs, conjugated or unconjugated or formulated with or without liposomes, can be administered intravenously to a subject. For such, a dsRNA can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. For parenteral, intrathecal, or intraventricular administration, a dsRNA can be formulated into compositions such as sterile aqueous solutions, which also can contain buffers, diluents, and other suitable additives (e.g., penetration enhancers, carrier compounds, and other pharmaceutically acceptable carriers). Formulations are described in more detail herein. The dsRNA can be delivered in a manner to target a particular tissue, such as the liver (e.g., the hepatocytes of the liver).

The dsRNA (siRNA) of the combination therapy described herein may be formulated into any of many possible dosage forms such as, but not limited to, tablets, capsules, gel capsules, liquid syrups, soft gels, suppositories, and enemas. The dsRNA may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

The dsRNA in the combination therapy described herein include, but are not limited to, solutions, emulsions, and liposome-containing formulations. These dsRNA formulations may be generated from a variety of components that include, but are not limited to, preformed liquids, self-emulsifying solids and self-emulsifying semisolids. In one aspect, they are formulations that target the liver when treating hepatic disorders such as hyperlipidemia.

In addition, dsRNA that target the target gene can be formulated into compositions containing the dsRNA admixed, encapsulated, conjugated, or otherwise associated with other molecules, molecular structures, or mixtures of nucleic acids in addition to a compound of the invention. For example, a composition containing one or more dsRNA agents that target the target gene can contain other therapeutic agents, such as one or more dsRNA compounds that target other target genes.

dsRNA compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the combination thereapy described herein are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24, 25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some aspects, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. dsRNAs featured in the combination therapy of the invention may be delivered orally, in granular form including sprayed dried particles, or complexed to form micro or nanoparticles. dsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyomithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, U.S. Patent Publication. No. 20030027780, and U.S. Pat. No. 6,747,014.

dsRNA compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

dsRNA pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). dsRNAs featured in the invention may be encapsulated within liposomes or may form complexes thereto. Alternatively, dsRNAs may be complexed to lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. Pat. No. 6,747,014. In addition, dsRNA molecules can be administered to a mammal as biologic or abiologic means as described in, for example, U.S. Pat. No. 6,271,359. Abiologic delivery can be accomplished by a variety of methods including, without limitation, (1) loading liposomes with a dsRNA acid molecule provided herein and (2) complexing a dsRNA molecule with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine Numerous lipophilic agents are commercially available, including Lipofectin™ (Invitrogen/Life Technologies, Carlsbad, Calif.) and Effectene™ (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (Nature Biotechnology, 15: 647-652 (1997)) can be used. In other embodiments, polycations such as polyethyleneimine can be used to achieve delivery in vivo and ex vivo (Boletta et al., J. Am. Soc. Nephrol. 7: 1728 (1996)). Additional information regarding the use of liposomes to deliver nucleic acids can be found in U.S. Pat. No. 6,271,359, PCT Publication WO 96/40964 and Morrissey, D. et al. 2005. Nat. Biotechnol. 23(8):1002-7.

Biologic delivery of dsRNA can be accomplished by a variety of methods including, without limitation, the use of viral vectors. For example, viral vectors (e.g., adenovirus and herpes virus vectors) can be used to deliver dsRNA to liver cells. Standard molecular biology techniques can be used to introduce one or more of the dsRNAs provided herein into one of the many different viral vectors previously developed to deliver nucleic acid to cells. These resulting viral vectors can be used to deliver the one or more dsRNAs to cells by, for example, infection. The dsRNA of the combination therapy described herein can be formulated according to the liposomal formulations described in US2012/0244207.

The dsRNA of the combination therapy described herein are administered in dosages sufficient to inhibit expression of target genes. In one aspect, the dosage of the dsRNA of the combination therapy described herein is lower than the dosage of the dsRNA when administered alone. In general, a suitable dose of dsRNA will be in the range of 0.01 to 200.0 milligrams per kilogram body weight of the recipient per day, generally in the range of 1 to 50 mg per kilogram body weight per day. For example, the dsRNA can be administered at 0.01 mg/kg, 0.05 mg/kg, 0.5 mg/kg, 1 mg/kg, 1.5 mg/kg, 2.0 mg/kg, 3.0 mg/kg, 5.0 mg/kg, 10 mg/kg, 20 mg/kg, 30 mg/kg, 40 mg/kg, or 50 mg/kg per single dose.

In another aspect, the dosage is between 0.01 and 0.2 mg/kg. For example, the dsRNA can be administered at a dose of 0.01 mg/kg, 0.02 mg/kg, 0.03 mg/kg, 0.04 mg/kg, 0.05 mg/kg, 0.06 mg/kg, 0.07 mg/kg 0.08 mg/kg 0.09 mg/kg, 0.10 mg/kg, 0.11 mg/kg, 0.12 mg/kg, 0.13 mg/kg, 0.14 mg/kg, 0.15 mg/kg, 0.16 mg/kg, 0.17 mg/kg, 0.18 mg/kg, 0.19 mg/kg, or 0.20 mg/kg.

In one aspect, the dosage is between 0.2 mg/kg and 1.5 mg/kg. For example, the dsRNA can be administered at a dose of 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, or 1.5 mg/kg. In one aspect, the dsRNA can be administered at a dose of 0.03, 0.1, 0.3, or 1.3, or 3.0 mg/kg.

In one aspect, the dsRNA can be administered once daily, or the dsRNA may be administered as two, three, or more sub-doses at appropriate intervals throughout the day. The effect of a single dose on target mRNA levels is long lasting, such that subsequent doses are administered at not more than 7 day intervals, or at not more than 1, 2, 3, or 4 week intervals.

In one aspect, the lipid formulated mRNA targeted dsRNA is administered at a first dose followed by administering at least one subsequent dose once a week, wherein the subsequent dose is lower than the first dose. The subsequent dose can be administered, e.g., once a week for four weeks. In some embodiments the dsRNA is administered using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The antibodies of the combination therapy describere herein can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

The anti-PCSK9 antibodies of the combination therapy described herein are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners.

For the prevention or treatment of disease using a combination therapy decribed herein, the appropriate dosage of an antibody will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the subject, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the subject. Such doses may be administered intermittently, e.g. every week or every three weeks (e.g. such that the patient receives from about two to about twenty, or e.g. about six doses of the antibody). An initial higher loading dose, followed by one or more lower doses may be administered.

In certain aspects, a flat-fixed dosing regimen is used to administer anti-PCSK9 antibody to an individual. Depending on the type and severity of the disease an exemplary flat-fixed dosage might range from 10 to 1000 mg of anti-PCSK9 antibody. One exemplary dosage of the antibody would be in the range from about 10 mg to about 600 mg. Another exemplary dosage of the antibody would be in the range from about 100 mg to about 600 mg. In certain embodiments, 150 mg, 300 mg, or 600 mg of anti-PCSK9 antibody is administered to an individual. However, other dosage regimens may be useful. It is understood that any of the above formulations or may be carried out using an immunoconjugate in place of or in addition to an anti-PCSK9 antibody.

Compounds of the invention and combination therapies described herein can be evaluated using a variety of methods known in the art. For example, the following methods can be used to evaluate compounds and combination therapies of the invention. Methods to evaluate compound efficacy or efficacy of combination therapy include measurement of cholesterol (including HDL and LDL cholesterol) and triglycerides in a patient. In specific cases, a fasting lipoprotein profile is performed, such as by standard means in the art.

Screening

The invention provides a method of identifying a compound for treating or preventing a disease comprising: a) contacting a first population of cells with a small molecule; b) determining the expression level of one or more signature genes or one or more products of the signature genes of the first population of cells at a first time point; c) comparing the expression level at the first time point to the expression level of the one or more signature genes or one or more products of the signature genes of a reference sample. In one aspect, the cell type of the population of cells is selected from hepatic, skin, adrenal gland, muscle, and kidney cell. In one aspect, the cell type is hepatic. In one aspect, the cell type is HepG2. In one aspect, the reference sample comprises a second population of cells comprising the same cell type as the first population of cells except that the second population of cells is not contacted with the small molecule. In one aspect, the one or more signature genes is selected from TRIB1, SCAP, SREBF1, SREBF2, PCSK9, LDLR, HMGCR, HMGCS, FASN, SCD1, MTTP and APOC3. The number of signature genes is 1, 2, 3, 4, 5, 6, 7, 8, 9, 10, 11, or 12. In one aspect, the compound identified increases the expression of TRIB1. In one aspect, the compound identified increases the expression of TRIB1 and decreases the expression of PCSK9. In one aspect, the compound identified decreases expression of one or more genes selected from HMGCR, HMGCS, FASN, SREBF1, SCD1, MTTP and APOC3. The number of genes is 1, 2, 3, 4, 5, 6, or 7. In one aspect, the compound identified does not change one or more genes selected from SCAP and SREBF2. The number of genes is 1 or 2.

The following Examples are illustrative and should not be interpreted in any way so as to limit the scope of the invention

EXAMPLES

Example 1

Preparation of Compounds of the Invention

Compounds of the invention were prepared according to synthetic methods known in the art. Compounds of the invention were prepared as described in the schemes below (see also, J. Org. Chem. 2011, 76, 1898-1901 for the preparation of starting materials). Scheme 1 shows the procedures used for the preparation of compounds 1a, 2a, 3a, 4a, 14a, 15a, and 16a. The table below Scheme 1 shows the reagents used to prepare each of the compounds.

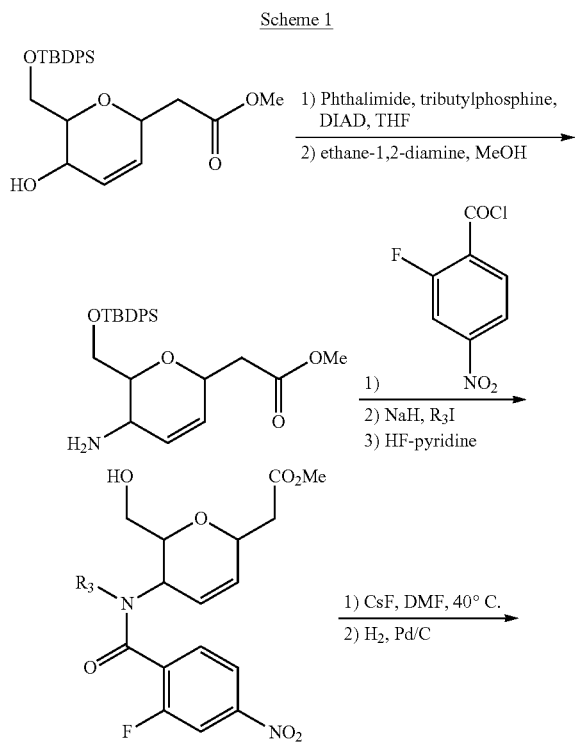

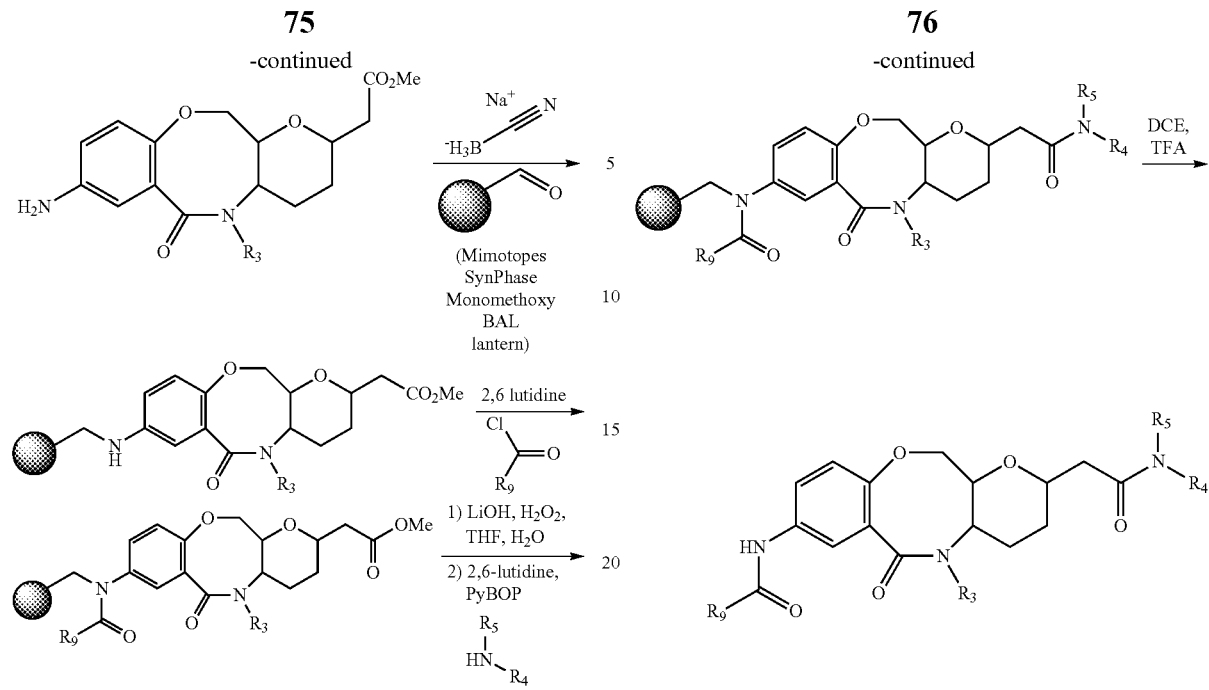

-continued
| Compound | R₃—I | NHR₄R₅ | R₉C(O)Cl |
|---|---|---|---|
| 14a | Methyl iodide | 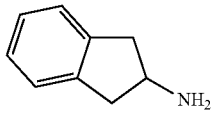 | 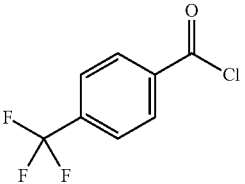 [SMILES: O=C(Cl)c1ccc(C(F)(F)F)cc1] |
| 15a | Methyl iodide | 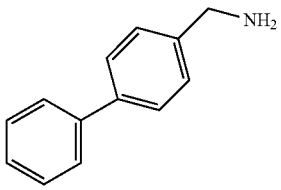 | 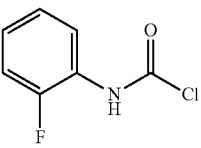 [SMILES: O=C(Cl)Nc1ccccc1F] |
| 16a | Methyl iodide | 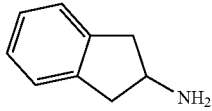 | 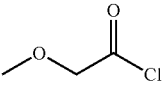 |
Scheme 2 shows the procedures used for the preparation of compounds 5a, 6a, 7a, 8a, 9a, and 10a. The table below Scheme 2 shows the reagents used to prepare each of the compounds.
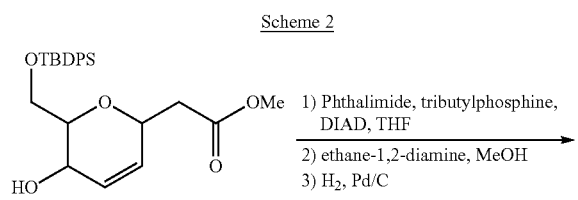
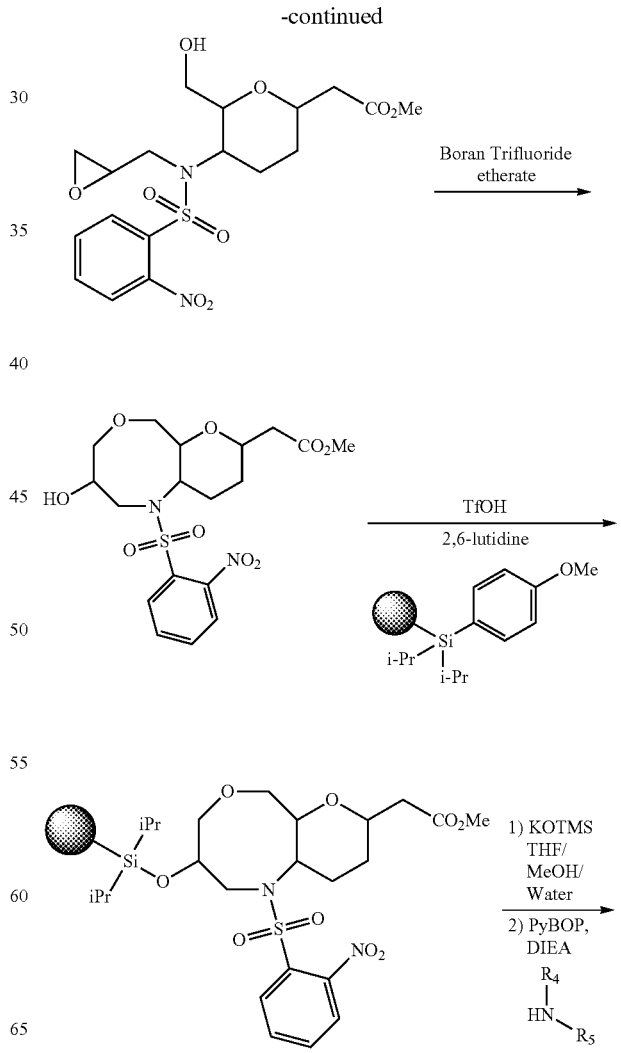

-continued

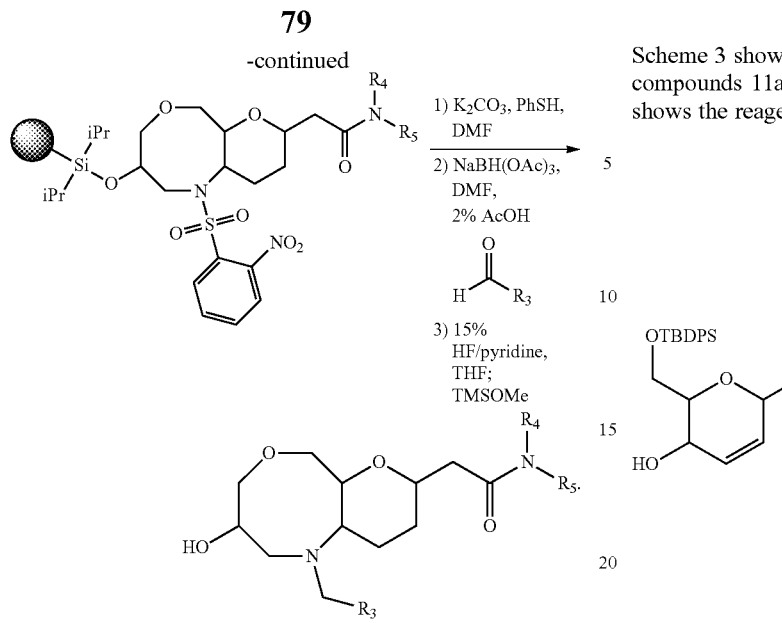

1) K₂CO₃, PhSH, DMF
2) NaBH(OAc)₃, DMF, 2% AcOH
3) 15% HF/pyridine, THF; TMSOMe

Scheme 3 shows the procedures used for the preparation of compounds 11a, 12a, and 13a. The table below Scheme 3 shows the reagents used to prepare each of the compounds.

Scheme 3

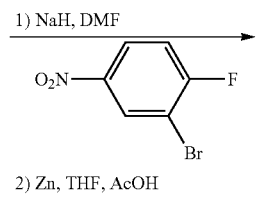

1) NaH, DMF
2) Zn, THF, AcOH

| Compound | HC(O)R₃ | HNR₄R₅ |
|---|---|---|
| 5a | 4-phenoxybenzaldehyde | 1,2,3,4-tetrahydroisoquinoline |
| 6a | 4-phenoxybenzaldehyde | 1,2,3,4-tetrahydroisoquinoline |
| 7a | 4-phenoxybenzaldehyde | 1,2,3,4-tetrahydroisoquinoline |
| 8a | 3,3,3-trifluoropropanal | 4-phenoxybenzylamine |
| 9a | 4-phenoxybenzaldehyde | 1,2,3,4-tetrahydroisoquinoline |
| 10a | 3,3,3-trifluoropropanal | 4-phenoxybenzylamine |

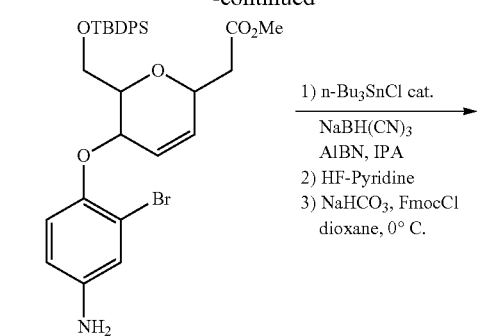
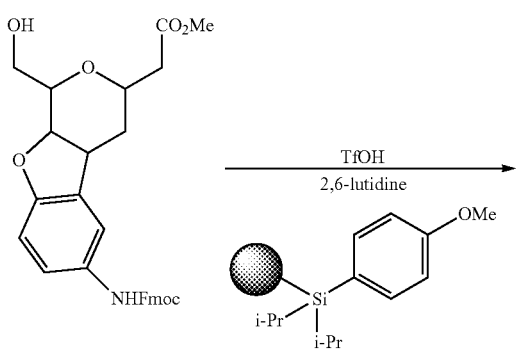
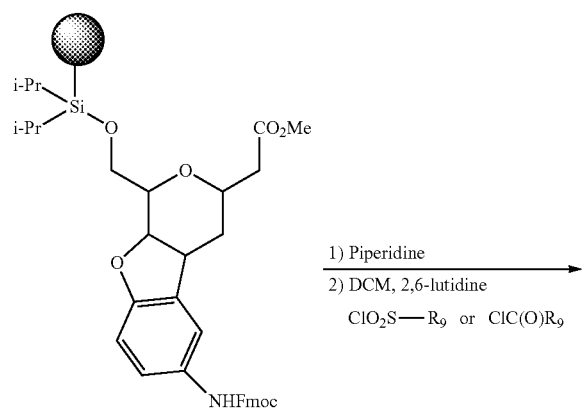
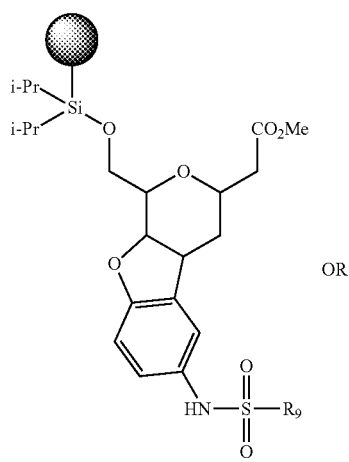
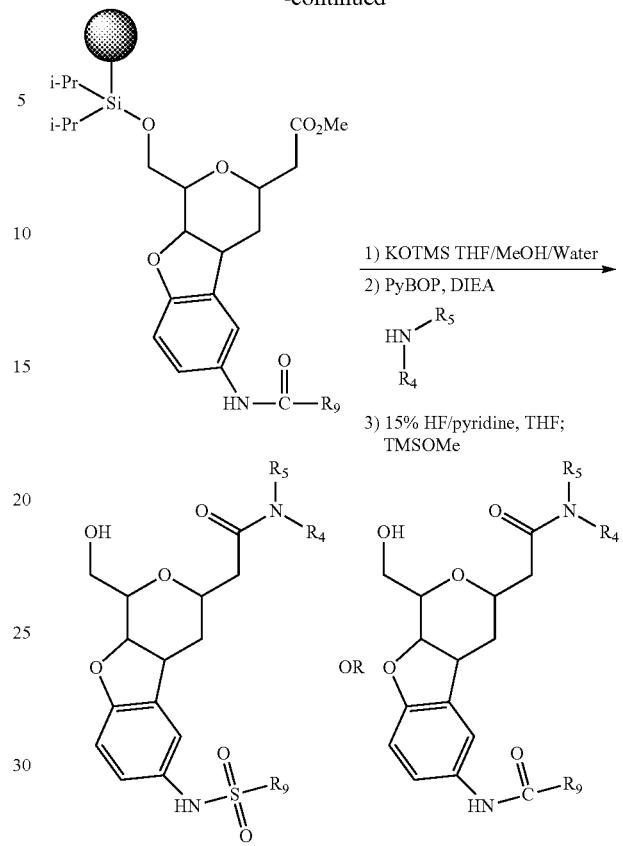
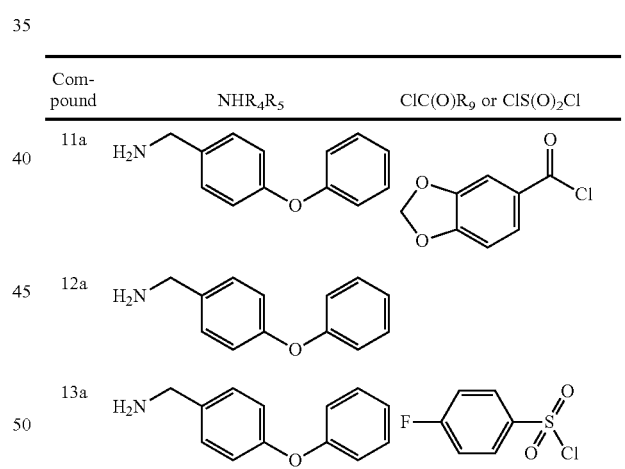

Example 2

Identification of Compounds that Induce TRIM Upregulation

An exploratory high-throughput screen of 16,000 compounds was performed to identify small molecule inducers of TRIB1 expression. The screen was performed in the human hepatocellular carcinoma (hepatoma) cell line, HepG2. HepG2 cells were chosen for their competence in key aspects of cholesterol metabolism. Specifically, the cells produce VLDL and scavenge LDL, and furthermore, VLDL production can be downregulated by TRIB1 overexpression, as measured by reduced secretion of ApoB 100. Multiple chemical libraries were combined for this screen, including 2240 compounds from BIOA (Bioactives Collection), 960 compounds from NATP (Natural Products—purified Collection), 3200 compounds from COMC (Commercially Available Collection), and 9600 compounds from the Broad DOS (Diversity Oriented Synthesis) Informer Set (Nielsen and Schreiber, 2007). A total of 16,000 chemical compounds were assessed for their ability to modulate TRIB1 gene expression.

In the primary screen, HepG2 cells were plated in 384-well plates at 2000 cells per well and incubated for 20 hours with each compound in duplicate at 10 microM concentration. Then RNA was isolated, reverse-transcribed to cDNA, and stored at −80° C. Expression levels of TRIB1 and other target genes, such as SORT1 and PCSK9, were determined by quantitative PCR. Relative gene expression level was normalized to expression of the housekeeping gene, GAPDH. A "hit" was defined as those compounds that caused a greater than 2-fold increase in relative target gene expression when normalized to GAPDH expression, compared to DMSO-treated control. Using these criteria, 130 hits were identified for TRIB1 (0.8% hit rate).

Figure 1B:
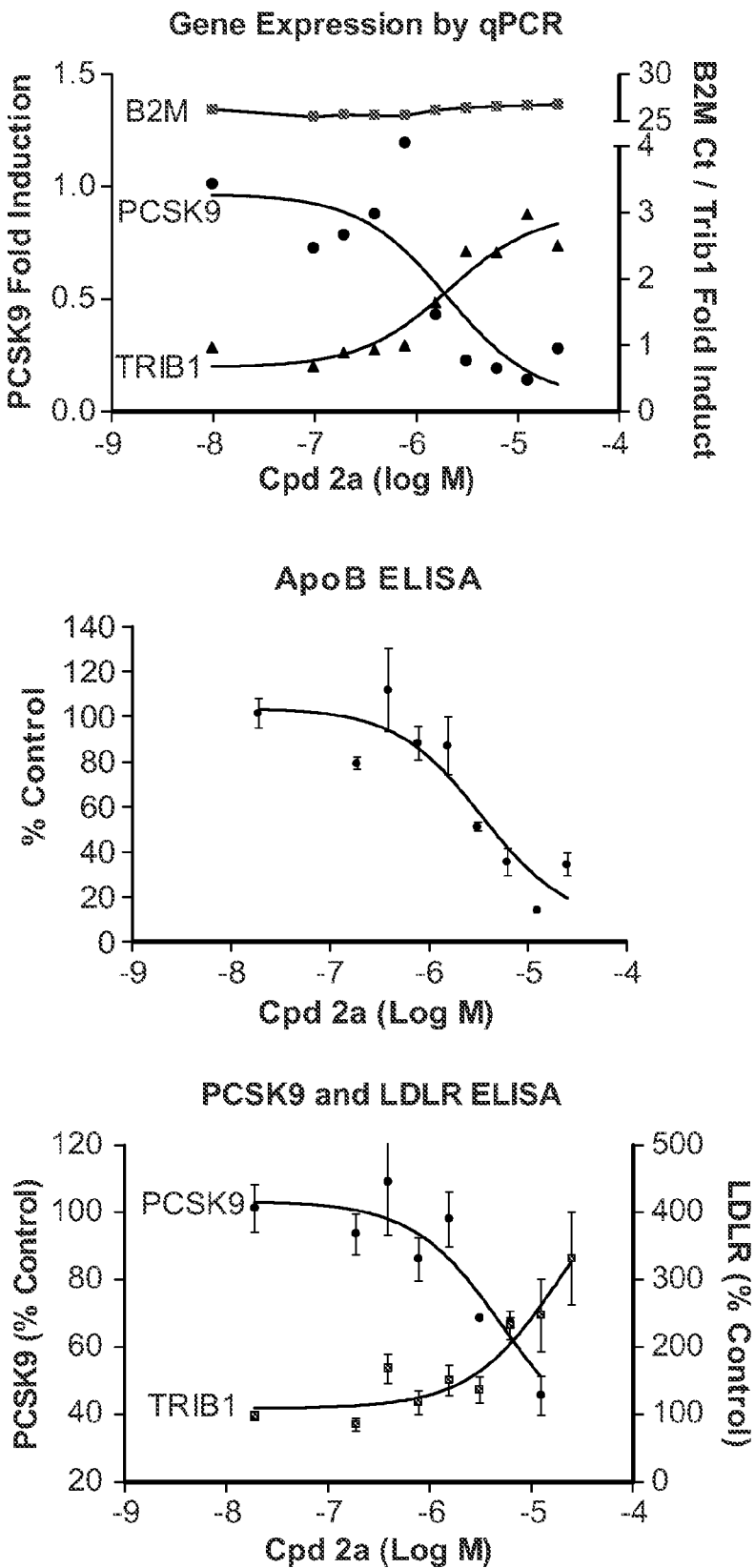

For secondary confirmation, the primary hits were screened in another hepatoma cell line, Huh-7, for their effect on TRIB1 gene expression by qPCR analysis. In Huh-7 cells, 66 hits were identified where relative TRIB1 expression was greater than 2-fold when normalized to GAPDH compared to controls. About 40% (25/66) of the confirmed TRIB1 hits were from the internal Broad DOS Collection. These compounds include compounds 12a and 2a. FIG. 1 shows representative qPCR data comparing induction of relative TRIB1 expression upon various doses of compound treatments in HepG2 cells.

It has been discovered herein that the TRIB1 inducers consistently upregulate expression of LDLR and downregulate expression of PCSK9 and expression of cholesterol biosynthetic genes HMGCR and HMGCS as well as triglyceride-related genes FASN and SCD1. The detailed profile of activities for the prototypical tricyclic glycal compound 2a and the prototypical benzofuran compound 12a is shown in FIG. 1. As expected from the TRIB1 inducing activity both compounds with reassuring reciprocity inhibited secretion of apoB into the media (FIG. 1). Unexpectedly however, we observed that both compounds were equally potent in inhibiting the expression of PCSK9 mRNA and secretion of PCSK9 protein into the media reaching 70% inhibition at the maximal dose tested (FIG. 1). Furthermore, treatment with either 2a or 12a led to induction of LDLR expression and to 3-fold increase of the LDL receptor protein in the cell (FIG. 1). None of the compounds showed signs of cell toxicity in a counter-screen for cell viability (e.g., CellTiter-Glo, Promega; data not shown).

Many of the identified hits from the Broad DOS Collection exhibited stereochemical structure-activity relationship. Compound 4a stereoisomers were tested for TRIB1 upregulation after 20 hours of treatment by qPCR analysis (FIG. 2). Only 2 of the 6 stereoisomers (SSR(3B) and SSS(4B)) were active, or had the ability to upregulate TRIB1 expression. Such stereo-dependency of compound activity indicates that the biological activity comes from a specific target binding event rather than form non-specific interactions.

Example 3

L-1000 Profiling Confirms TRIM Induction

Induction of the TRIB1 transcript levels by the screening hits was confirmed by alternative transcript quantification methodology through L-1000 profiling. The L-1000 assay is a novel mRNA expression profiling technique based on a reduced representation of the genome whereby 1,000 carefully-selected "landmark" transcripts are monitored, and from which the remainder of the transcriptome can be computationally inferred. TRIB1 is one of the 1000 landmark genes. In this method, transcript levels are measured by bead-based Luminex technology and normalized against all measured transcripts (quantile normalization) rather than against a single housekeeping gene, as it is done in the qPCR approach. Briefly, the method involves ligation-mediated amplification (LMA) using locus-specific probes engineered to contain unique molecular barcodes, universal biotinylated primers, and 5.6-micron optically-addressed polystyrene microspheres coupled to capture probes complementary to the barcode sequences. After hybridizing the LMA products to a mixture of beads and staining with streptavidin-phycoerythrin, the hybridization events are detected using a two-laser flow cytometer, whereby one laser detects the bead color (denoting transcript identity), and the other laser detects the phycoerythrin channel (denoting transcript abundance). The resulting assay is a 1,000-plex assay detectable in a single well of a 384-well plate.

A total of 135 compounds were tested in the L-1000 assay: 66 of the confirmed TRIB1 inducers, 11 inactive stereoisomers of DOS hits, 28 random TRIB1 inactive compounds, and 30 TRIB1 inhibitors. Four CMAP control compounds were used as controls. HepG2 cells were treated with the compounds for 6 hours or 24 hours, and at 2 different doses (25 and 6.25 µM). Compounds were clustered based on the L-1000 transcription profiles and are linked to CMAP control compounds and profiles generated from the primary screen. In the L-1000 analysis, TRIB1 inducers consistently induced at least a 1 or 2 $\log_2$ Fold Change (LFC) in TRIB1 expression after 6 and 24 hours of treatment (see FIG. 3 for HepG2 results). TRIB1 inhibitors also exhibited a decrease in TRIB1 expression. Furthermore, the additional expression data for other members of the cholesterol and lipoprotein metabolism pathways from the L-1000 assay provided insight into potential mechanisms of action.

Example 4

Secondary Assays

Additional secondary assays were performed in HepG2 cells to further characterize the cellular response to treatment with select confirmed TRIB1 inducer hits. The results of the ELISA, CTG, and qPCR secondary assays are summarized in Table B. For all secondary assays, the experiments were performed using powders of freshly purified compounds.

To further characterize the relationship of TRIB1 induction and PCSK9 reduction, ELISAs were performed to measure the levels of secreted ApoB, PCSK9, and LDLR. TRIB1 overexpression has previously been shown to reduce ApoB production. As predicted treatment with TRIB1 inducer hits caused a decrease in ApoB levels detected by ELISA. In parallel effort, 3200 BIOA and NATP compounds were screened for PCSK9 expression inhibitors. Hits were defined as inducing greater than 3-fold downregulation of PCSK9, and 3.8% of the screened compounds were confirmed as hits. In contrast, a very high proportion of the confirmed TRIB1 inducers (45/65 of the primary hits, or 70%) also inhibited PCSK9 expression. In further experiments, a strong correlation was confirmed between TRIB1 induction and PCSK9 repression in DOS Collection hits. ELISA analysis confirmed that treatment with TRIB1 inducers reduced the PCSK9 protein levels. LDLR protein levels were also analyzed by ELISA to determine whether compounds that modulate both TRIB1 and PCSK9 had any effect on LDLR protein levels. Results indicate that generally, LDLR protein levels were increased.

Cell viability was determined using a Cell Titer Glo (CTG) assay (Invitrogen) after treatment with TRIB1 inducer compounds. In this assay, the number of viable cells in culture is based on quantitation of ATP, which indicates metabolically active cells. Addition of the reagent results in cell lysis and generation of a luminescent signal proportional to the amount of ATP present, which is directly proportional to the number of viable, metabolically active cells present in culture. Most TRIB1 inducer compounds had no significant effect on cell viability.

Further analysis of the expression levels of various proteins in the cholesterol and triglyceride biosynthetic pathways in response to TRIB1 inducer treatment was performed. In particular, transcript levels of additional lipoprotein metabolism pathway proteins SCAP, SREBF1, SREBF2, HMGCR, HMGCS, SCD1, FASN and MTTP were assessed by qPCR, along with TRIB1, LDLR, and PCSK9. The gene expression profile for the same subset of genes was also assessed after treatment with the statin atorvastatin (Lipitor), commonly used in therapy for hypercholesterolemia and other cardiovascular diseases. Strikingly, the selected TRIB1 inducers were found to downregulate the transcript levels for genes in the cholesterol (HMGCS, HMGCR) and triglyceride (FASN, SCD1) biosynthetic pathways. This transcriptional response pattern is very different from the response profile produced by statins (as evidenced by the profile from atorvastatin), where transcript levels for HMGCR, FASN, and SCD1 are upregulated.

In addition, analysis of the transcriptional profiling data obtained from HepG2 cells treated with compounds 12a and 2a revealed that the treatment with 10 μM compounds for 24 hours down regulates expression of APOC3 gene. Expression of APOC3 is associated with increased levels of triglycerides in plasma and carriers of APOC3 gene null mutation have low levels of triglycerides and are protected from cardiovascular disease (Pollin et al., Science, 322: 1702, 2008).

The kinetics of the modulation of TRIB1, LDLR, PCSK9 and MTTP gene expression after treatment by select TRIB1 inducer compounds was monitored by qPCR analysis (FIG. 4). RNA was extracted from cells at various timepoints over 28 hours of treatment (0, 2, 4, 6, 8, 24, 28 hours). Specifically, compounds 12a and 14a induced transcriptional responses over time similar to those produced by berberine, a plant alkaloid used in Chinese medicine. Berberine has been demonstrated to reduce blood LDL-C in animal models and hypercholesterolemic patients (Kong et al., Nature Medicine, 10:1344, 2004.) Expression levels of TRIB1, LDLR, PCSK9 and MTTP were calculated as the fold change, as normalized to GADPH control and vehicle controls. Both compound 12a and compound 14a induce TRIB1 and LDLR and repress PCSK9 and MTTP expression with similar kinetics and similar fold change as berberine Importantly, both compounds induce these gene expression changes at much lower concentrations than berberine. Indeed, the benzofuran compound 12a and the tricyclic glycal compound 14a are 5- and 10-fold more potent than berberine, respectively. This increased potency indicates the potential therapeutic efficacy of such compounds for treatment of cardiovascular diseases, particularly hypercholesterolemia and related conditions.

The cell surface expression of LDLR (Low Density Lipoprotein Receptor) is analyzed by FACS analysis. Treatment with TRIB1 inducer compounds results in increased level of LDL receptor proteins presented on the cell surface of HepG2 cells.

Based on the results of the secondary assays, the selected TRIB1 inducers were found to stimulate a unique signature of cellular responses in HepG2 cells without affecting cellular ATP levels or cell viability. This unique signature of cellular responses includes: 1) upregulation of transcript levels for TRIB1; 2) downregulation of transcript levels for PCSK9; 3) upregulation of transcript levels for LDLR; 4) downregulation of transcript levels for genes in the cholesterol biosynthetic pathway (e.g., HMGCS, HMGCR); 5) downregulation of transcript levels for genes in the triglyceride biosynethetic pathway (e.g., FASN, SCD1); 6) downregulation of transcript levels of MTTP; 7) down regulation of transcript levels of APOC3; 8) decreased level of secreted ApoB 100 protein; 9) decreased level of secreted PCSK9 protein; or 10) increased level of LDLR in cells. Each of the responses listed above has individually been linked to the reduction of LDL-C in circulation, therefore, indicating the efficacy and use for treating, preventing, and/or alleviating one or more symptoms of a cardiovascular disease or related disorder.

Example 5

Rate of LDL Uptake in Cells

Figure 6A:
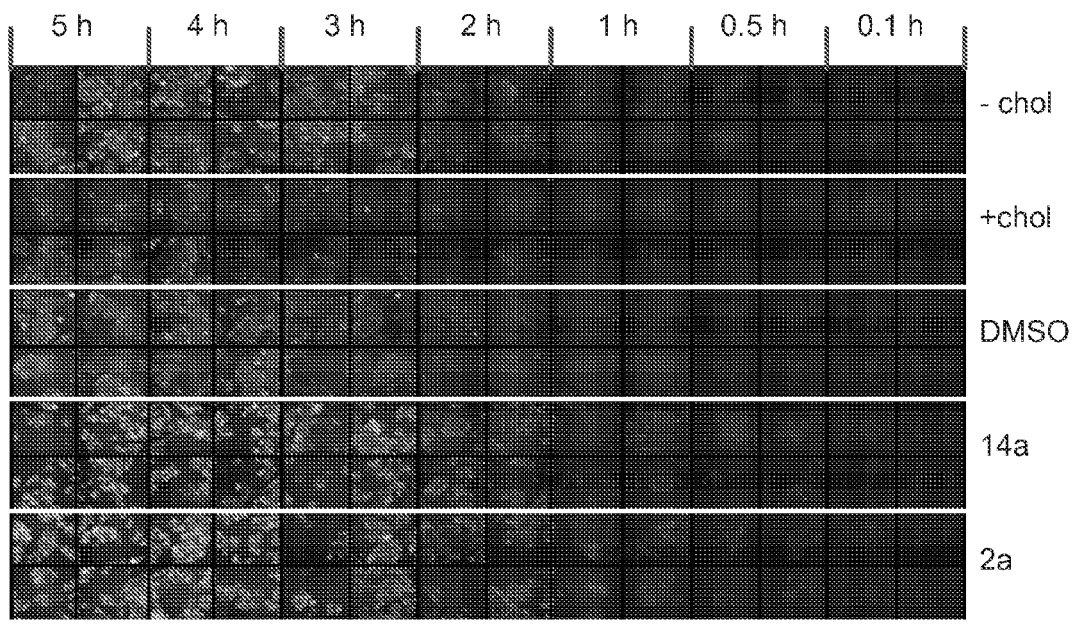
FIG. 6A is an image that shows fixed cells at various times after addition of BODIPY-FL LDL.
Figure 6B:
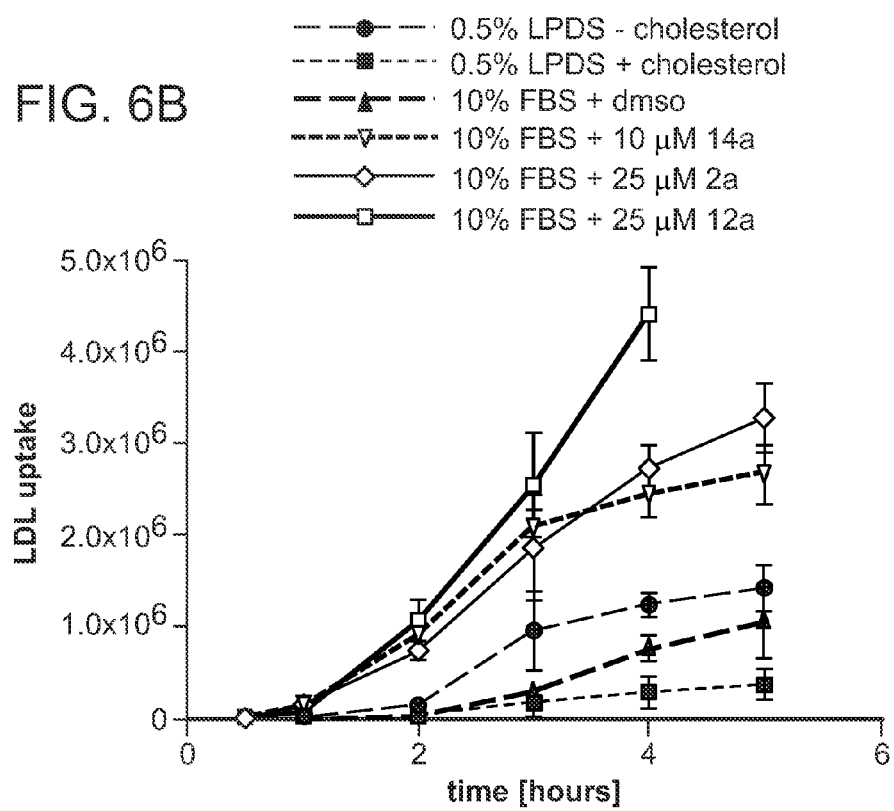
FIG. 6B is a graph which shows BODIPY-FL LDL uptake over time.

To further evaluate functional consequences of the induction of LDLR expression, the rate of LDL uptake was measured in cells treated with 2a, 14a and 12a. TRIB1 inducers increase the rate of LDL uptake. HepG2 cells grown under standard culture conditions (10% FBS) were treated for 20 hours with compounds 2a, 14a and 12a at indicated concentrations and the uptake of BODIPY-FL conjugated LDL particles was monitored for 5 hours using high content microscopy. To control for regulation of LDL uptake by cholesterol, cells were grown in media depleted for (0.5% LPDS—lipoprotein deficient serum) or supplemented with cholesterol (0.5% LPDS plus cholesterol (10 mg/ml cholesterol and 1 mg/ml 25-OH cholesterol)). All three compounds resulted in the robust increase in the rate of the LDL uptake, which exceeded the increase in the rate of LDL uptake induced by depletion of cholesterol in the media (FIG. 6). FIG. 6A shows images of cells fixed with 3% paraformaldehyde taken using IXM microscope (Molecular Devices) at various times after addition of BODIPY-FL LDL (5 mg protein/ml) to media. FIG. 6B shows BODIPY-FL LDL uptake, which was quantified by measuring relative intensity of the BODIPY-FL dye and Hoechst-33342 stained nuclei using the ImageXpress Micro software (Molecular Devices).

Example 6

Kinetics of Gene Expression Compared to Statins

Figure 7:
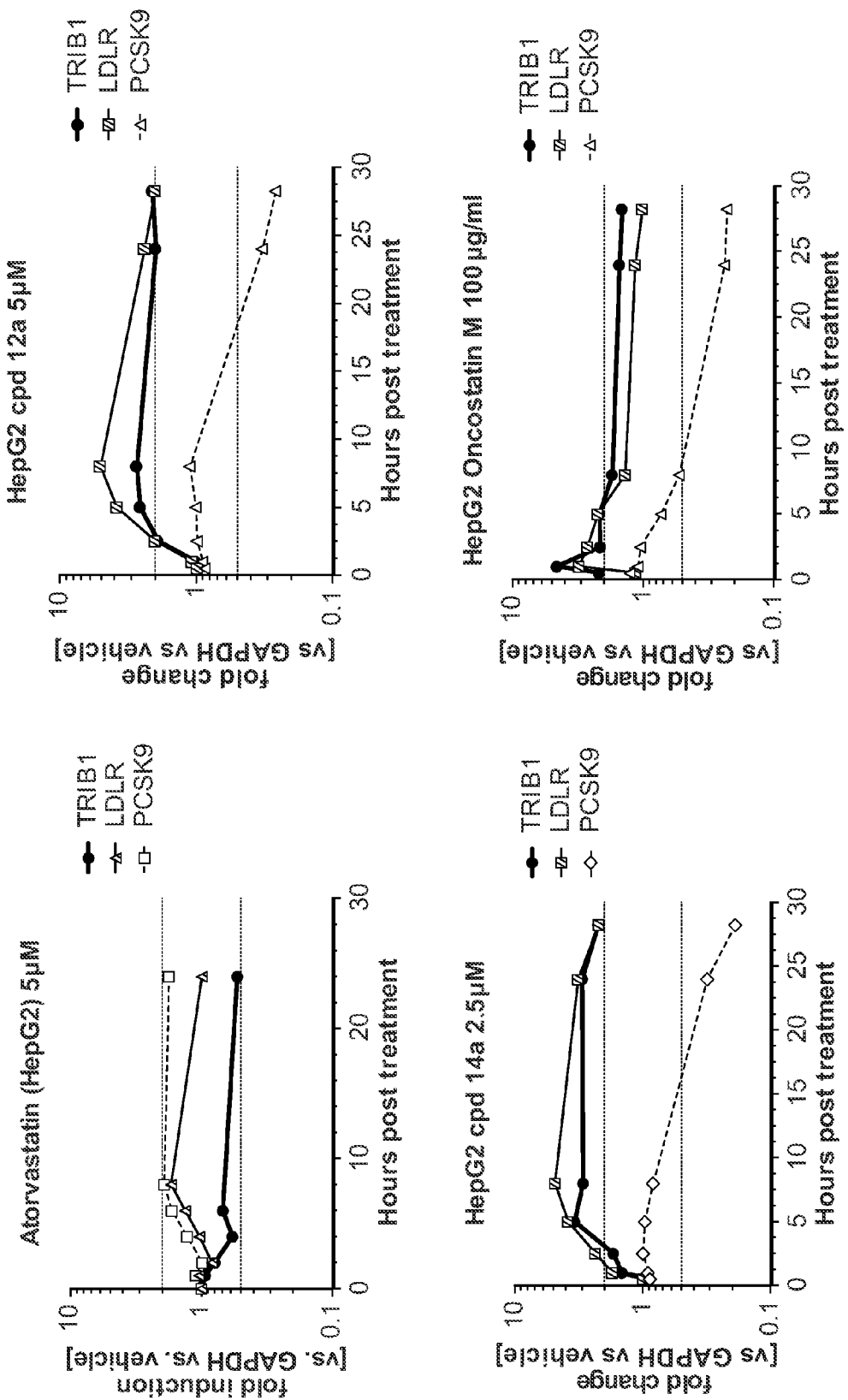
FIG. 7 is a series of graphs that shows the fold change of expression for TRIB1 (circle); LDLR (square); and PCSK9 (triangle) after treatment with atorvastatin, compound 14a, 12a, and oncostatin at indicated concentrations.

The pattern of responses of compounds of the invention to TRIB1 induction bears potential therapeutic implication as the change in LDLR expression appears to be decoupled from changes in expression of PCSK9 and the cholesterol metabolic genes, suggesting an SREBF2 independent regulatory mechanism. Confirmation of this observation was obtained in a time course experiment (FIG. 7). In contrast to atorvastatin, which induced in a coordinated fashion approximately a 2-fold increase of LDLR and PCSK9 mRNA levels and did not significantly affect expression of TRIM, compounds 2a, 12a and 14a robustly induced TRIB1 and LDLR expression but strongly reduced PCSK9 expression. Maximal increase in LDLR and TRIB1 levels occurred after 6-8 h of exposure whereas the decrease in PCSK9 level was a late response and occurred after 24 h of treatment with the compounds of the invention. Oncostatin M (OSM) was also included in this analysis, as it was previously demonstrated to up-regulate LDLR and down-regulate PCSK9 expression in HepG2 cells (A. Cao, M. Wu, H. Li, J. Liu, J Lipid Res 52, 518 (March, 2011)). Response to OSM resulted in similar pattern of changes in the transcript levels, except the peak responses of LDLR and TRIB1 occurred one hour after the treatment (FIG. 7). FIG. 7 is a series of graphs that shows the kinetics of gene expression modulation over a 28 hour time course after treatment with Atorvastatin, 14a, 2a and oncostatin M at indicated concentrations. Fold change of expression (relative expression normalized to GAPDH, compared to vehicle control) was calculated for the following genes: TRIB1 (circle); LDLR (square); and PCSK9 (triangle).

Example 7

Figure 5:
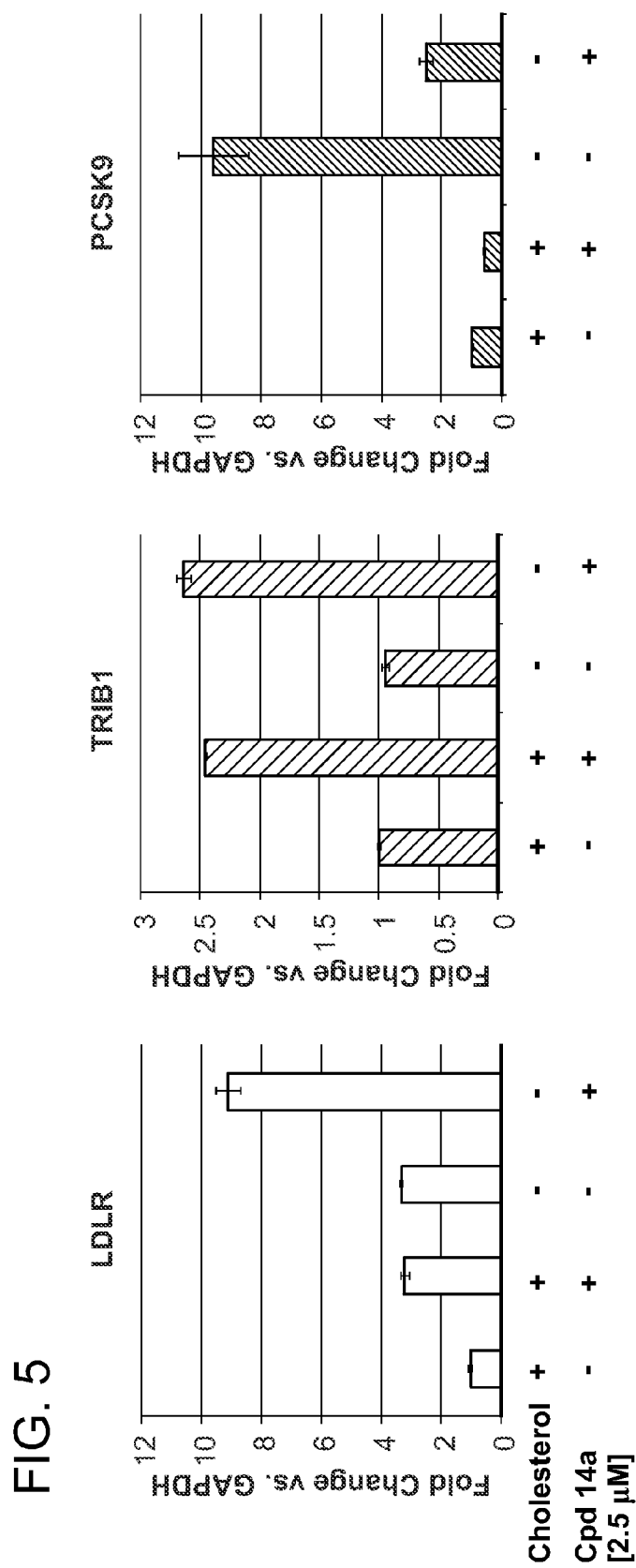
FIG. 5 is a series of bar graphs that shows effects of cholesterol starvation on expression of TRIB1, LDLR and PCSK9 and additive effect of Compound 14a treatment (2.5 µM) and cholesterol starvation on expression of LDLR and PCSK9. Cholesterol starvation achieved by incubation of HepG2 cells in 0.5% lipoprotein deficient serum (LPDS) for 24 hours did not affect TRIB1 expression.

Effects of Cholesterol Depletion on TRIM and Cholesterol Metabolism Gene Expression and on Activity of TRIM Inducers In hepatic cells, cholesterol starvation induces coordinated response mediated by SREBF transcription factors. SREBFs activation results in the induction of genes in the cholesterol biosynthetic pathway (e.g. HMGCR, HMGCS) and in cholesterol uptake (LDLR) as well as the induction of PCSK9 transcription, which in turn results in LDL receptor degradation and subsequent downregulation of cholesterol uptake. The effects of cholesterol starvation on induction of TRIB1 as well as known SREBF targets LDLR and PCSK9 were examined in the presence and absence of the TRIB1 inducers (FIG. 5). The effects of 12a and 14a on HepG2 cells under conditions of cholesterol depletion were tested. Cholesterol depletion achieved by incubation of HepG2 cells in 0.5% lipoprotein deficient serum (LPDS) for 24 hours did not affect TRIB1 expression. After a 24 h incubation in the lipoprotein depleted media the levels of LDLR mRNA and PCSK9 mRNA were measured. Results are shown in FIG. 5. For compound 14a levels of LDLR and PCSK9 increased 3-fold and 9-fold, respectively, whereas TRIB1 message remained unchanged compared to cholesterol supplemented media (10 mg/ml cholesterol and 1 mg/ml 25-OH-cholesterol). Treatment with 2.5 µM 14a increased LDLR signal further to 9-fold over the non-depleted control and decreased PCSK9 mRNA 3.8-fold below the level induced by cholesterol starvation demonstrating that effects of 14a are additive with effects of cholesterol depletion. Similar results were also obtained for 12a (data not shown). In contrast to LDLR and PCSK9 transcript levels, the level of TRIB1 transcripts was not changed in response to cholesterol deprivation. The TRIB1 inducers remained active (i.e., they did induce TRIB1 and LDLR and reduce PCSK9 transcript levels) regardless of the cholesterol starvation status of the cell. Effects of TRIB1 inducers on LDLR and PCSK9 are additive suggesting that, unlike in case of statins (HMGCoA reductase inhibitors), their mechanism of action is independent of SREBF activity.

Example 7

Statin Combination Effects

The LDLR inducing effects of 14a, 2a and 12a were not suppressed by the pharmacologically induced cholesterol depletion in cells treated with HMG-CoA reductase inhibitors. As shown in FIG. 8A combination of an overnight treatment with simvastatin with subsequent treatment with compounds 2a, 14a and 12a had additive effect on the induction of LDLR expression. The compounds also potently reduced expression of PCSK9 that was stimulated by pretreatment with atorvastatin (FIG. 8B). These results further support the conclusion that the TRIB1 inducing compounds of the invention elicit their effects on cholesterol metabolism through an SREBF-2 independent mechanism.

Example 8

Determination of Half Maximal Effective Concentration

Analogs from the tricyclic glycal library were found to induce TRIB1 and LDLR transcript levels with improved potency. For compounds 14a, 15a, 16a, and 17a the half maximal effective concentration ($EC_{50}$) was found to be less than 1 µM.

Example 9

Effect on the Rate of Triglyceride Formation

Figure 9:
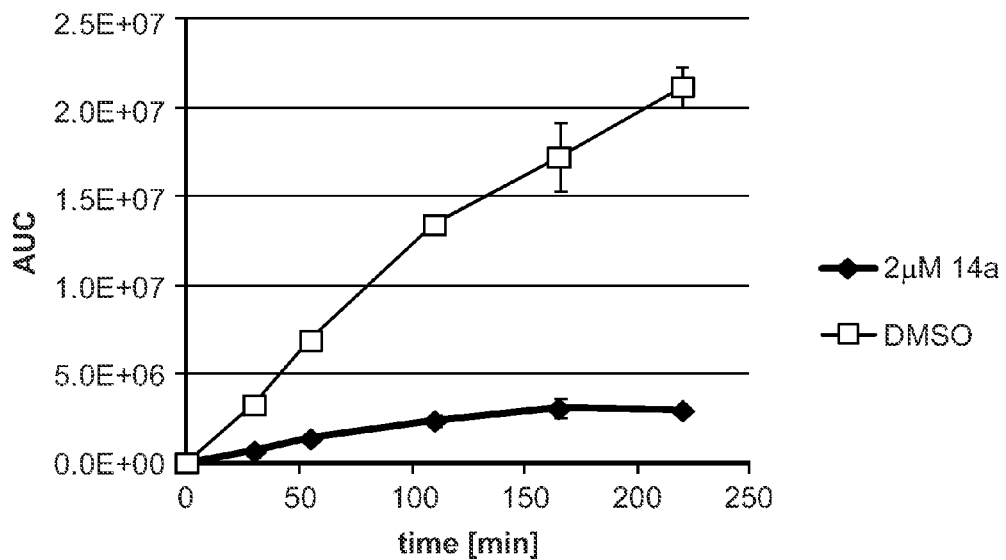

The overexpression of TRIB1 cDNA in HepG2 cells has been shown to down regulate the expression of triglyceride biosynthetic genes and consequently to inhibit the incorporation of the tritiated glycerol into triglycerides (Burkhardt et al., *J Clin Invest* 120, 4410 (December, 2010)). To evaluate the effect of the TRIB1 inducers on the rate of triglyceride synthesis we incubated HepG2 cells with 2 µM compound 14a for 24 hours and then incubated the cells with stable isotope labeled glycerol (13C3-D5-glycerol) for varying amounts of time. The incorporation of the 13C3-D5-glycerol into triglycerides was quantified in the lipid extracts by high resolution mass spectroscopy. Numerous species of triglycerides were monitored and for all of them we observed 5-fold to 10-fold reduction in the formation rate in the cells treated with compound 14a in comparison to cells treated with DMSO. A graph showing incorporation of 13C3-D5-glycerol into one of the species of triacylglcerol, 13C3-D5-C50:2 TAG, is shown in FIG. 9.

Example 10

Rodent Models

Rodent models of hypercholesterolemia and cardiovascular disease are utilized to determine the efficacy of the selected TRIB1 inducers for treating, preventing, and/or alleviating one or more symptoms of hypercholesterolemia or cardiovascular disease. Selected TRIB1 inducers are administered to rodents with hypercholesterolemia over a period of time. Levels of TRIB1, PCSK9, LDL, FASN and other transcripts and/or protein are measured throughout the treatment to monitor response to the TRIB1 inducers. Testing the levels of blood lipids, particularly triglycerides and LDL cholesterol, provides the measure of efficacy of selected compounds.

TABLE B

Summary of results from secondary assays for select TRIB1 inducer compounds

| | ELISA | | | CTG | qPCR | | | | | | | | | |
|---|---|---|---|---|---|---|---|---|---|---|---|---|---|---|
| Compound | ApoB | LDLR | PCSK9 | CTG | TRIB1 | SCAP | SREBF1 | SREBF2 | PCSK9 | LDLR | HMGCR | HMGCS | FASN | SCD1 |
| Atorvastatin | X | A | A | N | N | N | N | A | B | B | N | A | A | A |
| 12a | Y | B | Y | N | A | X | Y | Y | Y | A | Y | Y | Y | Y |
| 11a | Y | B | Y | Y | B | N | Y | Y | Y | B | Y | Y | Y | Y |
| 13a | Y | X | Y | N | B | N | N | N | Y | B | Y | Y | X | Y |
| 7a | Y | B | Y | N | B | N | N | N | Y | B | Y | Y | X | X |
| 9a | Y | B | Y | X | B | N | N | B | Y | B | Y | Y | Y | Y |
| 10a | Y | N | X | N | B | N | N | N | Y | B | Y | Y | X | Y |
| 8a | Y | B | X | N | B | N | N | N | Y | B | Y | Y | X | X |
| 6a | Y | A | Y | N | B | N | N | N | Y | A | N | Y | Y | Y |
| 3a | Y | B | X | N | B | N | N | B | Y | B | Y | Y | Y | Y |
| 1a | Y | B | Y | N | B | N | N | N | Y | B | Y | Y | X | X |
| 4a | Y | A | X | N | B | X | X | X | Y | A | X | Y | Y | X |
| 2a | Y | B | Y | N | B | N | N | N | Y | B | Y | Y | Y | Y |

| | | |
|---|---|---|
| A | Increase <2-fold | |
| B | Increase >2-fold | |
| X | Decrease <2-fold | |
| Y | Decrease >2-fold | |
| N | No significant change | |

TABLE C

Summary of the pathway analysis of the Affymetrix transcriptional profiling data obtained from cells treated with compound 2a.

| Name | Total Entities | Overlap | Percent Overlap | Overlapping Entities | p-value | # |
|---|---|---|---|---|---|---|
| 10 uM at 6 hrs Pathway Analysis | | | | | | |
| Cell cycle | 140 | 25 | 17 | FOS, CDKN1A, MYC, GSK3B, JUN, CDK6, MDM2, SMAD3, BRCA1, GADD45B, CCNB1, AURKA, H2AFX, CDC6, CDT1, GMNN, TFDP1, CDKN2C, WEE1, CDC7, CENPA, BTRC, MED13, CDCA3, TFDP2 | 0.0001 | 1 |
| Metabolism of glycerophospholipids and other lipids | 152 | 3 | 1 | LCLAT1, AGPAT3, MBOAT7 | 0.0027 | 2 |
| IL11R->STAT3 signaling | 6 | 3 | 50 | STAT3, IL11, IL6ST | 0.0110 | 3 |
| Oncostatin R->STAT3 signaling | 6 | 3 | 50 | STAT3, IL6ST, OSMR | 0.0110 | 4 |
| Tight Junction Assembly (Occludin) | 38 | 8 | 21 | CTTN, VASP, ILK, ACTN1, PTEN, VCL, TJP2, ZAK | 0.0130 | 5 |
| Single-Strand Mismatch DNA Repair | 19 | 5 | 26 | MSH2, PMS1, MSH6, FEN1, EXO1 | 0.0193 | 6 |
| ICAM2->CTNNB/FOXO/STAT3 signaling | 13 | 4 | 30 | GSK3B, FOXO1, STAT3, FOXO3 | 0.0220 | 7 |
| EGFR/ERBB->22 STAT signaling | 20 | 5 | 25 | TGFA, AREG, STAT3, EREG, STAT5B | 0.0257 | 8 |
| InsulinR->STAT signaling | 9 | 3 | 33 | STAT3, SH2B1, STAT5B | 0.0381 | 9 |
| Apoptosis | 93 | 13 | 13 | TNFRSF1A, CYCS, BID, TNFSF10, XIAP, BCL2L11, MDM2, BIRC3, MCL1, FADD, INFRSF10A, BAD, B1K | 0.0496 | 10 |
| EGFR->ZNF259 signaling | 10 | 3 | 30 | TGFA, AREG, EREG | 0.0511 | 11 |
| 10 uM at 24hrs Pathway Analysis | | | | | | |
| omega-6-fatty acid metabolism | 97 | 5 | 5 | ELOVL2, HSD17B12, AKR1B10, TECR, ELOVL5 | 0.0003 | 1 |
| Cell cycle | 140 | 46 | 32 | TGFB1, MYC, GSK3B, CCNE1, CDK2, JUN, SMAD2, CDK4, CDK6, CHEK1, ESPL1, MDM2, CHEK2, SMAD3, GADD45A, BRCA1, CCNA2, SKP2, BIRC5, GADD45B, AURKB, CCNB1, CCND3, CDKN2B, SFN, SMAD4, CCNB2, H2AFX, CDC6, MAD2L1, FBX05, | 0.0005 | 2 |

TABLE C-continued

Summary of the pathway analysis of the Affymetrix transcriptional profiling data obtained from cells treated with compound 2a.

| | | | | | | | |
|---|---|---|---|---|---|---|---|
| | | | | CDC25A, CDT1, GMNN, TFDP1, CDKN2C, CDC45, CCNE2, CCNC, WEE1, CDC7, CHFR, CENPA, LATS1, CDCA3, TFDP2 | | | |
| Vitamin K metabolism | 36 | 3 | 8 | PROS1, F7, GGCX | 0.0015 | 3 |
| EGFR/ERBB2->CTNNB signaling | 13 | 7 | 53 | HBEGF, SRC, EGFR, CTNNB1, AREG, SHC1, EREG | 0.0032 | 4 |
| EGFR/ERBB ->STAT signaling | 20 | 9 | 45 | HBEGF, SRC, EGFR, JAK2, AREG, SHC1, STAT5A, EREG, STAT5B | 0.0039 | 5 |
| omega-3-fatty acid metabolism | 107 | 4 | 3 | ELOVL2, HSD17B12, TECR, ELOVL5 | 0.0043 | 6 |
| TGFBR/BMPR->SMAD2/3 signaling | 14 | 7 | 50 | TGFB1, SMAD2, SMAD3, BMPR2, SMURF2, SMAD4, SMURF1 | 0.0055 | 7 |
| HGFR->STAT signaling | 8 | 5 | 62 | SRC, JAK2, STAT5A, METSTAT5B | 0.0059 | 8 |
| TNFRSF1A->STAT signaling | 12 | 6 | 50 | TNFRSF1A, JAK2, STAT5A, STAT6, STAT5B, JAK1 | 0.0103 | 9 |
| EGFR->CTNND signaling | 12 | 6 | 50 | HBEGF, SRC, EGFR, AREG, SHC1, EREG | 0.0103 | 10 |
| DNA Replication | 29 | 12 | 41 | DNA2, PCNA, CDC6, CDT1, GMNN, CDC45, CDC7, FEN1, POLA1, WDHD1, POLE, ERH | 0.0114 | 11 |
| EGFR->ZNF259 signaling | 10 | 5 | 50 | HBEGF, EGFR, AREG, EREG, ZNF259 | 0.0194 | 12 |
| LIFR->STAT5A signaling | 10 | 5 | 50 | JAK2, LIF, STAT5A, LIFR, JAK1 | 0.0194 | 13 |
| IL6ST->STAT5B signaling | 7 | 4 | 57 | SRC, JAK2, STAT5B, JAK1 | 0.0215 | 14 |
| IL4R->STAT signaling | 7 | 4 | 57 | STAT5A, STAT6, IL4R, JAK1 | 0.0215 | 15 |
| ErythropoietinR->STAT signaling | 7 | 4 | 57 | EPO, JAK2, STAT5A, STAT5B | 0.0215 | 16 |
| Ubiquinoine biosynthesis | 35 | 2 | 5 | COQ7, COQ3 | 0.0215 | 17 |
| Ubiquinoine biosynthesis (human) | 35 | 2 | 5 | COQ7, COQ3 | 0.0215 | 18 |
| Ubiquinoine biosynthesis (rat) | 35 | 2 | 5 | COQ7, COQ3 | 0.0215 | 19 |
| DDR1->NF-kB signaling | 14 | 6 | 42 | MAPK14, COL2A1, SHC1, DDR1, MAP3K7, COL5A2 | 0.0245 | 20 |
| Single-Strand Mismatch DNA Repair | 19 | 8 | 42 | MSH2, PCNA, PMS1, MSH6, FEN1, EXO1, LIG1, POLE | 0.0336 | 21 |
| ActivinR->SMAD2/3 signaling | 23 | 8 | 34 | SMAD2, SMAD3, INHBB, BMP6, ACVR2B, SMURF SMAD4, SMURF1 | 0.0364 | 22 |
| EphrinB->JUNsignaling | 19 | 7 | 36 | MAPK14, PTK2, MAPK8, JUN, BCAR1, MAP3K7, MAP2K6 | 0.0365 | 23 |
| 1L31R->STAT signaling | 8 | 4 | 50 | JAK2, STAT5A, JAK1, OSMR | 0.0372 | 24 |
| IFNGR ->STAT signaling | 8 | 4 | 50 | JAK2, STAT5A, JAK1, IFNGR2 | 0.0372 | 25 |
| Fibronectin R->ICAP-1A/MYC signaling | 5 | 3 | 60 | MYC, ITGB1, ITGB1BP1 | 0.0416 | 26 |
| TNFR->NF-kB signaling | 32 | 10 | 31 | MAPK14, TNFRSF1A, FAS, TNFSF10, TNFRSF10B, MAP3K7,TNFRSF10A, MAP2K6, TNFSF13, CAMLG | 0.0419 | 27 |
| Apoptosis | 93 | 27 | 29 | TNFRSF1A, FAS, BAX, CASP2, CASP7, CYCS, MAPK8, APP, TNFSF10, XIAP, PARP1, BCL2L1, MDM2, CHEK2, MCL1, BIRC5, TNFRSF10B, CFLAR, DFFB, BCL2L2, MAP3K7, TNFRSF10A, SPTAN1, CASP10, CASP8AP2, GAS2, FAF1 | 0.0454 | 28 |
| Heme biosynthesis | 54 | 2 | 3 | CYCS, COX15 | 0.0482 | 29 |
| Lipid metabolism | | | | APOB3 | | |

TABLE D

Activity Profile of Compounds of the Invention

| Compound no. | SSAR | qPCR 6Hr (EC50 uM) TRIB1 up-regulation | qPCR 6Hr (EC50 uM) LDLR up-regulation | qPCR 24 Hr (EC50 uM) PCSK9 down-regulation | ELISA 24 Hr (EC50 uM) ApoB decrease | ELISA 24 Hr (EC50 uM) PCSK9 decrease | ELISA 24 Hr (EC50 uM) LDLR increase |
|---|---|---|---|---|---|---|---|
| 14a | Control | A | B | A | C | B | A |
| 17a | RSS | B | B | A | A | A | C |
| 18a | RSS | C | C | B | B | B | D |
| 19a | RSS | D | C | C | D | C | D |
| 20a | RSS | D | D | B | F | C | C |
| 21a | RSS | D | E | B | F | C | E |
| 22a | SSS | D | D | C | NC | D | C |
| 23a | RSS | D | D | C | NC | C | B |
| 24a | SSS | E | D | ND | NC | D | E |

NC-No change
ND-Not determined

The data in Table D were obtained using methods and assays described in Examples 2 and 4. The data is presented whereby the letter "A" means the compound has an $EC_{50}$ between 0.0000001 µM≤0.5 µM, the letter "B" means the compound has an $EC_{50}$ between 0.51 µM≤1.0 µM, the letter "C" means the compound has an $EC_{50}$ between 1.1 µM≤2.0 µM, the letter "D" means the compound has an $EC_{50}$ between 2.1 µM≤5.0 µM, the letter "E" means the compound has an $EC_{50}$ between 5.1 µM≤10 µM, the letter "F" means the compound has an $EC_{50}$>10 µM.

What is claimed:

1. A method of increasing the LDL uptake or the LDL receptor level in at least one cell, the method comprising contacting the at least one cell with a therapeutically effective amount of at least one agent comprising a compound of formula (XV) and at least one pharmaceutically acceptable carrier or excipient; and any pharmaceutically acceptable salts thereof

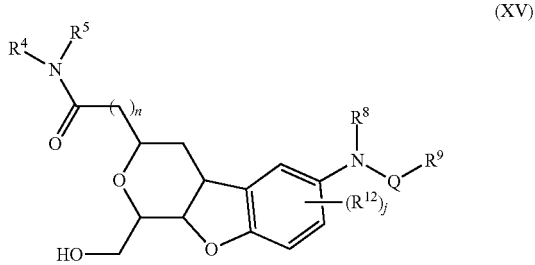

(XV)

wherein in the compound of formula (XV):
Q is $S(O)_p$, C(O), bond, $C(O)NR^8$, $C(O)CH_2$, C(O)O, or $C(O)OCH_2$;
$R^{12}$ is halogen, $C_1$-$C_8$ alkyl, $CF_3$, $N(C_1$-$C_8$ alkyl$)_2$ or $OR^{13}$;
$R^{13}$ is $C_1$-$C_8$ alkyl or hydrogen;
$R^4$ and $R^5$ are each independently selected from the group consisting of hydrogen, 4-6 membered heterocyclic ring, $C_3$-$C_8$ cycloalkyl ring and $(CH_2)_S$-aromatic ring,
further wherein the heterocyclic, cycloalkyl, or aromatic ring is unsubstituted or substituted with one or more $R^x$;
or $R^4$ and $R^5$ taken together form a 4-6 membered heterocyclic ring,
optionally substituted at two adjacent carbon atoms on the heterocylic ring, which can optionally be taken together to form a fused aromatic ring;
$R^6$ is selected from the group consisting of hydrogen, $O(C_1$-$C_8$ alkyl), O-aromatic ring, $O(C_3$-$C_8$ cycloalkyl ring), and OH;
$R^x$ is selected from the group consisting of $(CH_2)_g$-aromatic ring and $OR^{10}$, or two $R^x$ on adjacent carbon atoms are taken together form a fused aromatic ring;
$R^{10}$ is aromatic ring;
$R^8$ and $R^9$ are each independently selected from the group consisting of hydrogen, $C_1$-$C_8$ alkyl, $(CH_2)_t$-4-8 membered heterocyclic ring, and $(CH_2)_v$-aromatic ring,
further where the alkyl, aromatic ring or heterocyclic ring are unsubstituted or substituted with one or more $R^z$;
$R^z$ is selected from halogen, $CF_3$, $C_1$-$C_8$ alkyl, and $O(C_1$-$C_8$ alkyl$)_2$;
or two $R^z$ on adjacent carbon atoms taken together form a 1,3-dioxole ring;
or $R^8$ and $R^9$ taken together form a 4-8 membered heterocyclic ring,
further wherein the heterocyclic ring is unsubstituted or substituted with one or more $R^m$;
$R^m$ is halogen, $CF_3$, $C_1$-$C_8$ alkyl, or $OR^{17}$;
$R^{17}$ is hydrogen or $C_1$-$C_8$ alkyl;
s is 0, 1, 2, or 3;
p is 0, 1, or 2;
n is 0, 1, 2, or 3;
j is 0, 1, 2, or 3;
v is 0, 1, 2, or 3;
t is 0, 1, 2, or 3; and
g is 0, 1, 2 or 3;
whereby the at least one agent increases the LDL uptake or the LDL receptor level in the at least one cell.

2. The method of claim 1, wherein the at least one cell is selected from the group consisting of a hepatic, skin, adrenal gland, muscle, and kidney cell.

3. The method of claim 2, wherein the at least one cell is a HepG2 cell.

4. A method of treating or preventing a lipoprotein-related or cholesterol-related disorder in a subject in need thereof, the method comprising administering to the subject a therapeutically effective amount of at least one agent comprising a compound of formula (XV),

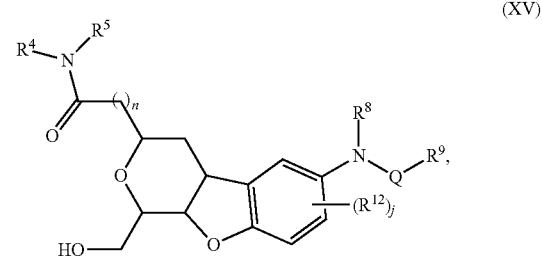

(XV)

wherein in the compound of formula (XV):
Q is $S(O)_p$, C(O), bond, $C(O)NR^8$, $C(O)CH_2$, C(O)O, or $C(O)OCH_2$;

$R^{12}$ is halogen, $C_1$-$C_8$ alkyl, $CF_3$, $N(C_1$-$C_8$ alkyl$)_2$ or $OR^{13}$;

$R^{13}$ is $C_1$-$C_8$ alkyl or hydrogen;

$R^4$ and $R^5$ are each independently selected from the group consisting of hydrogen, 4-6 membered heterocyclic ring, $C_3$-$C_8$ cycloalkyl ring and $(CH_2)_S$-aromatic ring, further wherein the heterocyclic, cycloalkyl, or aromatic ring is unsubstituted or substituted with one or more $R^x$;

or $R^4$ and $R^5$ taken together form a 4-6 membered heterocyclic ring, optionally substituted at two adjacent carbon atoms on the heterocylic ring, which can optionally be taken together to form a fused aromatic ring;

$R^6$ is selected from the group consisting of hydrogen, $O(C_1$-$C_8$ alkyl), O-aromatic ring, $O(C_3$-$C_8$ cycloalkyl ring), and OH;

$R^x$ is selected from the group consisting of $(CH_2)_g$-aromatic ring and $OR^{10}$, or two $R^x$ on adjacent carbon atoms are taken together form a fused aromatic ring;

$R^{10}$ is aromatic ring;

$R^8$ and $R^9$ are each independently selected from the group consisting of hydrogen, $C_1$-$C_8$ alkyl, $(CH_2)_t$-4-8 membered heterocyclic ring, and $(CH_2)_v$-aromatic ring, further where the alkyl, aromatic ring or heterocyclic ring are unsubstituted or substituted with one or more $R^z$;

$R^z$ is selected from halogen, $CF_3$, $C_1$-$C_8$ alkyl, and $O(C_1$-$C_8$ alkyl$)_2$;

or two $R^z$ on adjacent carbon atoms taken together form a 1,3-dioxole ring;

or $R^8$ and $R^9$ taken together form a 4-8 membered heterocyclic ring, further wherein the heterocyclic ring is unsubstituted or substituted with one or more $R^m$;

$R^m$ is halogen, $CF_3$, $C_1$-$C_8$ alkyl, or $OR^{17}$;

$R^{17}$ is hydrogen or $C_1$-$C_8$ alkyl;

s is 0, 1, 2, or 3;
p is 0, 1, or 2;
n is 0, 1, 2, or 3;
j is 0, 1, 2, or 3;
v is 0, 1, 2, or 3;
t is 0, 1, 2, or 3; and
g is 0, 1, 2 or 3;

or a pharmaceutically acceptable salt or solvate thereof, whereby the lipoprotein-related or cholesterol-related disorder in the subject is treated or prevented.

5. A method of treating or preventing a lipoprotein related liver or cardiovascular disease in a subject in need thereof, the method comprising administering to the subject a therapeutically effective amount of at least one agent comprising a compound of formula (XV),

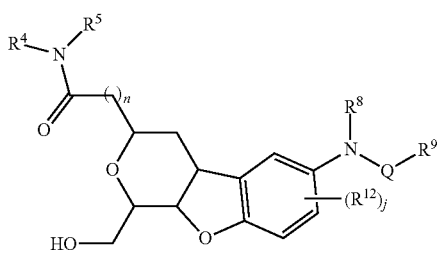

(XV)

wherein in the compound of formula (XV):

Q is $S(O)_p$, C(O), bond, $C(O)NR^8$, $C(O)CH_2$, C(O)O, or $C(O)OCH_2$;

$R^{12}$ is halogen, $C_1$-$C_8$ alkyl, $CF_3$, $N(C_1$-$C_8$ alkyl$)_2$ or $OR^{13}$;

$R^{13}$ is $C_1$-$C_8$ alkyl or hydrogen;

$R^4$ and $R^5$ are each independently selected from the group consisting of hydrogen, 4-6 membered heterocyclic ring, $C_3$-$C_8$ cycloalkyl ring and $(CH_2)_S$-aromatic ring, further wherein the heterocyclic, cycloalkyl, or aromatic ring is unsubstituted or substituted with one or more $R^x$;

or $R^4$ and $R^5$ taken together form a 4-6 membered heterocyclic ring, optionally substituted at two adjacent carbon atoms on the heterocylic ring, which can optionally be taken together to form a fused aromatic ring;

$R^6$ is selected from the group consisting of hydrogen, $O(C_1$-$C_8$ alkyl), O-aromatic ring, $O(C_3$-$C_8$ cycloalkyl ring), and OH;

$R^x$ is selected from the group consisting of $(CH_2)_g$-aromatic ring and $OR^{10}$, or two $R^x$ on adjacent carbon atoms are taken together form a fused aromatic ring;

$R^{10}$ is aromatic ring;

$R^8$ and $R^9$ are each independently selected from the group consisting of hydrogen, $C_1$-$C_8$ alkyl, $(CH_2)_t$-4-8 membered heterocyclic ring, and $(CH_2)_v$-aromatic ring, further where the alkyl, aromatic ring or heterocyclic ring are unsubstituted or substituted with one or more $R^z$;

$R^z$ is selected from halogen, $CF_3$, $C_1$-$C_8$ alkyl, and $O(C_1$-$C_8$ alkyl$)_2$;

or two $R^z$ on adjacent carbon atoms taken together form a 1,3-dioxole ring;

or $R^8$ and $R^9$ taken together form a 4-8 membered heterocyclic ring, further wherein the heterocyclic ring is unsubstituted or substituted with one or more $R^m$;

$R^m$ is halogen, $CF_3$, $C_1$-$C_8$ alkyl, or $OR^{17}$;

$R^{17}$ is hydrogen or $C_1$-$C_8$ alkyl;

s is 0, 1, 2, or 3;
p is 0, 1, or 2;
n is 0, 1, 2, or 3;
j is 0, 1, 2, or 3;
v is 0, 1, 2, or 3;
t is 0, 1, 2, or 3; and
g is 0, 1, 2 or 3;

or a pharmaceutically acceptable salt thereof, whereby the liver or cardiovascular disease is treated or prevented in the subject.

6. The method of claim 5, wherein the cardiovascular disease is myocardial infarction, coronary heart disease, atherosclerosis, or hypercholesterolemia.

7. The method of claim 5, wherein the liver disease or disorder is liver cirrhosis, hepatocellular carcinoma, liver injury, or abnormal liver function.

8. The method of claim 5, wherein administration of the agent has at least one effect selected from the group consisting of: increases LDL-cholesterol uptake, upregulates the expression level of LDLR, reduces LDL-cholesterol, elevates HDL-cholesterol, reduces total serum cholesterol, upregulates expression level of TRIB1, and downregulates PCSK9 expression.

9. A method of assessing the efficacy of a therapeutic agent for treating a lipoprotein related disease in a subject, the method comprising:
(a) administering a compound of formula (XV), (XV)

wherein in the compound of formula (XV):
Q is $S(O)_p$, $C(O)$, bond, $C(O)NR^8$, $C(O)CH_2$, $C(O)O$, or $C(O)OCH_2$;
$R^{12}$ is halogen, $C_1$-$C_8$ alkyl, $CF_3$, $N(C_1$-$C_8$ alkyl$)_2$ or $OR^{13}$;
$R^{13}$ is $C_1$-$C_8$ alkyl or hydrogen;
$R^4$ and $R^5$ are each independently selected from the group consisting of hydrogen, 4-6 membered heterocyclic ring, $C_3$-$C_8$ cycloalkyl ring and $(CH_2)_S$-aromatic ring,
further wherein the heterocyclic, cycloalkyl, or aromatic ring is unsubstituted or substituted with one or more $R^x$;
or $R^4$ and $R^5$ taken together form a 4-6 membered heterocyclic ring,
optionally substituted at two adjacent carbon atoms on the heterocylic ring, which can optionally be taken together to form a fused aromatic ring;
$R^6$ is selected from the group consisting of hydrogen, $O(C_1$-$C_8$ alkyl), O-aromatic ring, $O(C_3$-$C_8$ cycloalkyl ring), and OH;
$R^x$ is selected from the group consisting of $(CH_2)_g$-aromatic ring and $OR^{10}$, or two $R^x$ on adjacent carbon atoms are taken together form a fused aromatic ring;
$R^{10}$ is aromatic ring;
$R^8$ and $R^9$ are each independently selected from the group consisting of hydrogen, $C_1$-$C_8$ alkyl, $(CH_2)_t$-4-8 membered heterocyclic ring, and $(CH_2)_v$-aromatic ring,
further where the alkyl, aromatic ring or heterocyclic ring are unsubstituted or substituted with one or more $R^z$;
$R^z$ is selected from halogen, $CF_3$, $C_1$-$C_8$ alkyl, and $O(C_1$-$C_8$ alkyl$)_2$;
or two $R^z$ on adjacent carbon atoms taken together form a 1,3-dioxole ring;
or $R^8$ and $R^9$ taken together form a 4-8 membered heterocyclic ring,
further wherein the heterocyclic ring is unsubstituted or substituted with one or more $R^m$;
$R^m$ is halogen, $CF_3$, $C_1$-$C_8$ alkyl, or $OR^{17}$;
$R^{17}$ is hydrogen or $C_1$-$C_8$ alkyl;
s is 0, 1, 2, or 3;
p is 0, 1, or 2;
n is 0, 1, 2, or 3;
j is 0, 1, 2, or 3;
v is 0, 1, 2, or 3;
t is 0, 1, 2, or 3; and
g is 0, 1, 2 or 3;
to the subject; and
(b) measuring the expression of a signature gene selected from the group consisting of TRIB1, SCAP, SREBF1, SREBF2, PCSK9, LDLR, HMGCR, HMGCS, FASN, SCD1, MTTP, APOC3, ApoB, and a LDLR, in a sample of the subject by quantitative PCR, L-1000 assay or measuring the expression of a protein product of the signature gene by ELISA or FACS analysis relative to a reference,
wherein an increase in the expression as compared to the reference indicates that the therapeutic agent is effective for treating the disease.

10. A method of monitoring level of circulating lipid in a subject, the method comprising:
(a) administering a compound of formula (XV), (XV)

wherein in the compound of formula (XV):
Q is $S(O)_p$, $C(O)$, bond, $C(O)NR^8$, $C(O)CH_2$, $C(O)O$, or $C(O)OCH_2$;
$R^{12}$ is halogen, $C_1$-$C_8$ alkyl, $CF_3$, $N(C_1$-$C_8$ alkyl$)_2$ or $OR^{13}$;
$R^{13}$ is $C_1$-$C_8$ alkyl or hydrogen;
$R^4$ and $R^5$ are each independently selected from the group consisting of hydrogen, 4-6 membered heterocyclic ring, $C_3$-$C_8$ cycloalkyl ring and $(CH_2)_S$-aromatic ring,
further wherein the heterocyclic, cycloalkyl, or aromatic ring is unsubstituted or substituted with one or more $R^x$;
or $R^4$ and $R^5$ taken together form a 4-6 membered heterocyclic ring,
optionally substituted at two adjacent carbon atoms on the heterocylic ring, which can optionally be taken together to form a fused aromatic ring;
$R^6$ is selected from the group consisting of hydrogen, $O(C_1$-$C_8$ alkyl), O-aromatic ring, $O(C_3$-$C_8$ cycloalkyl ring), and OH;
$R^x$ is selected from the group consisting of $(CH_2)_g$-aromatic ring and $OR^{10}$, or two $R^x$ on adjacent carbon atoms are taken together form a fused aromatic ring;
$R^{10}$ is aromatic ring;
$R^8$ and $R^9$ are each independently selected from the group consisting of hydrogen, $C_1$-$C_8$ alkyl, $(CH_2)_t$-4-8 membered heterocyclic ring, and $(CH_2)_v$-aromatic ring,
further where the alkyl, aromatic ring or heterocyclic ring are unsubstituted or substituted with one or more $R^z$;
$R^z$ is selected from halogen, $CF_3$, $C_1$-$C_8$ alkyl, and $O(C_1$-$C_8$ alkyl$)_2$;
or two $R^z$ on adjacent carbon atoms taken together form a 1,3-dioxole ring;

or $R^8$ and $R^9$ taken together form a 4-8 membered heterocyclic ring,
   further wherein the heterocyclic ring is unsubstituted or substituted with one or more $R^m$;
$R^m$ is halogen, $CF_3$, $C_1$-$C_8$ alkyl, or $OR^{17}$,
$R^{17}$ is hydrogen or $C_1$-$C_8$ alkyl,
s is 0, 1, 2, or 3,
p is 0, 1, or 2,
n is 0, 1, 2, or 3,
j is 0, 1, 2, or 3,
v is 0, 1, 2, or 3,
t is 0, 1, 2, or 3, and
g is 0, 1, 2 or 3,
to the subject and
(b) measuring in a sample from the subject circulating lipid relative to a reference, wherein the reference is the level of circulating lipid present in a sample obtained from the subject at an earlier point in time.

11. A pharmaceutical composition comprising at least one agent comprising a compound of formula (XV)

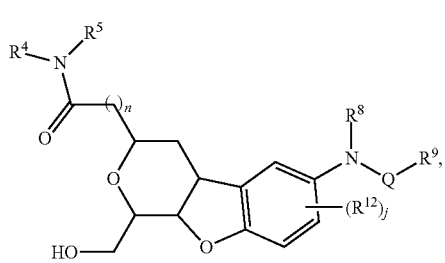

(XV)

wherein in the compound of formula (XV):
Q is $S(O)_p$, C(O), bond, $C(O)NR^8$, $C(O)CH_2$, C(O)O, or $C(O)OCH_2$;
$R^{12}$ is halogen, $C_1$-$C_8$ alkyl, $CF_3$, $N(C_1$-$C_8$ alkyl$)_2$ or $OR^{13}$;
$R^{13}$ is $C_1$-$C_8$ alkyl or hydrogen;
$R^4$ and $R^5$ are each independently selected from the group consisting of hydrogen, 4-6 membered heterocyclic ring, $C_3$-$C_8$ cycloalkyl ring and $(CH_2)_S$-aromatic ring,
   further wherein the heterocyclic, cycloalkyl, or aromatic ring is unsubstituted or substituted with one or more $R^x$;
or $R^4$ and $R^5$ taken together form a 4-6 membered heterocyclic ring,
   optionally substituted at two adjacent carbon atoms on the heterocylic ring, which can optionally be taken together to form a fused aromatic ring;
$R^6$ is selected from the group consisting of hydrogen, $O(C_1$-$C_8$ alkyl), O-aromatic ring, $O(C_3$-$C_8$ cycloalkyl ring), and OH;
$R^x$ is selected from the group consisting of $(CH_2)_g$-aromatic ring and $OR^{10}$, or two $R^x$ on adjacent carbon atoms are taken together form a fused aromatic ring;
$R^{10}$ is aromatic ring;
$R^8$ and $R^9$ are each independently selected from the group consisting of hydrogen, $C_1$-$C_8$ alkyl, $(CH_2)_t$-4-8 membered heterocyclic ring, and $(CH_2)_v$-aromatic ring,
   further where the alkyl, aromatic ring or heterocyclic ring are unsubstituted or substituted with one or more $R^z$;
$R^z$ is selected from halogen, $CF_3$, $C_1$-$C_8$ alkyl, and $O(C_1$-$C_8$ alkyl$)_2$;
   or two $R^z$ on adjacent carbon atoms taken together form a 1,3-dioxole ring;
or $R^8$ and $R^9$ taken together form a 4-8 membered heterocyclic ring,
   further wherein the heterocyclic ring is unsubstituted or substituted with one or more $R^m$;
$R^m$ is halogen, $CF_3$, $C_1$-$C_8$ alkyl, or $OR^{17}$;
$R^{17}$ is hydrogen
s is 0, 1, 2, or 3;
p is 0, 1, or 2;
n is 0, 1, 2, or 3;
j is 0, 1, 2, or 3;
v is 0, 1, 2, or 3;
t is 0, 1, 2, or 3; and
g is 0, 1, 2 or 3; and
or a pharmaceutically acceptable salt or solvate thereof, and one or more additional medicaments, wherein the one or more additional medicaments reduce the level of LDL-cholesterol, elevate the level of HDL-cholesterol, decrease the level total serum cholesterol, upregulate the expression level of LDLR, upregulate the expression level of PCSK9, or downregulate PCSK9 expression.

12. A method of identifying a compound for treating or preventing a lipoprotein related disease, the method comprising:
a) contacting a cell with a compound; and
b) measuring the expression level of a signature gene selected from the group consisting of TRIB1, SCAP, SREBF1, SREBF2, PCSK9, LDLR, HMGCR, HMGCS, FASN, SCD1, MTTP, APOC3, ApoB, and a LDLR, in a sample of the subject by quantitative PCR, L-1000 assay or measuring the expression of a protein product of the signature gene by ELISA or FACS analysis relative to a reference, wherein an increase in the level of expression as compared to the reference identifies the compound as treating or preventing the disease.

13. The method of claim 12, wherein the cell is selected from the group consisting of hepatic, skin, adrenal gland, muscle, and kidney cells.

* * * * *